(12) United States Patent
Semler et al.

(10) Patent No.: US 9,889,018 B2
(45) Date of Patent: Feb. 13, 2018

(54) EXPANDABLE VERTEBRAL BODY REPLACEMENT DEVICE AND METHOD

(71) Applicant: MUSC Foundation for Research Development, Charleston, SC (US)

(72) Inventors: Mark Evald Semler, Mount Pleasant, SC (US); Bruce Frankel, Mount Pleasant, SC (US); Joseph Ruscito, Southport, CT (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 15/486,739

(22) Filed: Apr. 13, 2017

(65) Prior Publication Data

US 2017/0216050 A1    Aug. 3, 2017

Related U.S. Application Data

(63) Continuation-in-part of application No. 14/665,833, filed on Mar. 23, 2015.

(Continued)

(51) Int. Cl.
*A61F 2/44* (2006.01)
*A61F 2/46* (2006.01)

(52) U.S. Cl.
CPC .......... *A61F 2/4425* (2013.01); *A61F 2/4611* (2013.01); *A61F 2230/0069* (2013.01); *A61F 2250/0009* (2013.01)

(58) Field of Classification Search
CPC ............ A61B 17/7065; A61B 17/7068; A61B 17/7062; A61B 17/8875; A61B 17/7064;

(Continued)

(56) References Cited

U.S. PATENT DOCUMENTS

| 4,401,112 A | * | 8/1983 | Rezaian | A61F 2/44 606/279 |
| 4,657,550 A | | 4/1987 | Daher | |

(Continued)

FOREIGN PATENT DOCUMENTS

| WO | 20100124008 | 10/2010 |
| WO | 20130003736 | 1/2013 |

(Continued)

OTHER PUBLICATIONS

International Search Report for PCT/US2016/020209 dated Jul. 25, 2016, 7 pages.

(Continued)

*Primary Examiner* — Eduardo C Robert
*Assistant Examiner* — Tara R Carter
(74) *Attorney, Agent, or Firm* — Heslin Rothenberg Farley & Mesiti P.C.; Jacquelyn A. Graff

(57) ABSTRACT

Expandable vertebral body implants, systems, instruments, and methods of assembly and using the implants, systems, and instruments are disclosed. The vertebral body implant includes a body with a first end and a second end, a first rotating member rotatably coupled to the first end, wherein an end includes a plurality of first notches inset into the first rotating member, a second rotating member rotatably coupled to the second end, wherein an end includes a plurality of second notches inset into the second rotating member, a first extension member moveably coupled to the first end, and a second extension member moveably coupled to the second end. The expandable cage system comprises a vertebral body implant and an insertion instrument. Methods for assembling and using the vertebral body implants and instruments are also disclosed.

10 Claims, 66 Drawing Sheets

Related U.S. Application Data

(60) Provisional application No. 62/427,149, filed on Nov. 28, 2016.

(58) Field of Classification Search
CPC ............ A61B 17/7082; A61B 17/8872; A61B 2017/681; A61B 17/70
USPC ................................ 606/250–279; 623/17.11
See application file for complete search history.

(56) References Cited

U.S. PATENT DOCUMENTS

| | | | |
|---|---|---|---|
| 5,083,621 A | | 1/1992 | Sheridan |
| 5,336,223 A | * | 8/1994 | Rogers ...................... A61F 2/44 606/258 |
| 5,702,453 A | * | 12/1997 | Rabbe .................... A61B 17/70 606/247 |
| 5,702,455 A | | 12/1997 | Saggar |
| 6,802,867 B2 | | 10/2004 | Manasas et al. |
| 7,384,431 B2 | | 6/2008 | Berry |
| 7,575,601 B2 | | 8/2009 | Dickson |
| 7,641,693 B2 | | 1/2010 | Gutlin et al. |
| 8,157,864 B2 | | 4/2012 | Rogeau et al. |
| 8,182,535 B2 | | 5/2012 | Kraus |
| 8,246,680 B2 | | 8/2012 | Betz et al. |
| 8,252,054 B2 | | 8/2012 | Greenhalgh et al. |
| 8,366,779 B2 | | 2/2013 | Dickson et al. |
| 8,540,770 B2 | | 9/2013 | Woodburn, Sr. et al. |
| 8,568,482 B2 | | 10/2013 | Kraus et al. |
| 8,585,763 B2 | | 11/2013 | Olevsky et al. |
| 8,690,886 B2 | | 4/2014 | Fedorov et al. |
| 8,721,723 B2 | | 5/2014 | Hansell et al. |
| 8,740,980 B2 | * | 6/2014 | Merves ..................... A61F 2/44 623/17.15 |
| 8,992,617 B2 | | 3/2015 | Woodburn et al. |
| 9,241,808 B2 | | 1/2016 | Sabatino |
| 9,320,612 B2 | | 4/2016 | Soumac et al. |
| 2004/0059271 A1 | * | 3/2004 | Berry ........................ A61F 2/44 602/32 |
| 2006/0074490 A1 | * | 4/2006 | Sweeney ................... A61F 2/44 623/17.15 |
| 2007/0255407 A1 | | 11/2007 | Castleman et al. |
| 2009/0112325 A1 | | 4/2009 | Refai et al. |
| 2010/0094424 A1 | | 4/2010 | Woodburn et al. |
| 2010/0211119 A1 | * | 8/2010 | Refai ........................ A61F 2/44 606/86 A |
| 2010/0274357 A1 | | 10/2010 | Miller et al. |
| 2013/0310938 A1 | | 11/2013 | Soumac et al. |
| 2013/0331943 A1 | | 12/2013 | Arnold et al. |
| 2014/0058517 A1 | | 2/2014 | Sabatino |
| 2014/0088708 A1 | | 3/2014 | McLaughlin et al. |
| 2014/0107786 A1 | | 4/2014 | Geisler et al. |
| 2014/0156006 A1 | | 6/2014 | Bannigan et al. |
| 2014/0222151 A1 | | 8/2014 | Refai et al. |

FOREIGN PATENT DOCUMENTS

| | | |
|---|---|---|
| WO | 20130003738 | 1/2013 |
| WO | 2013173682 | 11/2013 |

OTHER PUBLICATIONS

Written Opinion for PCT/US2016/020209 dated Jul. 25, 2016, 10 pages.
International Search Report for PCT/US2017/031093 dated Aug. 10, 2017, 6 pages.
Written Opinion for PCT/US2017/031093 dated Aug. 10, 2017, 7 pages.

* cited by examiner

EXPANDABLE VERTEBRAL BODY REPLACEMENT DEVICE AND METHOD

CROSS REFERENCE TO RELATED APPLICATION

This application is a continuation-in-part application of U.S. application Ser. No. 14/665,833 filed Mar. 23, 2015 and also claims priority benefit under 35 U.S.C. §119(e) of U.S. provisional patent application No. 62/427,149 filed Nov. 28, 2016, which are each incorporated herein by reference in their entireties.

FIELD OF THE INVENTION

The present invention relates generally to a medical implants for insertion in a space between a patient's vertebrae. More specifically, but not exclusively, the present invention concerns expandable vertebral body replacement devices for implantation in a patient's spine between the vertebrae.

BACKGROUND OF THE INVENTION

Trauma or disease, such as, tumors may cause pressure on a patient's spinal cord. In order to alleviate the pressure and likely the pain it is causing, surgeons may remove part or all of a patient's vertebral bodies and adjacent vertebral discs in the location of the pressure, during a procedure, such as, a corpectomy. Often implants are used to replace the removed vertebral bodies to maintain the space between the remaining vertebral bodies.

SUMMARY OF THE INVENTION

Aspects of the present invention provide expanding vertebral body replacement devices for implantation in a patient's spine between the vertebrae and methods of using the same.

In one aspect, provided herein is a vertebral body implant, including a body with a first end and a second end, a first rotating member rotatably coupled to the first end, wherein an end includes a plurality of first notches inset into the first rotating member, a second rotating member rotatably coupled to the second end, wherein an end includes a plurality of second notches inset into the second rotating member, a first extension member moveably coupled to the first end, and a second extension member moveably coupled to the second end.

In another aspect, provided herein is an expandable cage system including a vertebral body device and an insertion instrument. The vertebral body device including a body with a first end and a second end, a first rotating member coupled to the first end, a second rotating member coupled to the second end, a first extension member moveably coupled to the first end, and a second extension member moveably coupled to the second end. The body including at least one aperture positioned on the body along a midpoint between the first end and the second end. The body also including at least one first locking hole positioned superior to the at least one aperture and at least one second locking hole positioned inferior to the at least one aperture. The insertion instrument, wherein the at least one aperture, the at least one first locking hole, and the at least one second locking hole are sized to receive the insertion instrument.

In yet another aspect, provided herein is a method for using an expandable cage system, including obtaining a vertebral body implant and an insertion instrument. The vertebral body device including a body with a first end and a second end, a first rotating member rotatably coupled to the first end, a second rotating member rotatably coupled to the second end, a first extension member moveably coupled to the first end, and a second extension member moveably coupled to the second end. The method also includes coupling the vertebral body implant to the insertion instrument and inserting the vertebral body implant into a patient between two vertebral bodies. The method further includes expanding the vertebral body implant and removing the insertion instrument.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
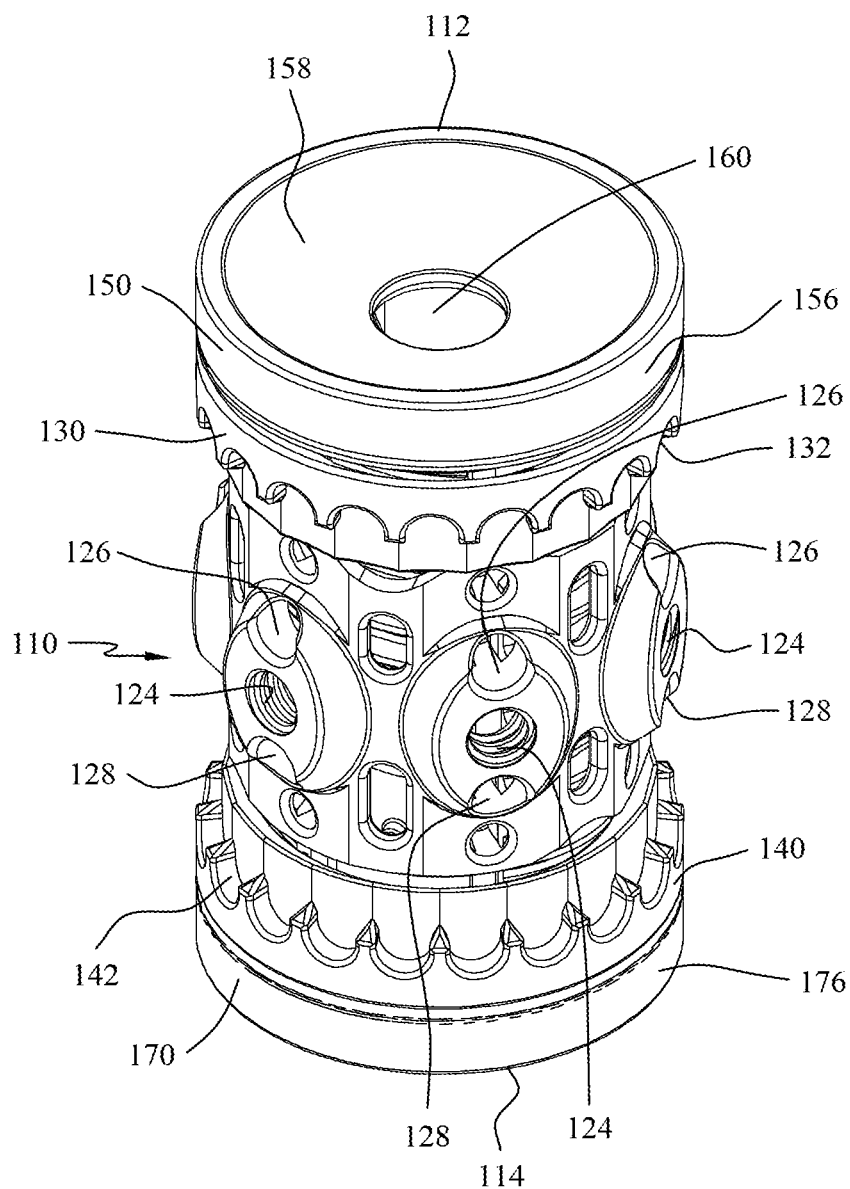
FIG. 1 is a top perspective view of a vertebral body device, in accordance with an aspect of the present invention.
Figure 2:
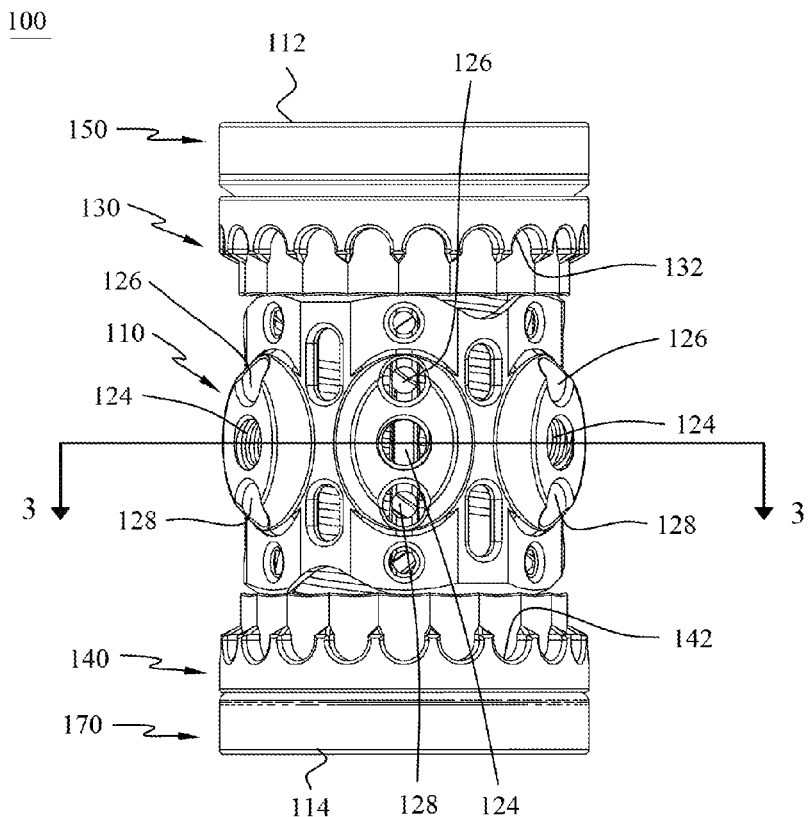
FIG. 2 is a side view of the vertebral body device of FIG. 1, in accordance with an aspect of the present invention.
Figure 3:
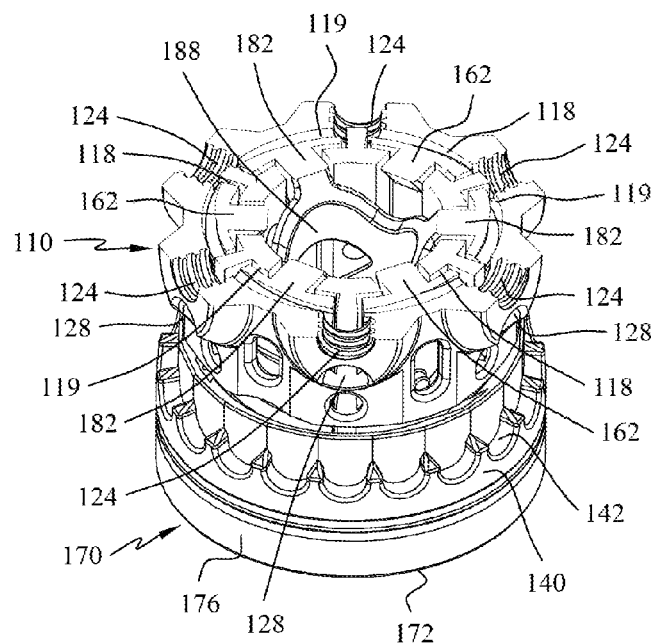
FIG. 3 is a cross-sectional view of the vertebral body device of FIG. 1 taken along line 3-3 in FIG. 2, in accordance with an aspect of the present invention.

Generally stated, disclosed herein is an expandable vertebral body replacement device. Further, methods of assembling and using the expandable vertebral body replacement device are discussed.

In this detailed description and the following claims, the words proximal, distal, anterior, posterior, medial, lateral, superior, inferior, cephalad, and caudal are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above, "inferior" means a direction below another object or structure, "cephalad" means a direction toward the head, and "caudal" means a direction toward the inferior part of the body.

Referring to the drawings, wherein like reference numerals are used to indicate like or analogous components throughout the several views, and with particular reference to FIGS. 1-5, there is illustrated an exemplary embodiment of an expandable vertebral body replacement device 100. The terms "expandable vertebral body replacement device," "vertebral body device," "device," "expandable vertebral body replacement implant," "vertebral body replacement implant," "vertebral body implant," "implant," "expandable cage," and "cage" may be used interchangeably herein as they essentially describe the same type of device. The vertebral body device 100 may include a body 110, a first rotating member 130 rotatably coupled to the first end 112 of the body 110, a second rotating member 140 rotatably coupled to the second end 114 of the body 110, a first extension member 150 moveably coupled to a first end 112 of the body 110, and a second extension member 170 moveably coupled to a second end 114 of the body 110.

Figure 8:
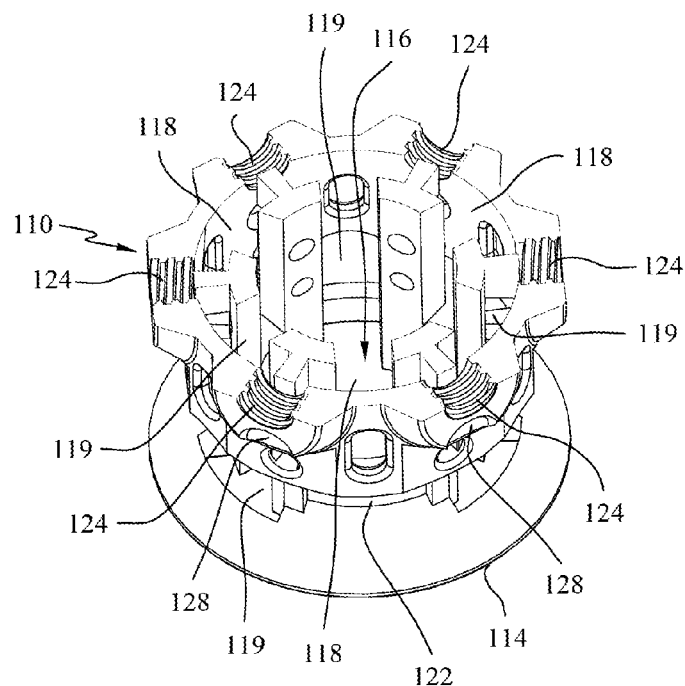
FIG. 8 is a perspective cross-sectional view of the body of FIG. 6 taken along line 8-8 in FIG. 7, in accordance with an aspect of the present invention.
Figure 9:
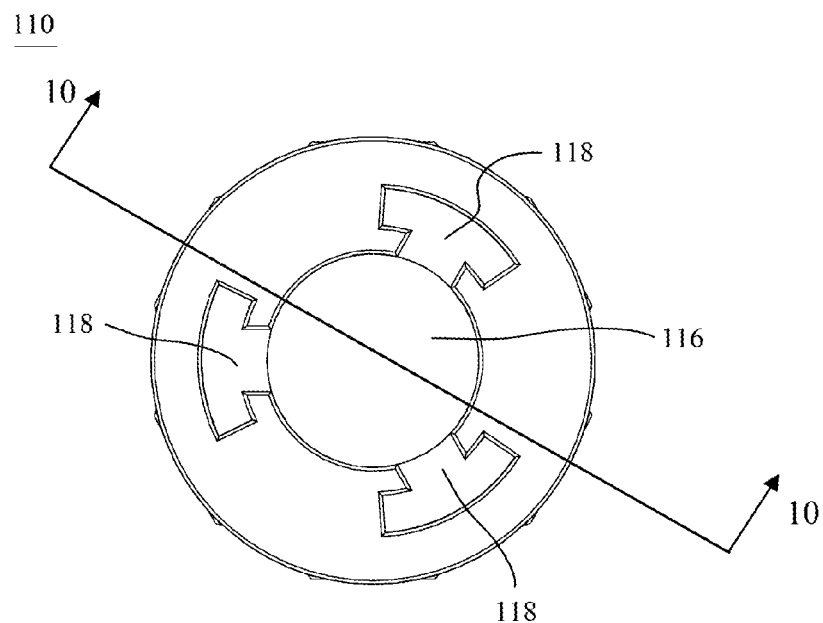
FIG. 9 is a top view of the body of FIG. 6, in accordance with an aspect of the present invention.
Figure 10:
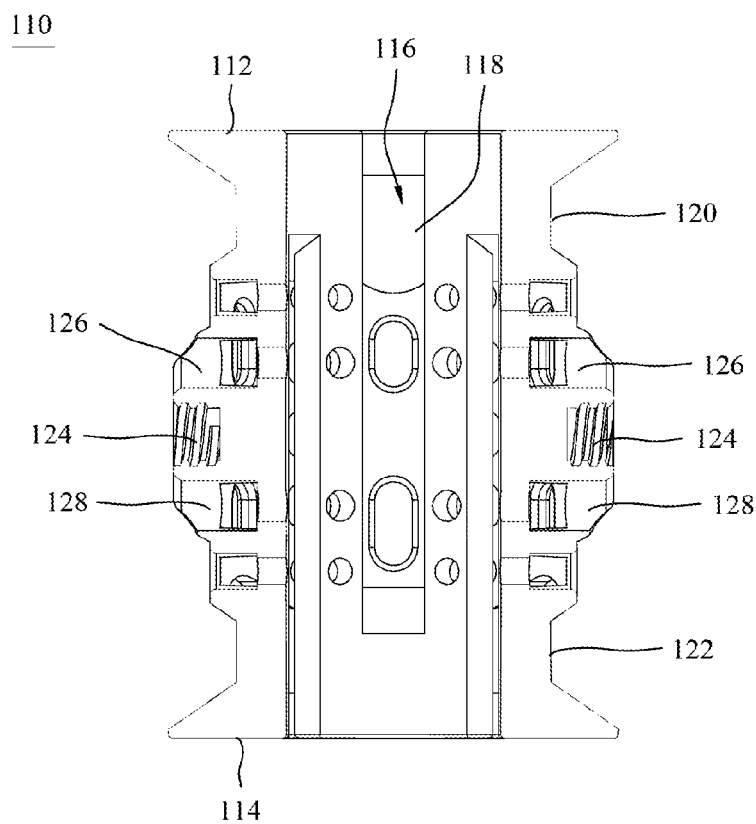
FIG. 10 is a cross-sectional view of the body of FIG. 6 taken along line 10-10 in FIG. 9, in accordance with an aspect of the present invention.

As shown in FIGS. 5, 6, and 8-10, the body 110 may include an opening 116 extending from the first end 112 to the second end 114, for example, along the longitudinal axis of the body 110. The opening 116 may include at least two channels 118, 119 extending into the body 110 from the opening 116. At least one first channel 118 may extend from the first end 112 toward the second end 114 and at least one second channel 119 may extend from the second end 114 toward the first end 112. The channels 118, 119 may be, for example, evenly spaced around the opening 116. As shown, the body 110 may include, for example, three first channels 118 open on the first end 112 and three second channels 119 open on the second end 114. The channels 118, 119 may be spaced evenly apart around the circumference of the opening and may alternate between a first channel 118 and a second channel 119, as shown in FIG. 8. Alternative numbers of channels 118, 119 are also contemplated, for example, the body 110 may include the same number of first channels 118 and second channels 119, more first channels 118 than second channels 119, or more second channels 119 than first channels 118.

The exterior surface of the body 110 may further include a first groove 120 near the first end 112 and a second groove 122 near the second end 114, as shown in FIGS. 4-7 and 10. The first and second grooves 120, 122 may extend around the circumference of the body 110 and be sized to receive the first and second rotating members 130, 140, respectively. The first groove 120 may extend into the first channels 118 to enable the first rotating member 130 to engage the first extension member 150 and the second groove 122 may extend into the channels 119 to enable the second rotating member 140 to engage the second extension member 170. As shown in FIGS. 1-8 and 10, the body 110 may also include a plurality of apertures 124 positioned around the circumference of the exterior surface. The plurality of apertures 124 may be positioned, for example, at a midpoint between the first end 112 and second end 114 of the body 110. The plurality of apertures 124 may be, for example, threaded openings. The body 110 may also include a plurality of first positioning holes 126 superior to the plurality of apertures 124 and a plurality of second positioning holes 128 inferior to the plurality of apertures 124.

Figure 4:
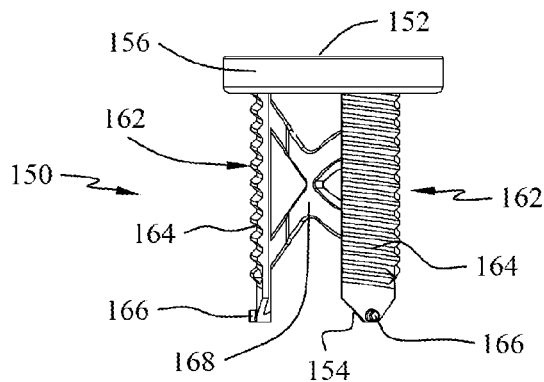
FIG. 4 is an exploded side view of the vertebral body device of FIG. 1, in accordance with an aspect of the present invention.
Figure 4:
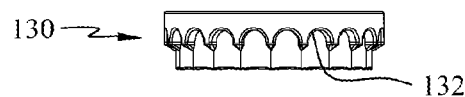
Figure 4:
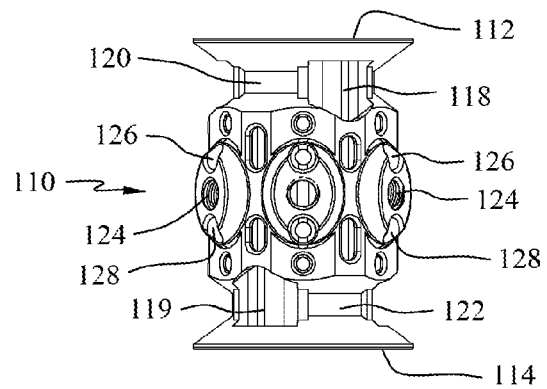
Figure 4:
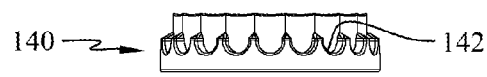
Figure 4:
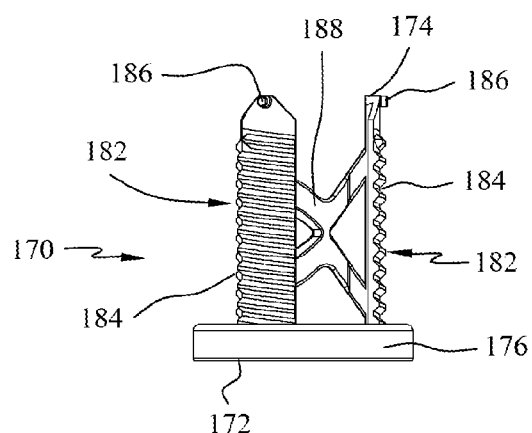
Figure 5:
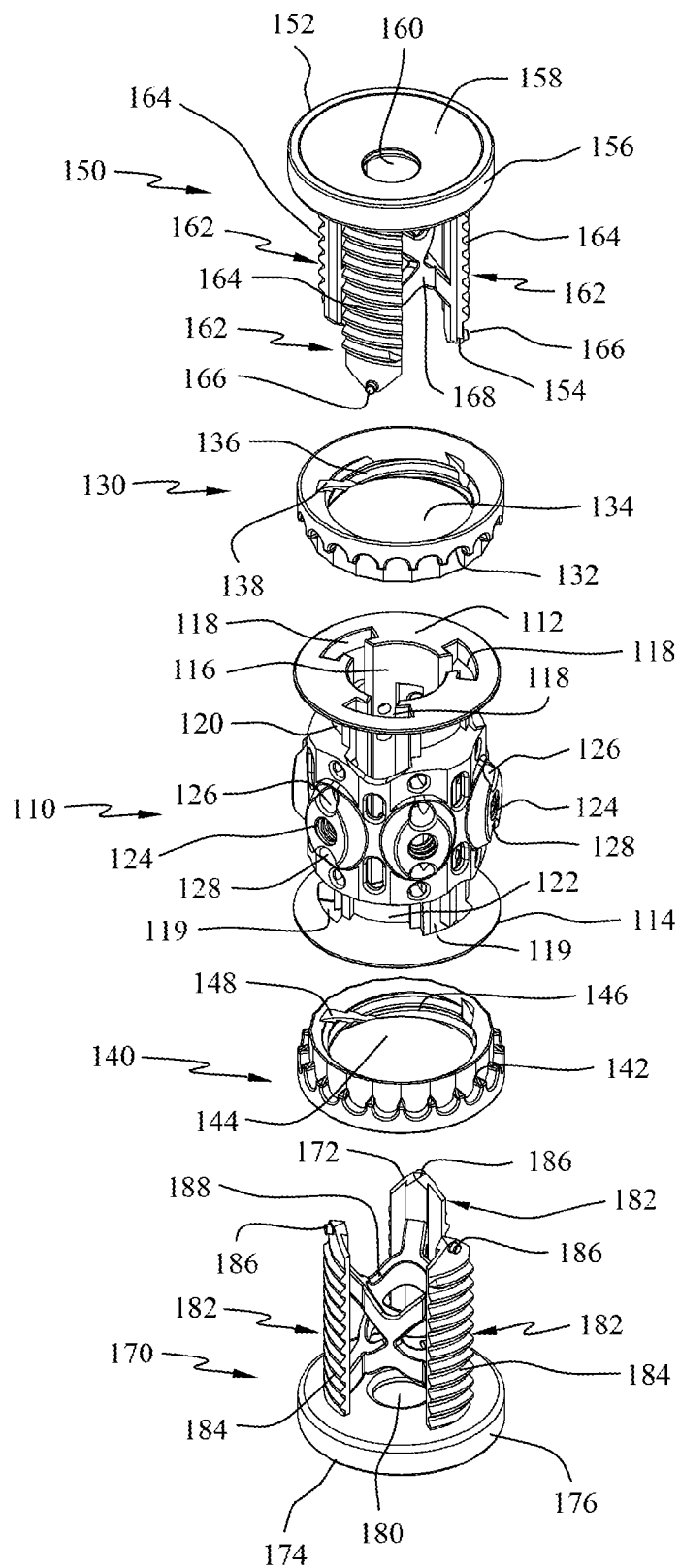
FIG. 5 is an exploded perspective view of the vertebral body device of FIG. 1, in accordance with an aspect of the present invention.
Figure 6:
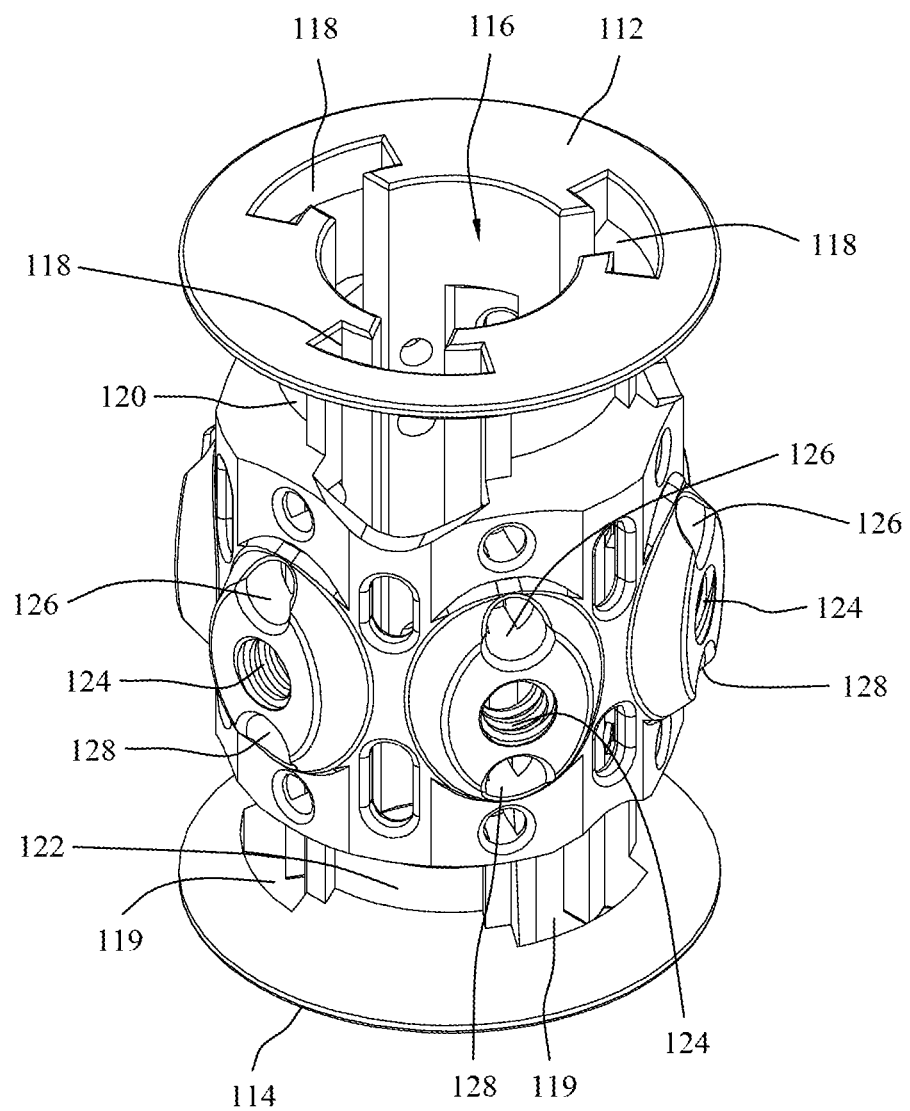
FIG. 6 is a top perspective view of a body of the vertebral body device of FIG. 1, in accordance with an aspect of the present invention.
Figure 7:
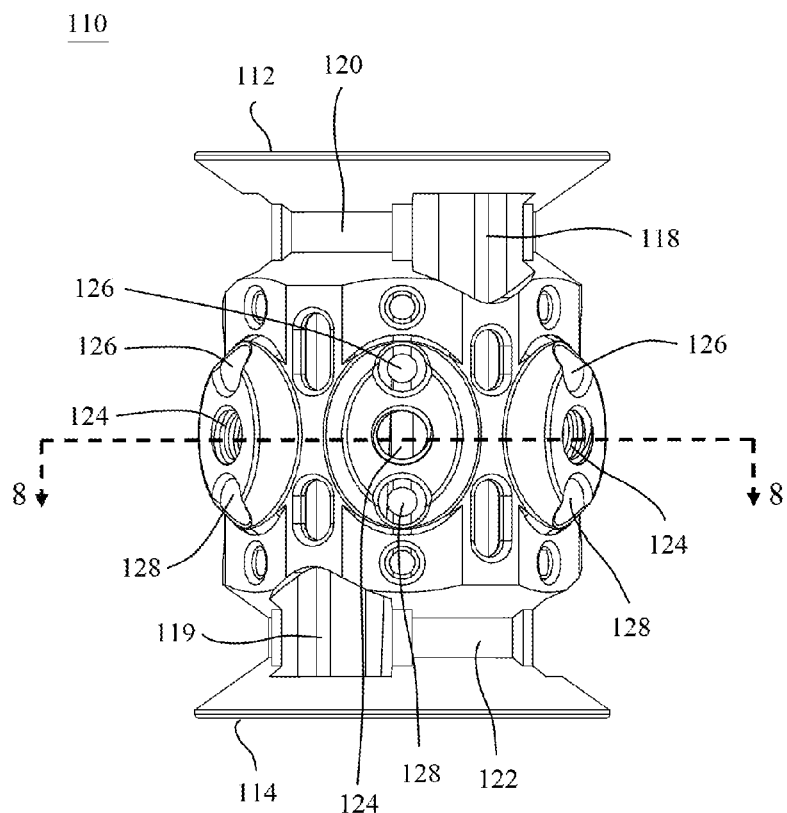
FIG. 7 is a side view of the body of FIG. 6, in accordance with an aspect of the present invention.
Figure 11:
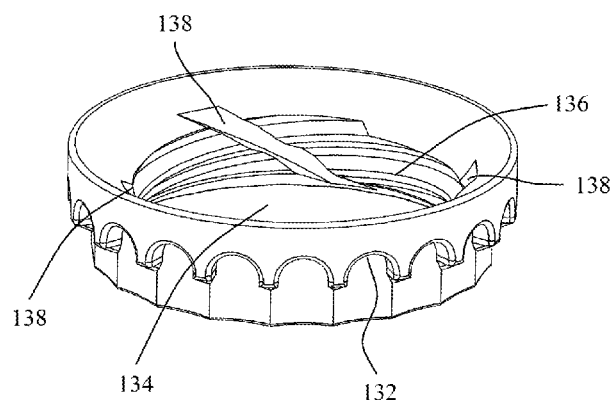
FIG. 11 is a top perspective view of a rotating member of the vertebral body device of FIG. 1, in accordance with an aspect of the present invention.
Figure 12:
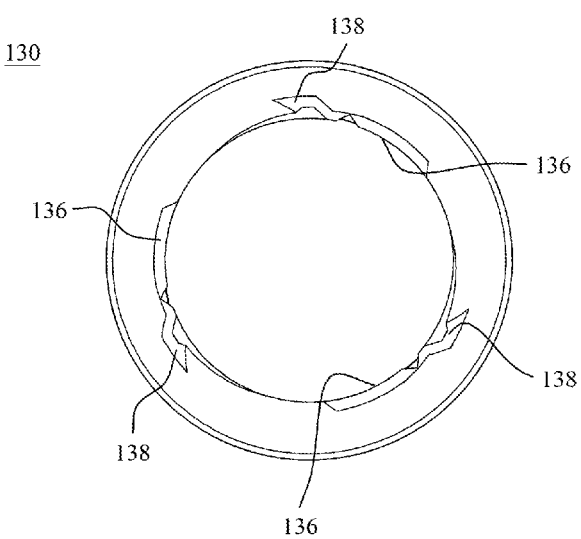
FIG. 12 is a top view of the rotating member of FIG. 11, in accordance with an aspect of the present invention.
Figure 13:
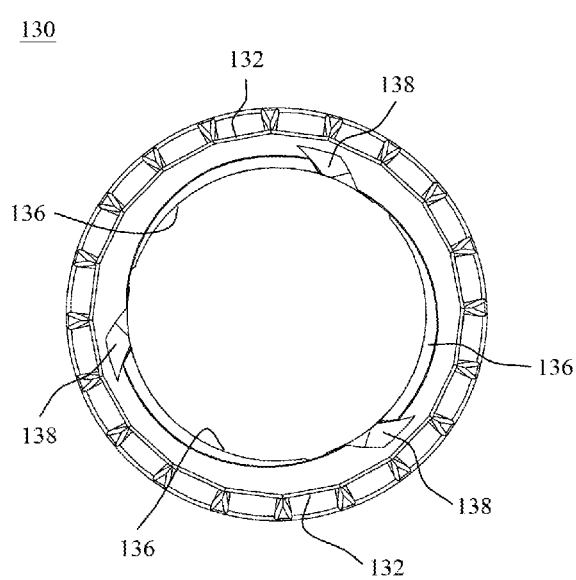
FIG. 13 is a bottom view of the rotating member of FIG. 11, in accordance with an aspect of the present invention.
Figure 14:
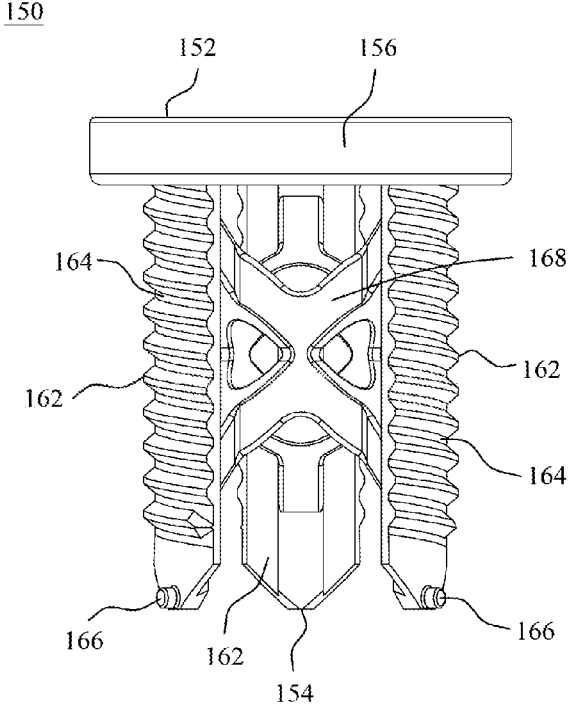
FIG. 14 is a side view of an extension member of the vertebral body device of FIG. 1, in accordance with an aspect of the present invention.

The first rotating member 130 is shown in FIGS. 1-2, 4-5, and 11-13. The first rotating member 130 may include a center opening 134 extending through the first rotating member 130. The exterior surface of the first rotating member 130 may include a plurality of grooves, notches, gear teeth, teeth, or scallops 132, as best seen in FIGS. 11 and 13. The plurality of grooves 132 may be, for example, sized to receive an insertion tool, such as tool 200 described in greater detail below. The first rotating member 130 may also include threads 136 on the interior surface of the member 130, as shown in FIGS. 5 and 11. In addition, the first rotating member 130 may include at least one angled slot 138 to receive a portion of the first extension member 150, as shown in FIGS. 11-13.

The second rotating member 140, as shown in FIGS. 4 and 5, may include a plurality of grooves 142, a center opening 144, threads 146, and angled slots 148. The plurality of grooves 142, center opening 144, threads 146, and angled slots 148 may be of the type described above with reference to the plurality of grooves 132, center opening 134, threads 136, and angled slots 138 of first rotating member 130, which will not be described again here for brevity's sake.

Figure 15:
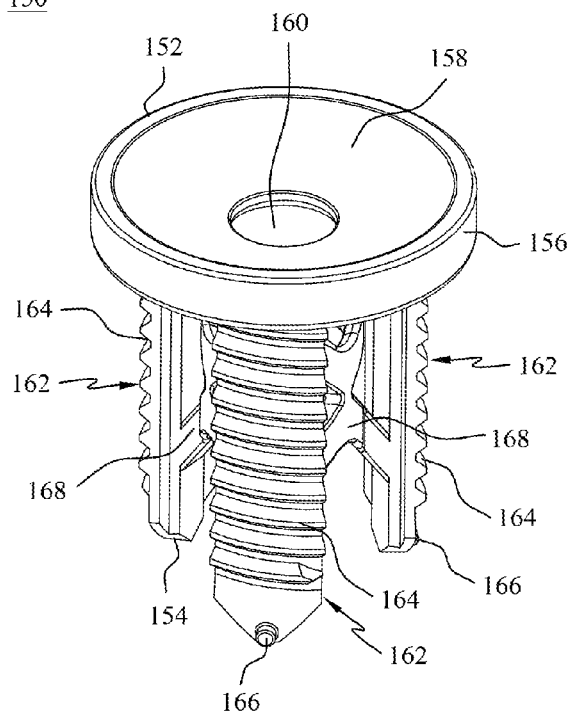
FIG. 15 is a top perspective view of the extension member of FIG. 14, in accordance with an aspect of the present invention.
Figure 16:
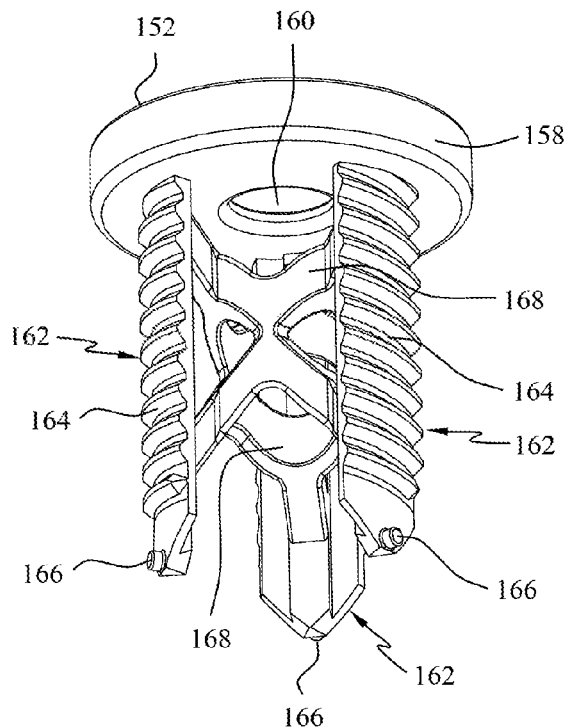
FIG. 16 is a bottom perspective view of the extension member of FIG. 14, in accordance with an aspect of the present invention.
Figure 17:
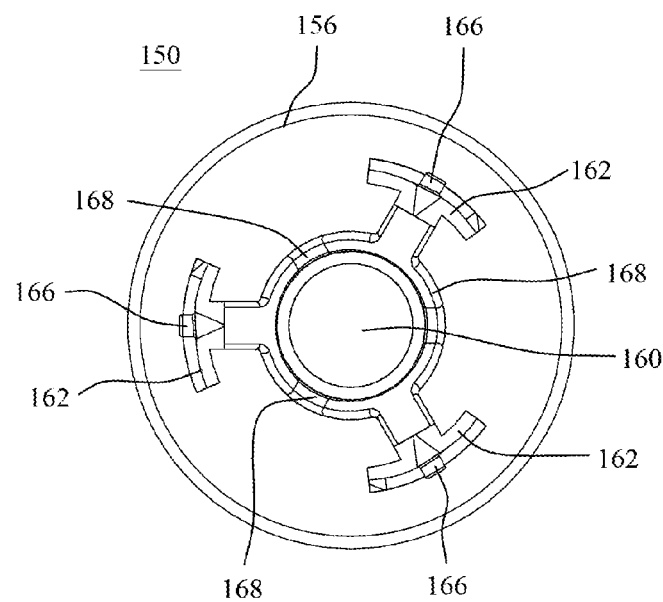
FIG. 17 is a bottom view of the extension member of FIG. 14, in accordance with an aspect of the present invention.
Figure 18:
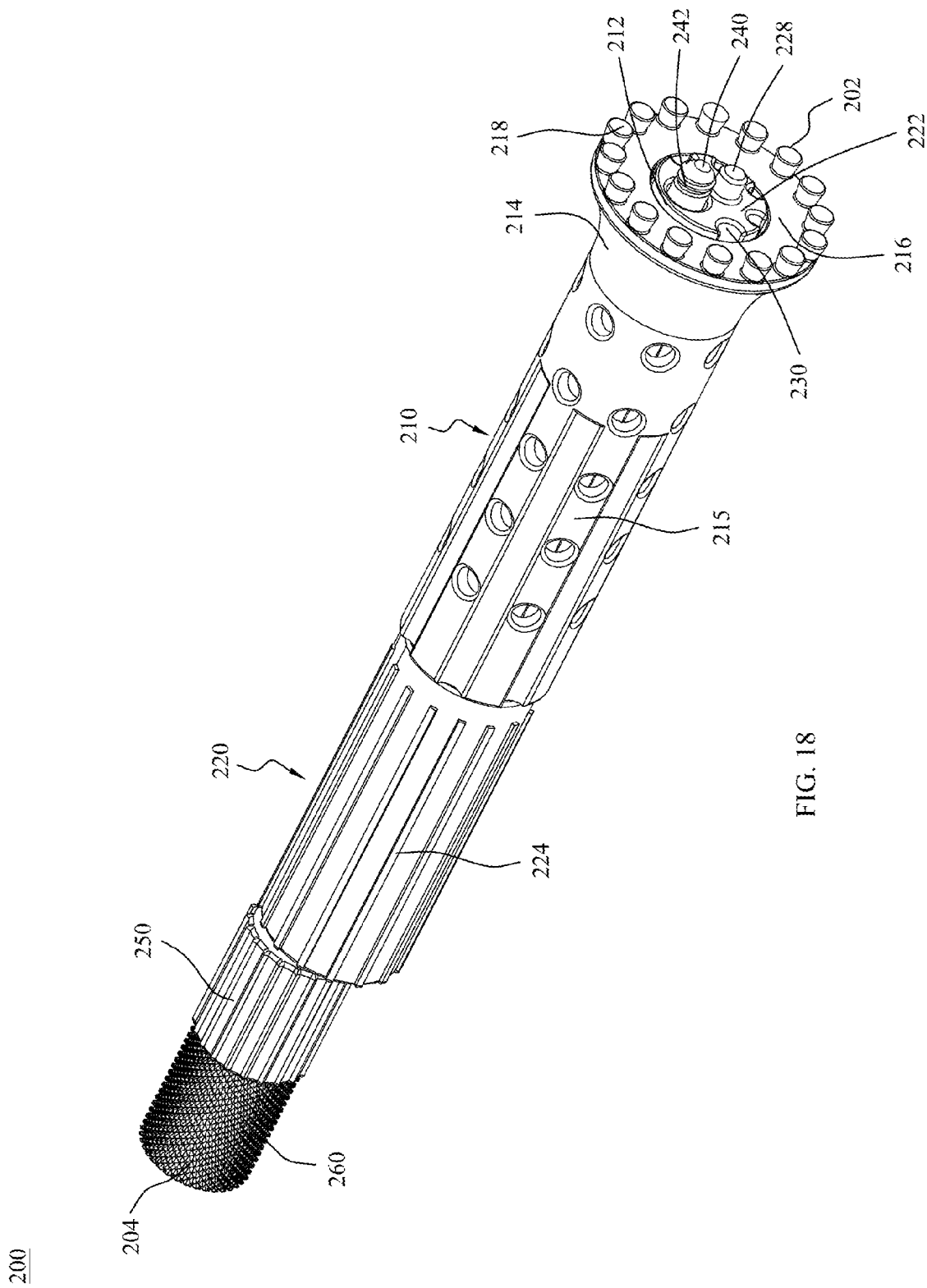
FIG. 18 is a perspective view of an insertion tool for the vertebral body device of FIG. 1, in accordance with an aspect of the present invention.
Figure 19:
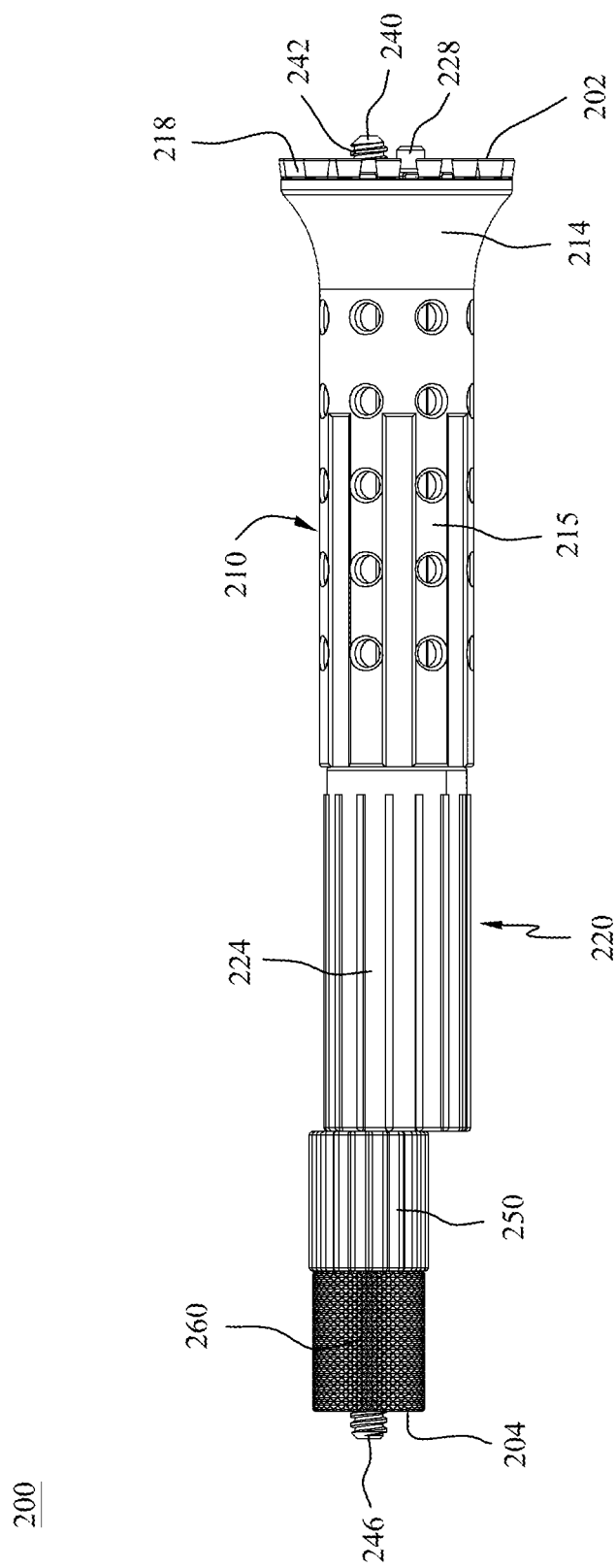
FIG. 19 is a side view of the insertion tool of FIG. 18, in accordance with an aspect of the present invention.

As shown in FIGS. 4-5 and 14-17, the first extension member 150 may include a first end 152 and a second end 154. The first extension member 150 may also include a top portion or first end cap 156 at the first end 152 and at least one leg member 162 extending away from the top portion 156 and to the second end 154. The top portion 156 may include a curved top surface 158, for example, a hemispherical or cylindrical shaped cup, and a center opening 160, as shown in FIGS. 5 and 15. The curved top surface 158 and center opening 160 may be configured to receive autologous bone graft or allograft material which will contact and allow for fusion with the adjacent vertebral bodies and additional graft material positioned between the at least one leg member 162. The curved surface 158 may be, for example, sized to allow the graft material to be positioned within the first extension member 150 to minimize the height. In addition, the hemispherical shaped cup may be selected, for example, to minimize the amount of graft material necessary to fill the curved surface 158. The top surface 158 may be, for example, coated, textured, porous, or of a trabecular metal nature to allow for bone growth into the first extension member 150 after implantation. In an alternative embodiment, it is also contemplated that the curved top surface 158 may be, for example, a mesh or open slotted top surface to allow for the bone graft material positioned in the top portion 156 to make contact with bone graft material positioned between the at least one leg member 162. The top portion 156 may also be configured to receive, for example, end caps (not shown) with lordosis or a larger footprint to contact larger adjacent vertebral bodies at the outer ring of their end plates.

The at least one leg member 162 may be, for example, three leg members 162. The leg members 162 may include threads 164 on an exterior surface and a tab 166 positioned at the second end 154 of the first extension member 150. The second end 154 of the leg members 162 may be, for example, tapered or angled and the tab 166 may be positioned at the tip of the tapered or angled end. The tabs 166 may be sized and shaped to engage the angled slots 138 on the interior surface of the first rotating member 130. As the tabs 166 are translated within the slots 138 of the first rotating member 130, the threads 164 of the leg members 162 engage the interior threads 136 of the first rotating member 130 to couple the first extension member 150 to the first rotating member 130. The leg members 162 may be curved to enable the leg members 162 to rotate with respect to the first rotating member 130. The first extension member 150 may also include support members 168 positioned between and connected to the leg members 162. The support members 168 may be, for example, cross-hatching braces positioned in rings. As depicted in FIGS. 14-17, the support members 168 may, for example, extend out from the back side of the leg members 162 and be connected between the leg members 162 in crisscross or "X" shaped arrangements. The crisscross arrangement of the leg members 162 may be, for example, curved between the leg members 162 to form a ring-like shape.

The second extension member 170, as shown in FIGS. 4 and 5, may include a first end 172 and a second end 174. The second extension member 170 may also include a bottom portion or second end cap 176 at the first end 172 and at least one leg member 182 extending away from the bottom portion 176 and to the second end 174. The bottom portion 176 may include a curved bottom surface 178 and an opening 180. The curved bottom surface 178 may be of the type described above with respect to the curved top surface 158, which will not be described again here for brevity's sake. The curved bottom surface 178 and center opening 180 may also be configured to receive autologous bone graft or allograft material as described in greater detail above with respect to the first extension member 150.

The at least one leg member 182 may be, for example, three leg members 182 and may include threads 184, tabs 186, and support members 188. The threads 184, tabs 186, and support members 188 may be of the type described above with reference to threads 164, tabs 166, and support members 168, which will not be described again here for brevity's sake. The tabs 186 may be sized and shaped to engage the angled slots 148 on the interior surface of the second rotating member 140. As the tabs 186 are translated within the slots 148 of the second rotating member 140, the threads 184 of the leg members 182 engage the interior threads 146 of the first rotating member 140 to couple the second extension member 170 to the second rotating member 140. The leg members 182 may be curved to enable the leg members 182 to rotate with respect to the second rotating member 140.

The vertebral body replacement device 100 may be assembled by obtaining a body 110 with a first rotating member 130 positioned in the first groove 120 and a second rotating member 140 positioned in the second groove 122. Next, the first and second extension members 150, 170 may be inserted into the channels 118 in the opening 116 of the body 110. The first extension member 150 may be inserted into the channels 118 from the first end 112. During insertion into the channels 118, the tabs 166 of the first extension member 150 may be aligned with the angled slots 138 on the interior surface of the first rotating member 130. The tabs 166 may be translated within the angled slots 138 by rotating the first extension member 150 until the threads 164 of the leg members 162 engage the interior threads 136 of the first rotating member 130. The first extension member 150 may be rotated until the member 150 engages the first end 112 of the body 110. Once the first extension member 150 is positioned in the body 110, then, the second extension member 170 may be inserted into the opening 116. The second extension member 170 may be inserted into the channels 119 from the second end 114. During insertion into the channels 119, the tabs 186 of the second extension member 170 may be aligned with the angled slots 148 on the interior surface of the second rotating member 140. The tabs 186 may be translated within the angled slots 148 by rotating the second extension member 170 until the threads 184 of the leg members 182 engage the interior threads 146 of the second rotating member 140. The second extension member 170 may be rotated until the member 170 engages the second end 114 of the body 110.

Referring now to FIGS. 18-23, an insertion instrument or inserter tool 200 is shown. The tool 200 includes a first end 202 and a second end 204. The tool 200 may include a deployment handle 210 at the first end 202, a position selector member 220 rotatably coupled to the handle 210, a rod 240 extending through the member 220, an implant attachment member 250 coupled to a portion of the rod 240, and a tension adjustment member 260 at the second end 204 and rotatably coupled to the rod 240.

Figure 22:
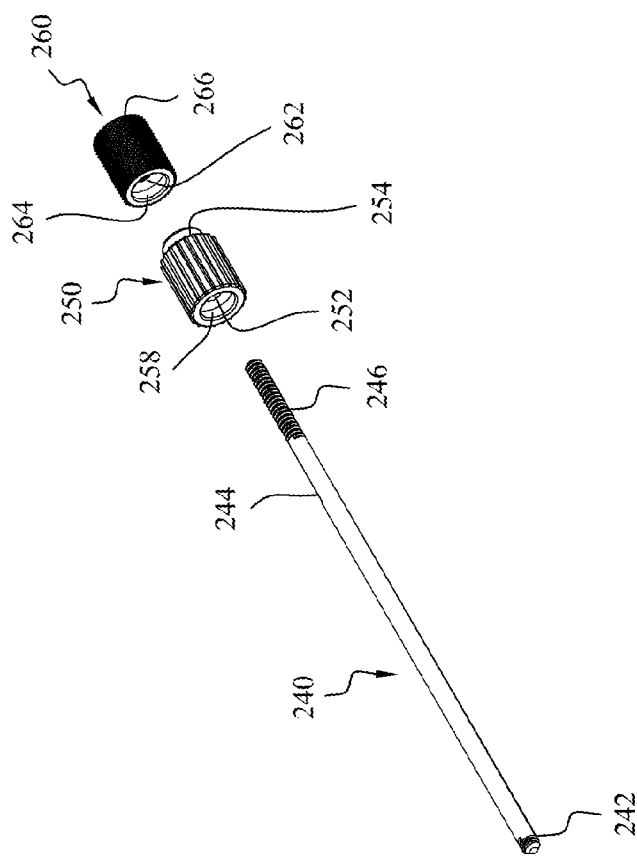
FIG. 22 is an exploded view of the insertion tool of FIG. 18 from a first end, in accordance with an aspect of the present invention.
Figure 22:
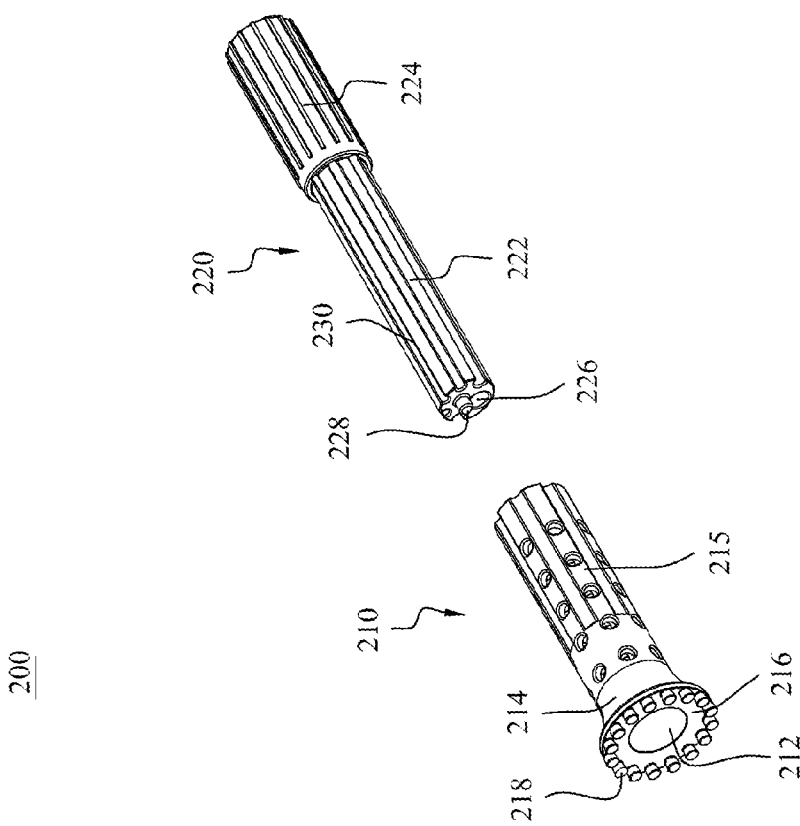
Figure 23:
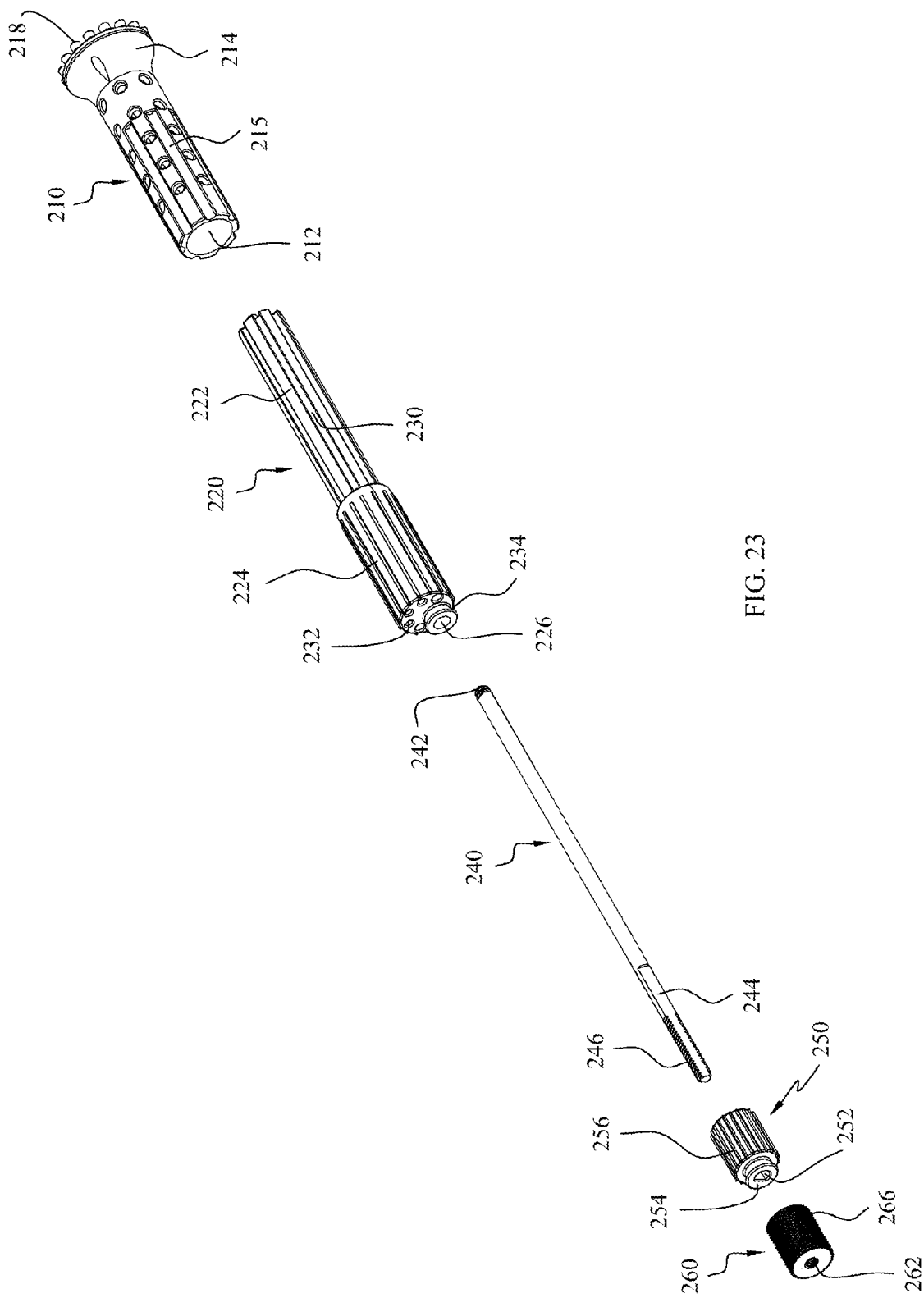
FIG. 23 is an exploded view of the insertion tool of FIG. 18 from a second end, in accordance with an aspect of the present invention.

As shown in FIGS. 22 and 23, the deployment handle 210 may include a passageway 212 extending along the longitudinal axis of the handle 210 from a first end to a second end. The handle 210 may also include a neck 214 near the first end. The neck 214 may, for example, increase the diameter of the handle from a body portion 215 to the engagement end 216. The engagement end 216 may include a plurality of projections 218 for engaging the grooves 132, 142 in the rotating members 130, 140. The plurality of projections 218 may be, for example, cone shaped or angled toward the point of attachment with the handle 210 to allow for the projections 218 to engage the grooves or teeth 132, 142 of the rotating members 130, 140. The teeth 132, 142 may have, for example, an undercut or angled shape to lock the plurality of projections 218 into the teeth 132, 142 and prevent jumping of the projections 218 with respect to the teeth 132, 142 as the handle 210 is rotated.

The position selector member 220 may include a first portion 222, a second portion 224, and an opening 226 extending through the entire member 220, as shown in FIGS. 22 and 23. The opening 226 may be offset from the center of the member 220 and extend in a longitudinal direction. The opening 226 may be configured to receive the rod 240. The first portion 222 may also have, for example, a smaller diameter than the second portion 224. The first portion 222 may be sized to fit in the passageway 212 of the handle 210. The first portion 222 may further include a pin 228 extending away from a first end of the first portion 222. The pin 228 may be shaped and sized to fit in the first and second positioning holes 126, 128 of a vertebral body device 100. In addition, the first portion 222 may include a plurality of grooves 230 positioned around the exterior surface. The second portion 224 may include a plurality of holes 232 extending through the second portion 224 in a longitudinal direction and aligning with the grooves 230 in the first portion 222. The second portion 224 may also include a flange 234 surrounding the opening 226. The flange 234 may be configured or sized and shaped to be received within the attachment member 250.

FIGS. 22 and 23 show the rod 240. The rod 240 includes a threaded section 242 at a first end and a cutout portion 244 and a threaded portion 246 at a second end. The threaded portion 246 may extend along the rod 240, for example, a shorter, the same, or a longer distance than the length of the cutout portion 244. The cutout portion 244 may be, for example, a flat or planar portion of the circular rod 240. The rod 240 may be inserted into the opening 226 in the position selector member 220 and extend out the first end 202 of the tool 200.

The implant attachment member 250, as shown in FIGS. 22 and 23, may include an opening 252 which may be shaped, for example, to receive the cutout portion 244. The opening 252 may include, for example, a planar portion and a circular portion to correspond to the planar section and circular section of the cutout portion 244 of the rod 240. The opening 252 may extend through the member 250 in a longitudinal direction. A flange 254 may be positioned around the opening 252 at a first end of the member 250. The second end of the member 250 may include a coupling cavity 258 recessed within the member 250. The cavity 258 may be sized to receive the flange 234 extending away from the position selector member 220 to rotatably couple the implant attachment member 250 to the position selector member 220. The attachment member 250 may also include a grooved exterior surface 256. The grooved surface 256 may, for example, assist the user with turning the member 250.

Referring to FIGS. 22 and 23, the tension adjustment member 260 includes an opening 262 extending through the member 260 in a longitudinal direction. The opening 262 may be threaded with threads corresponding to the threads 246 on the rod 240. As shown in FIG. 22, the adjustment member 260 may also include a coupling cavity 264 which is configured or sized and shaped to receive the flange 254 of the attachment member 250 to rotatably couple the attachment member 250 to the adjustment member 260. Further, the adjustment member 260 may have a textured surface 266 on the exterior of the adjustment member 260 to assist with rotation of the member 260 during use.

With continued reference to FIGS. 18-23, the inserter tool 200 may be assembled by inserting the first portion 222 of the position selector member 220 into the opening 212 in the handle 210. The position selector member 220 may be inserted with the pin 228 in a superior or inferior position. Next, the rod 240 may be inserted into the opening 226 in the second portion 224 of the position selector member 220. The opening 252 of the attachment member 250 may be aligned with the cutout portion 244 of the rod 240 and the attachment member 250 may be inserted over the rod 240. The attachment member 250 may be translated down the rod 240 until it engages the second portion 224 of the position selector member 220. Finally, the adjustment member 260 may be threaded onto the threads 246 of the rod 240 until the adjustment member 260 engages the attachment member 250.

Figure 24:
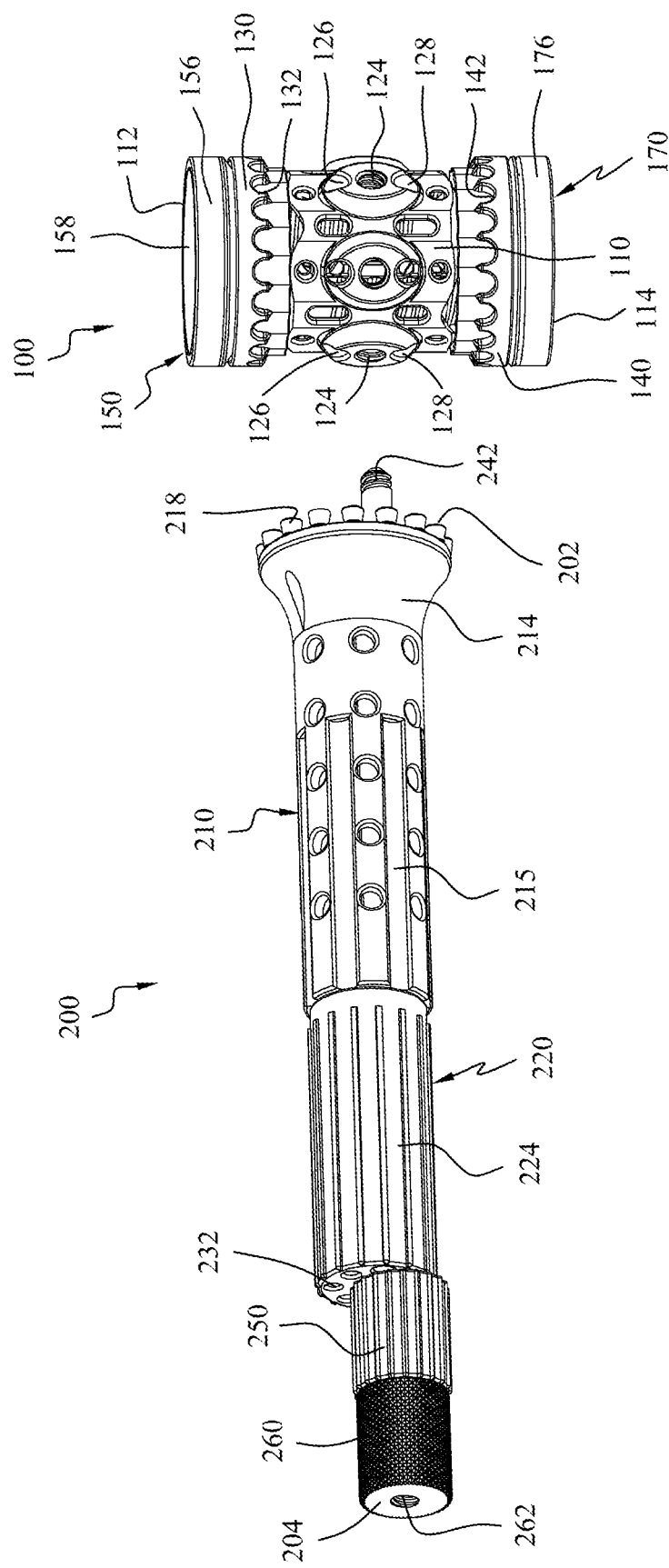
FIG. 24 is a perspective view of a vertebral body device system including the vertebral body device of FIG. 1 and the insertion tool of FIG. 18, in accordance with an aspect of the present invention.

Referring now to FIGS. 24-33 with continued reference to FIGS. 1-23, a method of using the vertebral body device 100 and insertion instrument 200 is shown. The method includes obtaining a vertebral body device 100 and an insertion instrument 200. The vertebral body 100 and insertion instrument 200 may be assembled as described in greater detail above, which will not be described again here for brevity's sake. The instrument 200 may then be coupled to the vertebral body device 100 by aligning the threaded section 242 of the rod 240 with one of the plurality of openings 124, as shown in FIG. 24.

Figure 20:
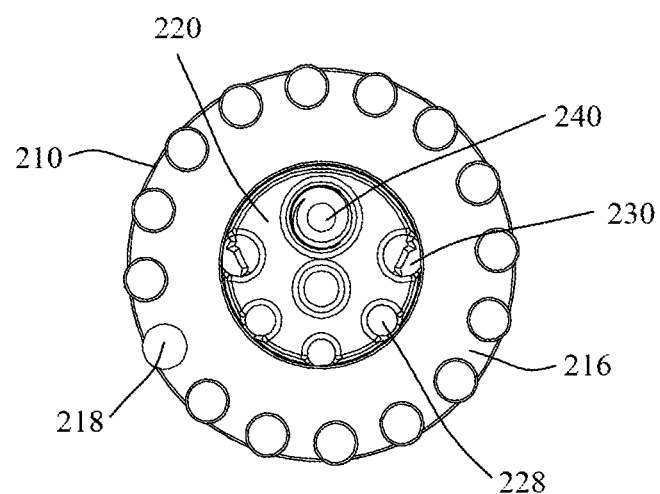
FIG. 20 is a front view of the insertion tool of FIG. 18 in a first position, in accordance with an aspect of the present invention.
Figure 21:
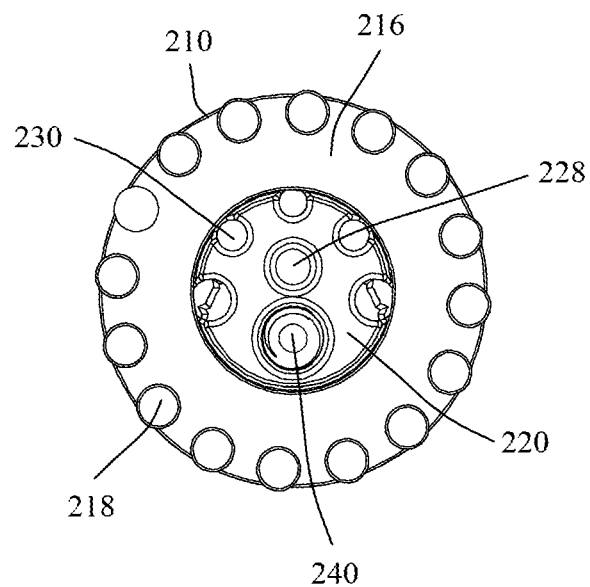
FIG. 21 is a front view of the insertion tool of FIG. 18 in a second position, in accordance with an aspect of the present invention.
Figure 25:
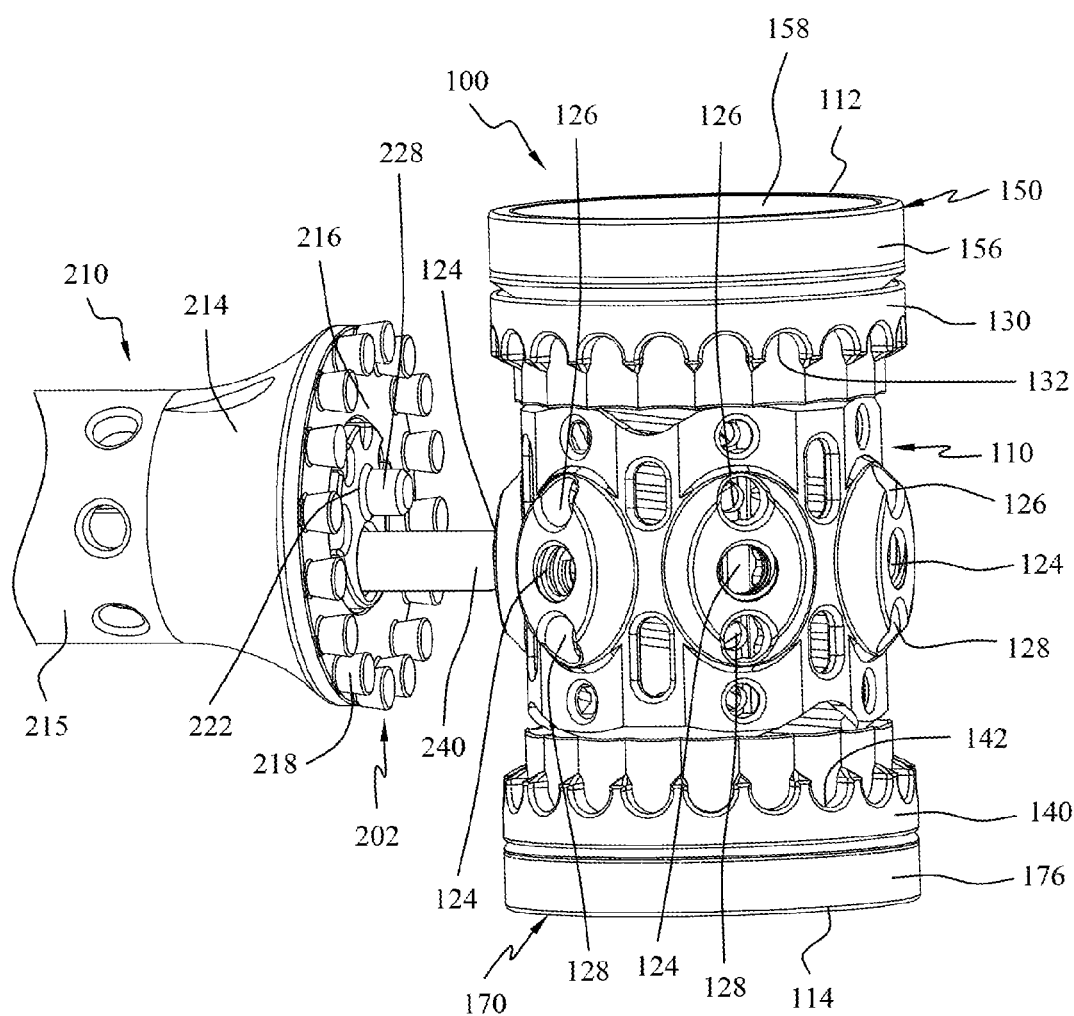
FIG. 25 is a perspective side view of a portion of the system of FIG. 24 with a rod of the tool engaging the vertebral body device, in accordance with an aspect of the present invention.
Figure 26:
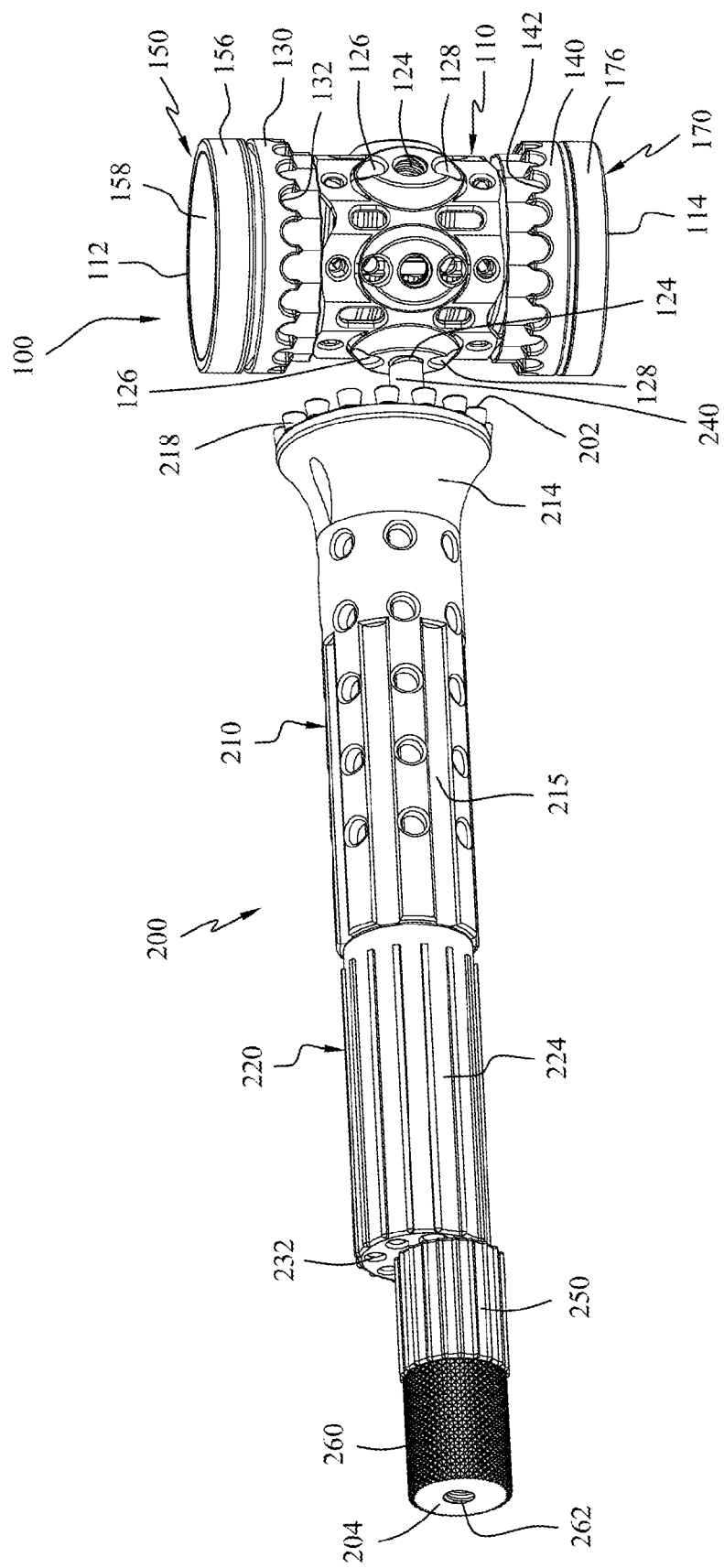
FIG. 26 is a perspective side view of the system of FIG. 24 with a rod of the tool engaging the vertebral body device, in accordance with an aspect of the present invention.
Figure 27:
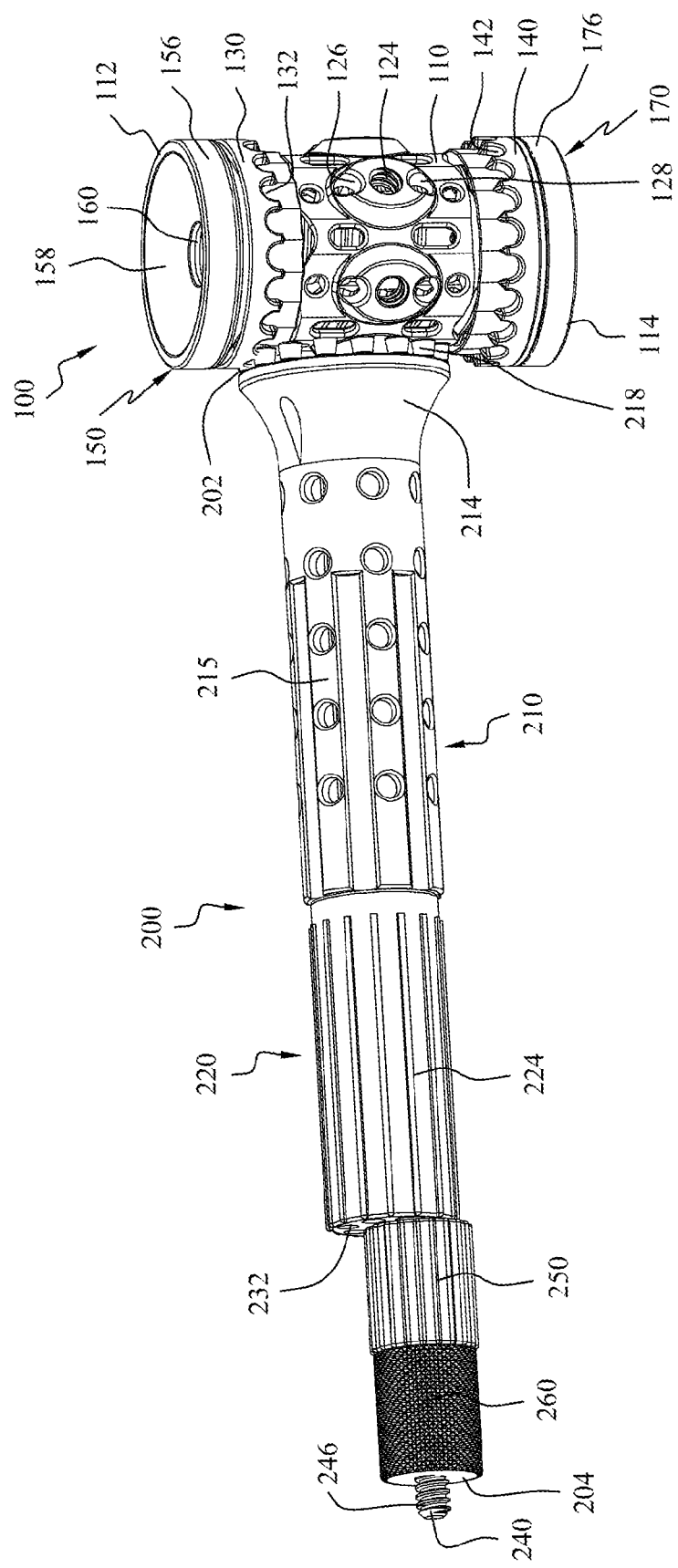
FIG. 27 is a perspective side view of the system of FIG. 24 with the tool engaging the vertebral body device in a first position, in accordance with an aspect of the present invention.
Figure 28:
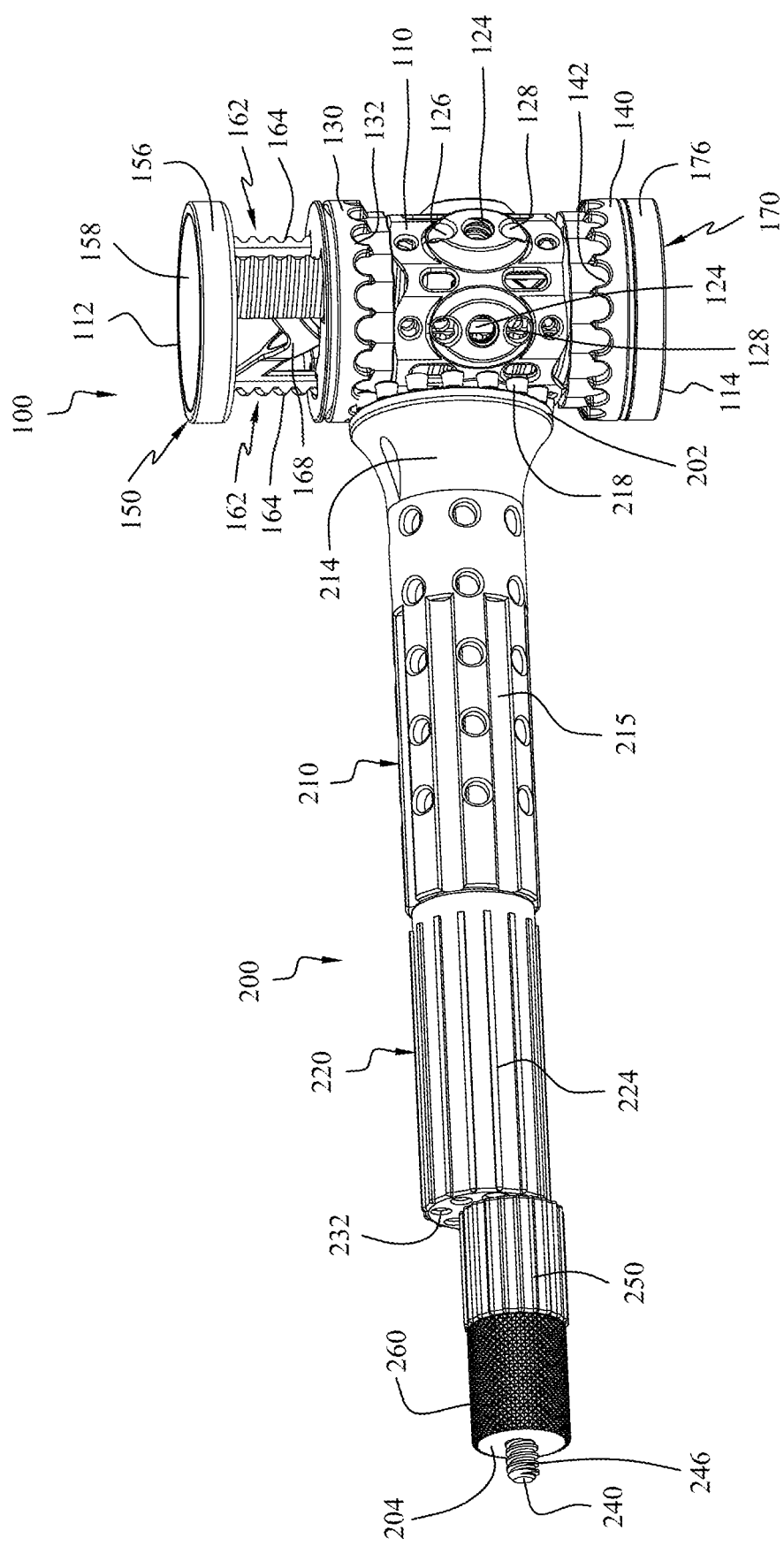
FIG. 28 is a perspective side view of the system of FIG. 24 with the first extension member in a deployed position, in accordance with an aspect of the present invention.

Once aligned the attachment member 250 may be rotated to turn the rod 240 and engage the threaded section 242 with the threads in the selected opening 124, as shown in FIGS. 25 and 26. The attachment member 250 may be, for example, rotated in a clockwise direction to engage the threaded opening 124. Next, the adjustment member 260 may be rotated to translate the deployment handle 210, the position selector member 220, the attachment member 250, and the adjustment member 260 toward the threaded section 242 of the rod 240. The adjustment member 260 translates by the threads in opening 262 engaging the threaded portion 242 of the rod 240. As the adjustment member 260 is rotated the pin 228 is also moved relative to the rod 240 to engage one of the first positioning holes 126 or one of the second positioning holes 128. The pin 228 is shown positioned in a first positioning hole 126 in FIG. 27. FIG. 21 illustrates the pin 228 in a position to engage one of the first positioning holes 126 and FIG. 20 illustrates the pin 228 in a position to engage one of the second positioning holes 128. In addition, as adjustment member 260 is rotated, the plurality of projections 218 on the handle 210 are moved into engagement with the plurality of grooves 132, 142 on the first or second rotating member 130, 140. As shown in FIG. 28, the plurality of projections 218 engage the grooves 132 on the first rotating member 130.

After the pin 228 is positioned in a first positioning hole 126 and projections 218 are positioned in the grooves 132 of the first rotating member 130, the handle 210 may be rotated. As the handle 210 is rotated the projections 218 engage the grooves 132 to rotate the first rotating member 130. As the first rotating member 130 spins, the first extension member 150 may translate in a superior-inferior direction. As shown in FIG. 28, if the handle 210 is rotated in a clockwise direction, the rotating member 130 will spin in a counterclockwise direction, and the first extension member 150 will translate in a superior direction increasing the height of the vertebral body device 100. Alternatively, if the handle 210 is rotated in a counterclockwise direction, the rotating member 130 will spin in a clockwise direction, and the first extension member 150 will translate in an inferior direction decreasing the height of the vertebral body device 100. The amount of superior-inferior translation is limited by the length of the leg members 162.

Figure 29:
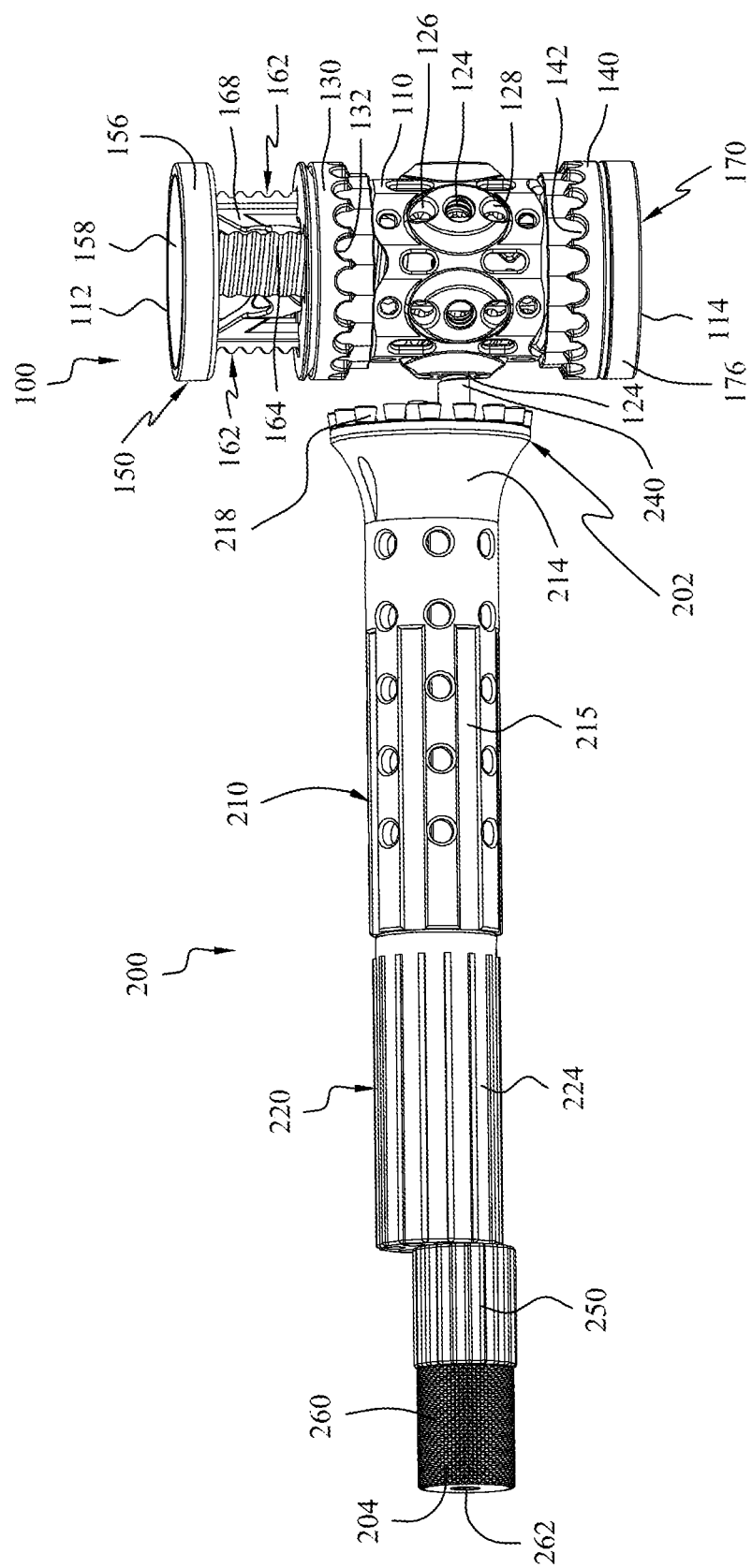
FIG. 29 is a perspective side view of the system of FIG. 24 with the rod of the tool engaging the vertebral body device in a first position, in accordance with an aspect of the present invention.
Figure 30:
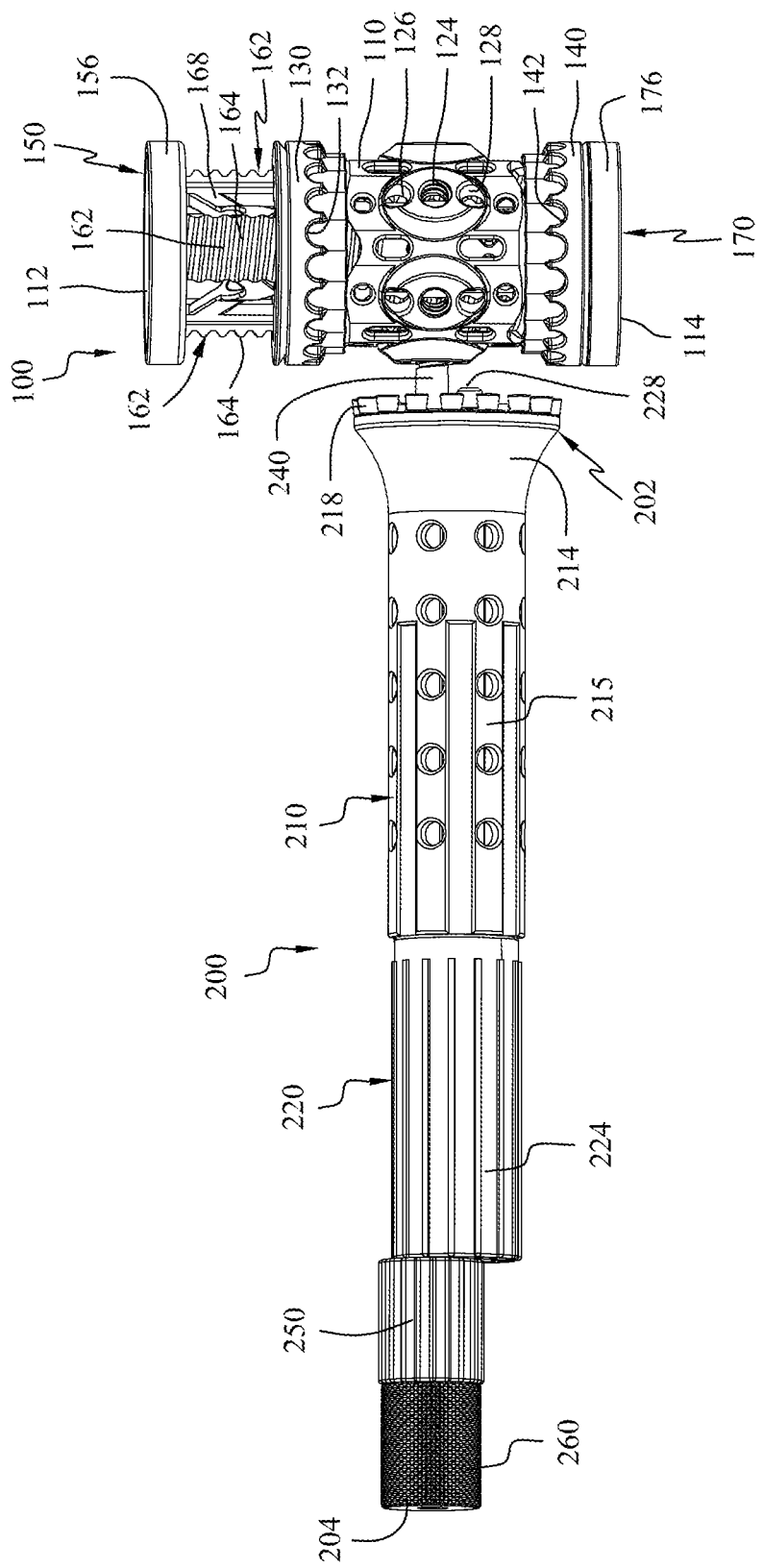
FIG. 30 is a perspective side view of the system of FIG. 24 with the rod of the tool engaging the vertebral body device in a second position, in accordance with an aspect of the present invention.

Once the first extension member 150 is deployed to a desired position, the adjustment member 260 may be rotated in, for example, a counterclockwise direction to disengage the projections 218 from the grooves 132 and the pin 228 from the first positioning hole 126, as shown in FIG. 29. Next, the second extension member 170 may be deployed to a desired position. To deploy the second extension member 170, the position of the pin 228 may be moved to an inferior position. The pin 228 may be moved by holding the attachment member 250 and simultaneously rotating the position selector member 220 to rotate the pin 228 to an inferior position, as shown in FIG. 30. The position selector member 220 may be rotated in a counterclockwise direction to rotate the pin 228 from a superior position to an inferior position and vice versa. The pin 228 may be rotated until it is aligned with one of the second positioning holes 128.

Figure 31:
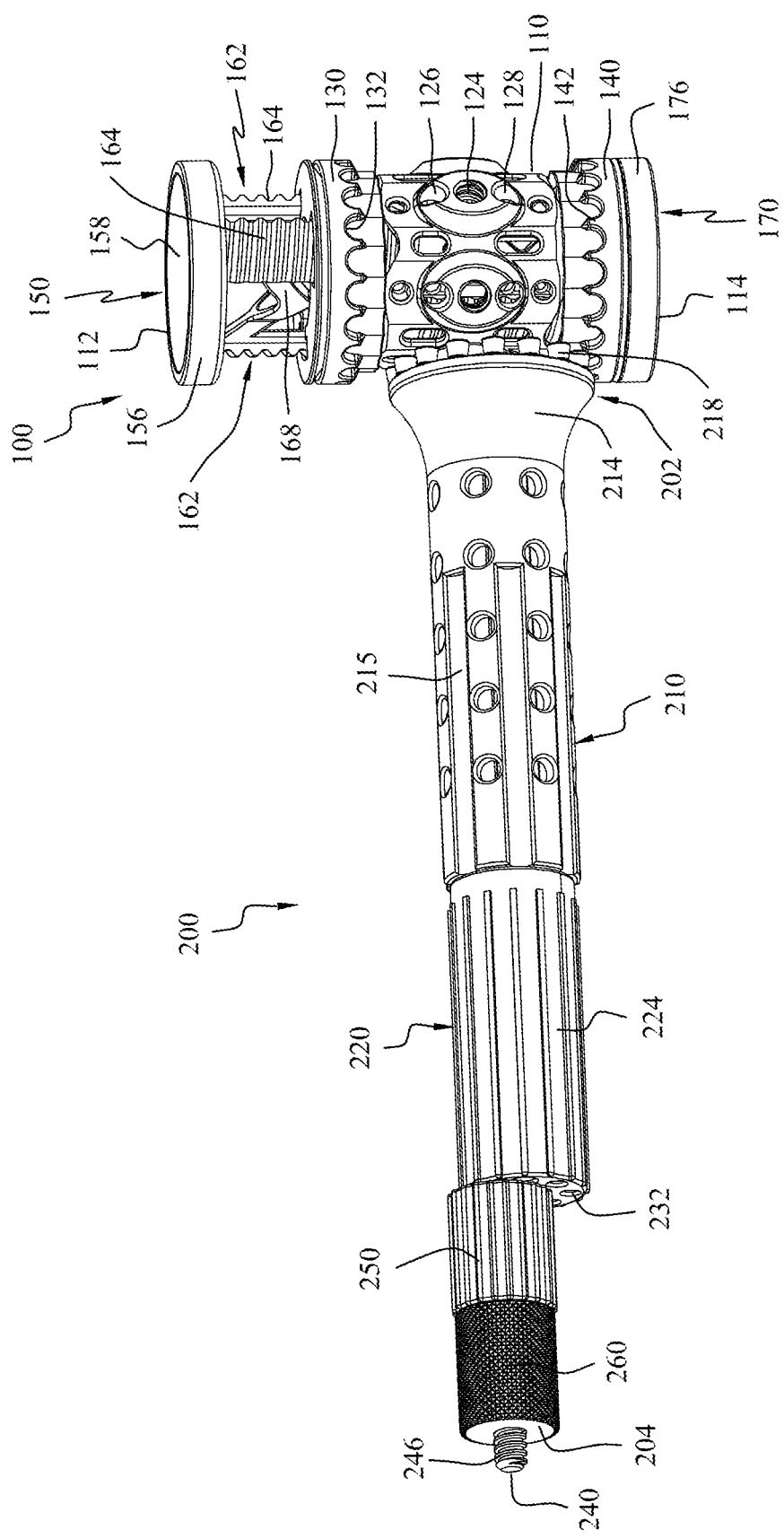
FIG. 31 is a perspective side view of the system of FIG. 24 with the tool engaging the vertebral body device in a second position, in accordance with an aspect of the present invention.
Figure 32:
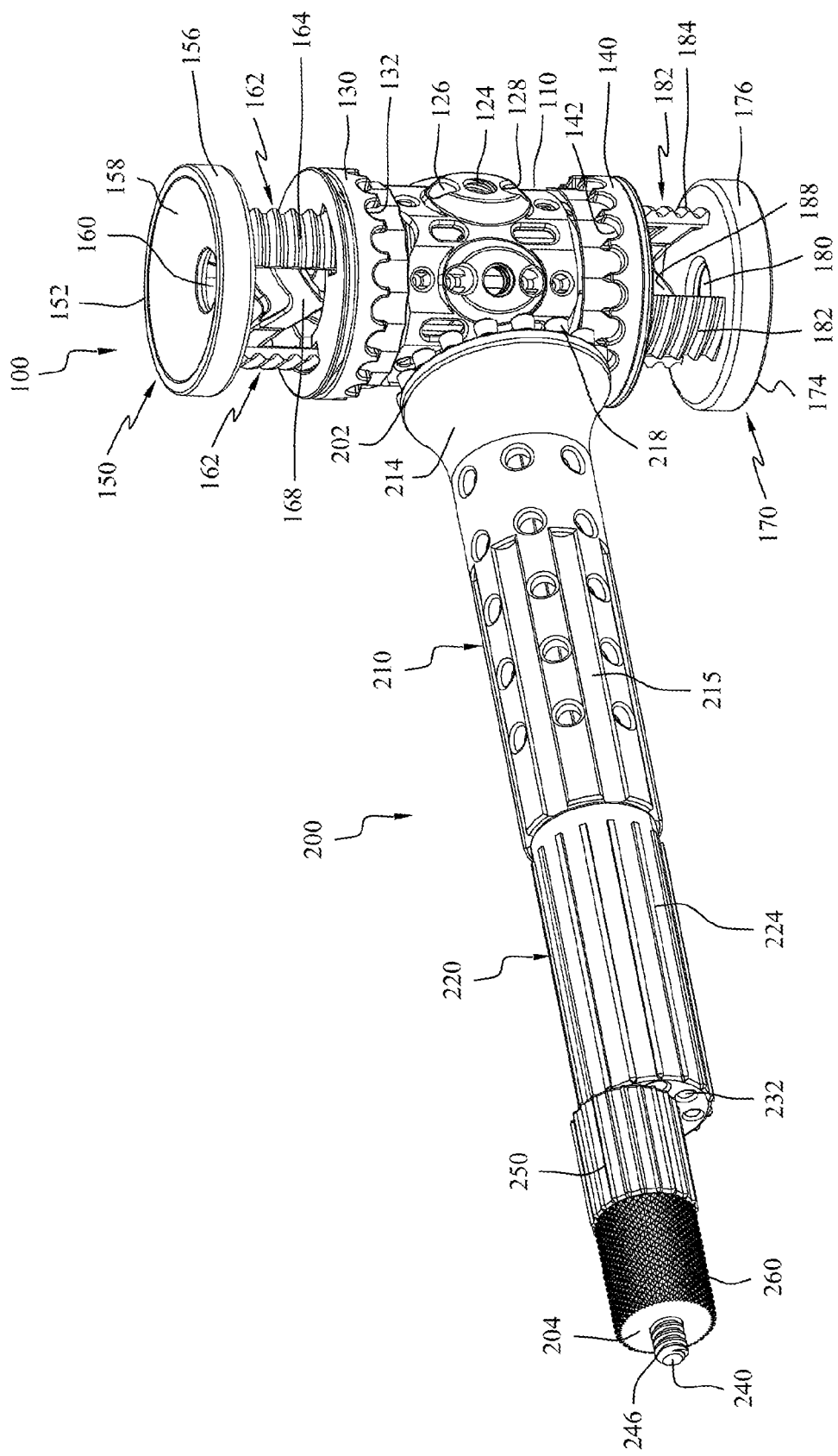
FIG. 32 is a perspective side view of the system of FIG. 24 with the second extension member in a deployed position, in accordance with an aspect of the present invention.
Figure 33:
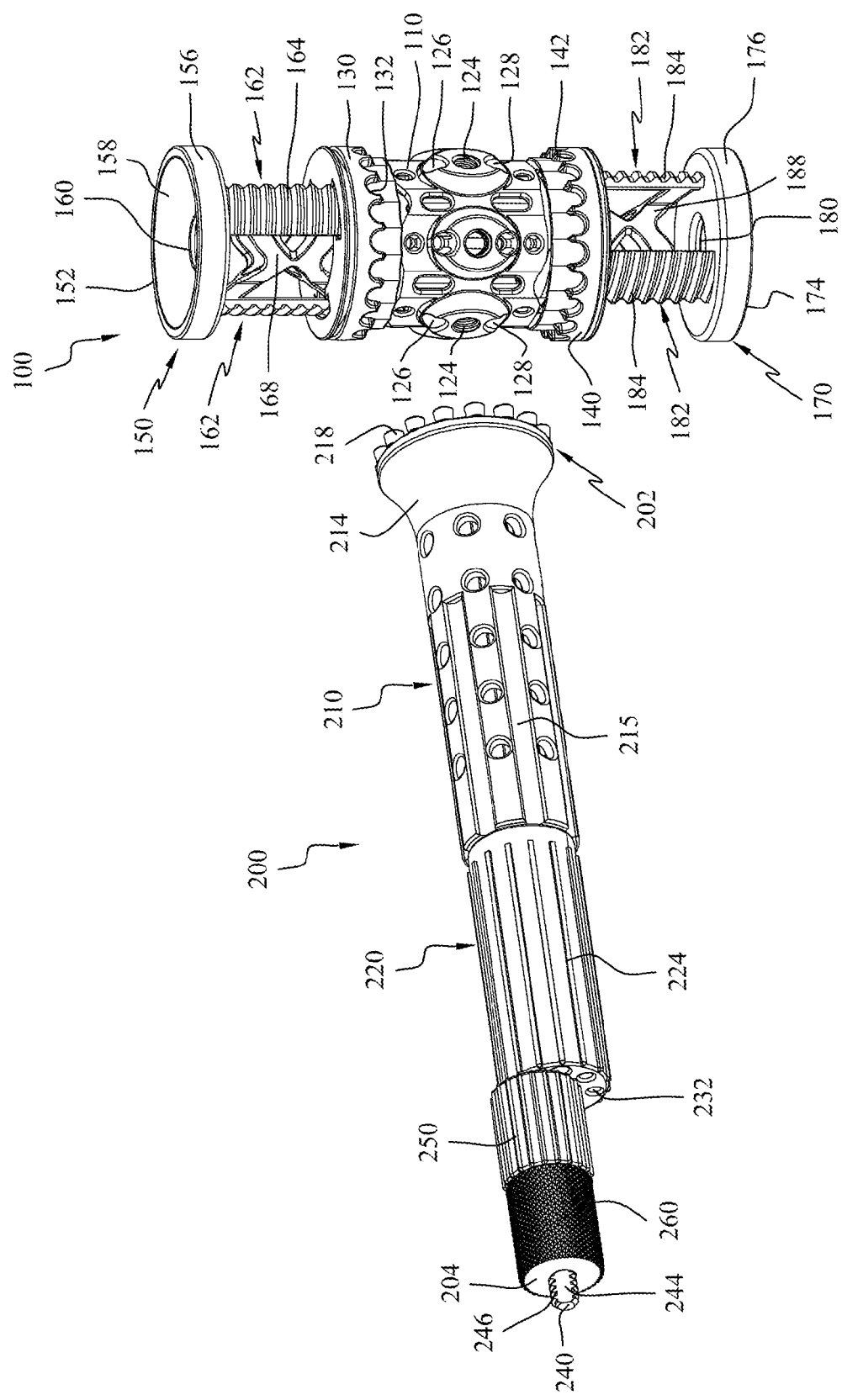
FIG. 33 is a perspective side view of the system of FIG. 24 with the tool removed from the expanded vertebral body device, in accordance with an aspect of the present invention.

Next, the adjustment member 260 may be rotated to again translate the deployment handle 210, the position selector member 220, the attachment member 250, and the adjustment member 260 toward the threaded section 242 of the rod 240. The adjustment member 260 may be rotated until the pin 228 engages a second positioning hole 128 and the projections 218 engage the grooves 142 in the second rotating member 140, as shown in FIG. 31. The handle 210 may then be rotated to engage the projections 218 in the grooves 132 causing the second rotating member 140 to turn. As the second rotating member 140 spins, the second extension member 170 may translate in a superior-inferior direction. As shown in FIG. 32, if the handle 210 is rotated in a clockwise direction, the rotating member 140 will spin in a clockwise direction, and the second extension member 170 will translate in an inferior direction increasing the height of the vertebral body device 100. Alternatively, if the handle 210 is rotated in a counterclockwise direction, the rotating member 140 will spin in a counterclockwise direction, and the second extension member 170 will translate in a superior direction decreasing the height of the vertebral body device 100. The amount of superior-inferior translation is limited by the length of the leg members 182. Once the desired configuration and height of the vertebral body device 100 is achieved, the attachment member 250 may be rotated to disengage the thread section 242 from the opening 124. After the rod 240 is removed from the vertebral body device 100, the instrument 200 may be removed from the implant 100, as shown in FIG. 33.

Figure 34:
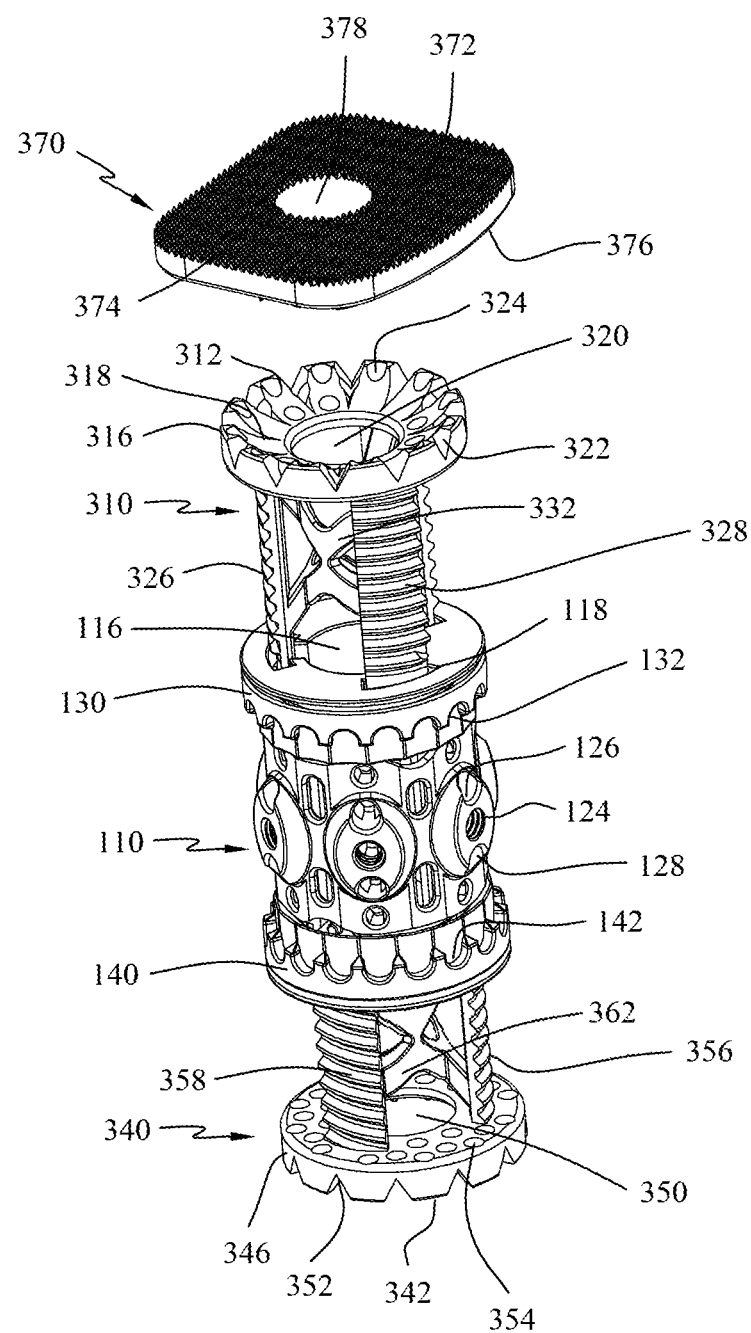
FIG. 34 is a partially exploded, perspective top view of another vertebral body device, in accordance with an aspect of the present invention.
Figure 35:
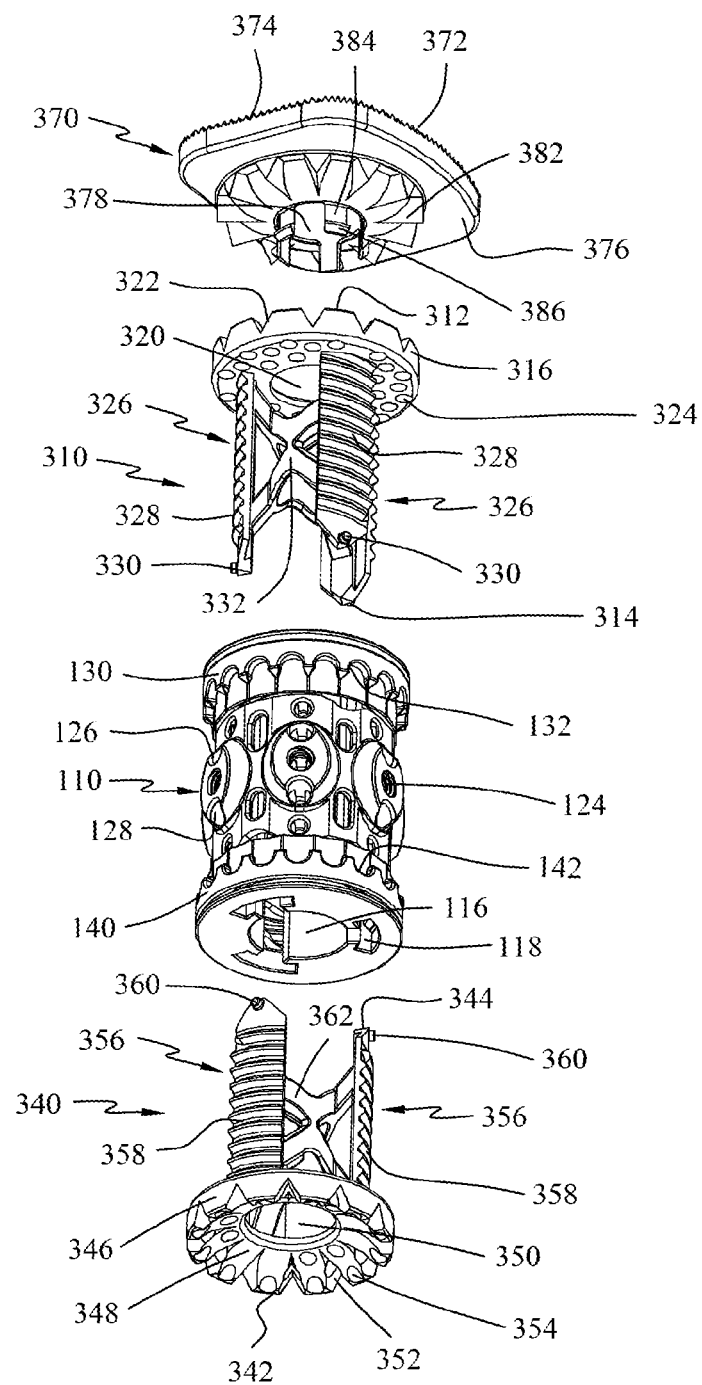
FIG. 35 is a partially exploded, perspective bottom view of the vertebral body device of FIG. 34, in accordance with an aspect of the present invention.
Figure 36:
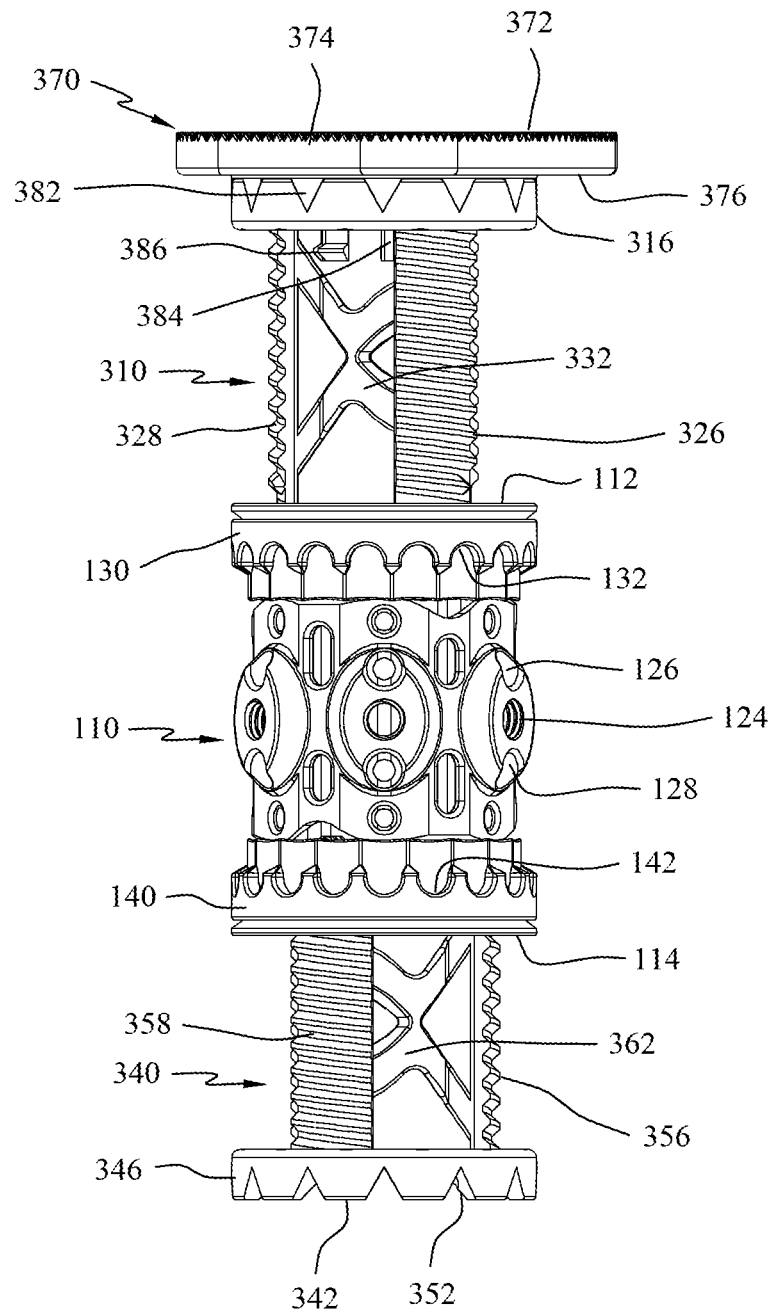
FIG. 36 is an assembled, side view of the vertebral body device of FIG. 34, in accordance with an aspect of the present invention.
Figure 37:
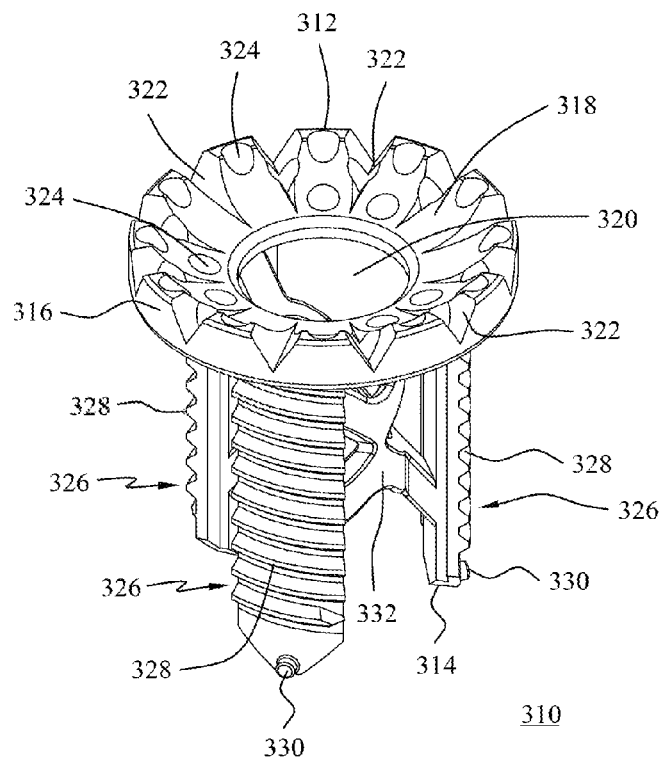
FIG. 37 is a perspective top view of a first extension member of the vertebral body device of FIG. 34, in accordance with an aspect of the present invention.
Figure 38:
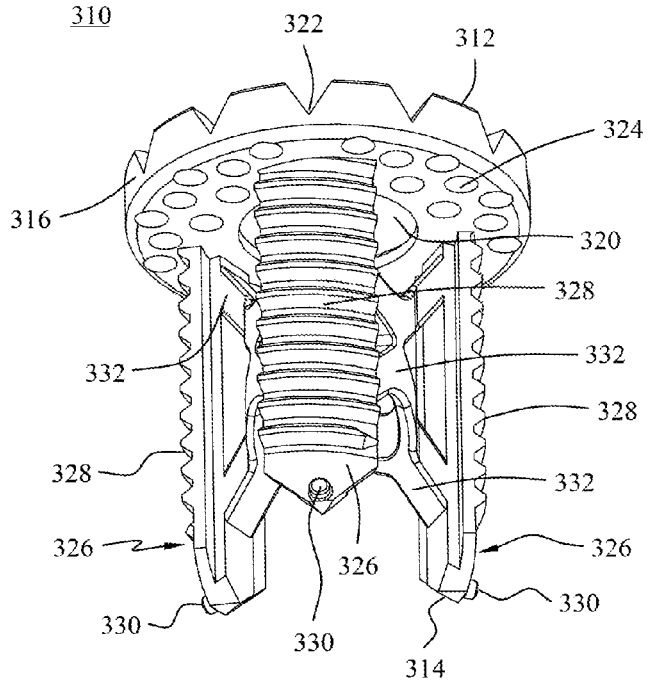
FIG. 38 is a perspective bottom view of the first extension member of FIG. 37, in accordance with an aspect of the present invention.

Another expandable vertebral body replacement device 300 is shown in FIGS. 34-36. The device 300 includes a body 110, a first rotating member 130, a second rotating member 140, a first extension member 310, a second extension member 340, and an end cap 370. The body 110, first rotating member 130, and second rotating member 140 are as described above with reference to FIGS. 1-13, which will not be described again here for brevity's sake. The first extension member 310 is shown in FIGS. 35, 37, and 38. The first extension member 310 includes a first end 312 and a second end 314. The first extension member 310 may also include a top portion 316 at the first end 312 and at least one leg member 326 extending away from the top portion 316 and to the second end 314. The top portion 316 may include a curved top surface 318, for example, a hemispherical or cylindrical shaped cup. The top portion 316 may also include a center opening 320, a plurality of grooves 322, and a plurality of openings 324. The plurality of grooves 322 may be, for example, inset into the top surface 318 and surrounding the center opening 320. The plurality of openings 324 may, for example, extend through the top portion 316 from the top surface 318 entirely through the top portion 316 and may surround the center opening 320. The top surface 318 and center opening 320 may be, for example, configured to receive an end cap 370 with lordosis or a larger footprint to contact larger adjacent vertebral bodies at the outer ring of their end plates. The center opening 320 may also be configured to receive autologous bone graft or allograft material which will contact and allow for fusion with the adjacent vertebral bodies and additional graft material positioned between the at least one leg member 326.

The at least one leg member 326 may be, for example, three leg members 326, as shown in FIGS. 35, 37, and 38. The leg members 326 may include threads 328 on an exterior surface, a tab 330 on each leg member 326 positioned at the second end 314 of the first extension member 310, and support members 332 positioned between and connected to the leg members 326. The leg members 326 may be of the type described above with respect to leg members 162, 182, which will not be described again here for brevity's sake.

The second extension member 340 is similar to the first extension member 310 of FIGS. 37 and 38. As shown in FIG. 35, the second extension member 340 may include a first end 342 and a second end 344. The second extension member 340 may also include a bottom portion 346 at the first end 342 and at least one leg member 356 extending away from the bottom portion 346 and to the second end 344. The bottom portion 346 may include a curved bottom surface 348, for example, a hemispherical or cylindrical shaped cup. The bottom portion 346 may also include a center opening 350, a plurality of grooves 352, and a plurality of openings 354. The plurality of grooves 352 may be, for example, inset into the bottom surface 348 and surrounding the center opening 350. The plurality of openings 354 may, for example, extend through the bottom portion 346 from the bottom surface 348 entirely through the bottom portion 346 and may surround the center opening 350. The bottom surface 348 and center opening 350 may be, for example, configured to receive an end cap 370 with lordosis or a larger footprint to contact larger adjacent vertebral bodies at the outer ring of their end plates. The center opening 350 may also be configured to receive autologous bone graft or allograft material which will contact and allow for fusion with the adjacent vertebral bodies and additional graft material positioned between the at least one leg member 356.

The at least one leg member 356 may be, for example, three leg members 356. The leg members 356 may include threads 358 on an exterior surface, a tab 360 on each leg member 356 positioned at the second end 344 of the second extension member 340, and support members 362 positioned between and connected to the leg members 356. The leg members 356 may be of the type described above with respect to leg members 162, 182, which will not be described again here for brevity's sake.

Figure 39:
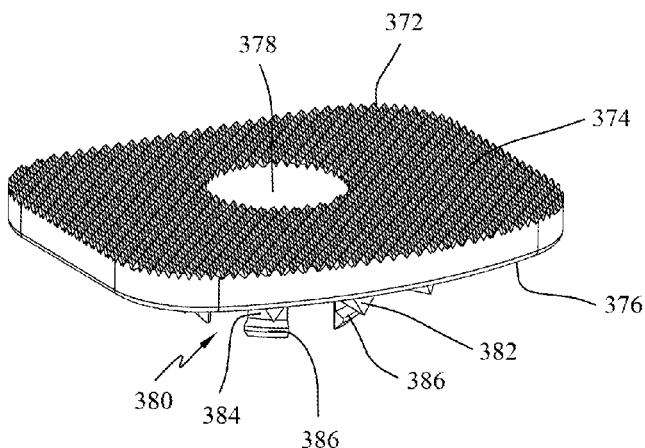
FIG. 39 is a perspective top view of an end cap of the vertebral body device of FIG. 34, in accordance with an aspect of the present invention.
Figure 40:
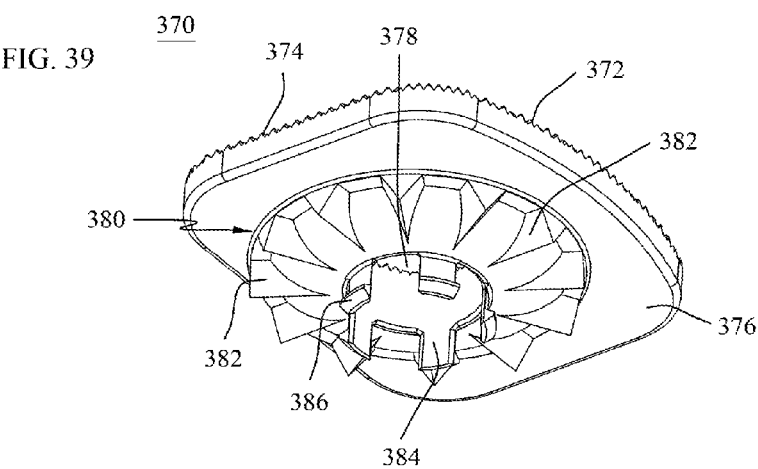
FIG. 40 is a perspective bottom view of the end cap of FIG. 39, in accordance with an aspect of the present invention.
Figure 41:
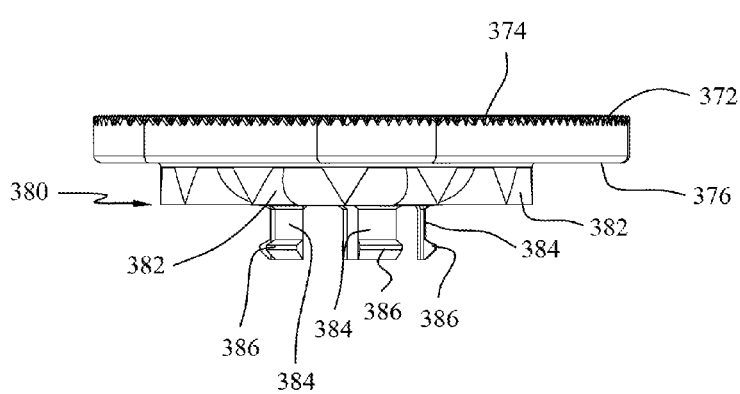
FIG. 41 is a side view of the end cap of FIG. 39, in accordance with an aspect of the present invention.
Figure 42:
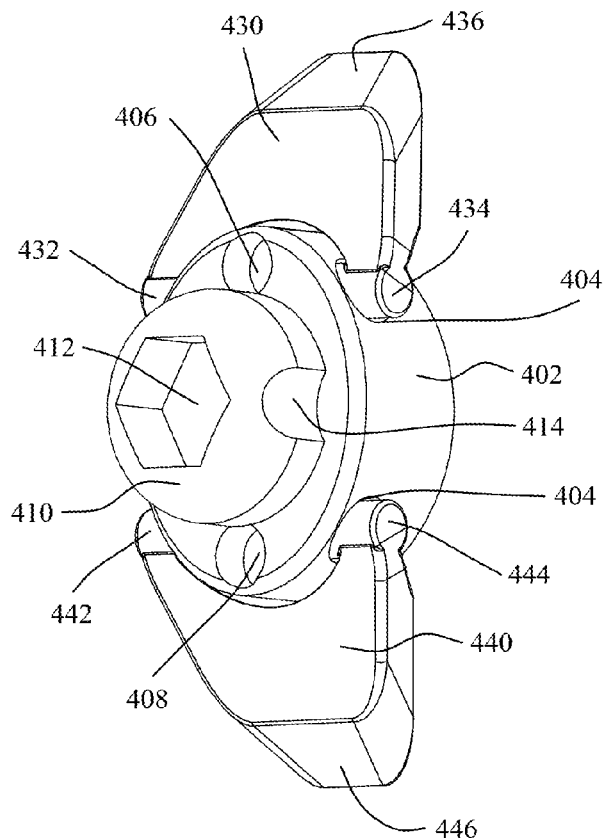
FIG. 42 is a perspective side view of a first locking member, in accordance with an aspect of the present invention.
Figure 43:
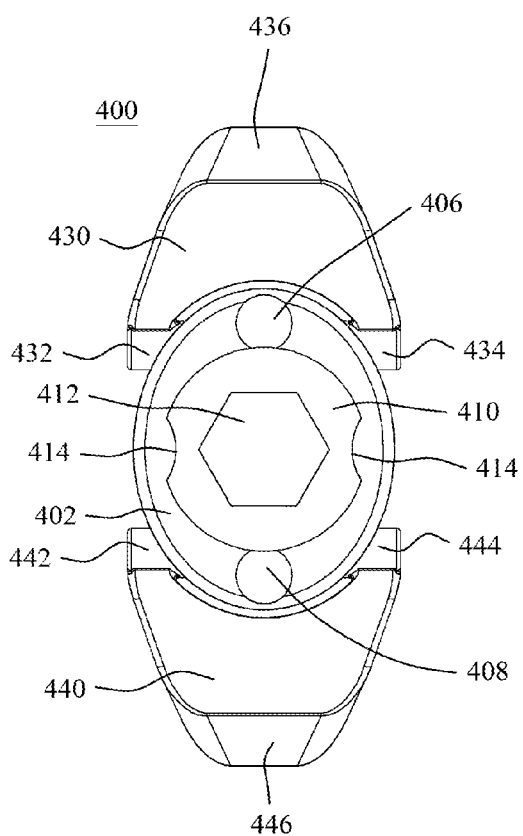
FIG. 43 is a front view of the first locking member of FIG. 42, in accordance with an aspect of the present invention.
Figure 44:
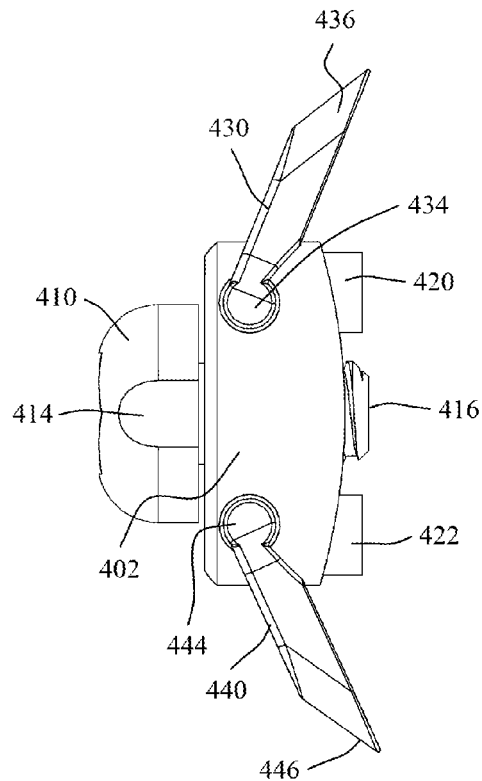
FIG. 44 is a side view of the first locking member of FIG. 42, in accordance with an aspect of the present invention.
Figure 45:
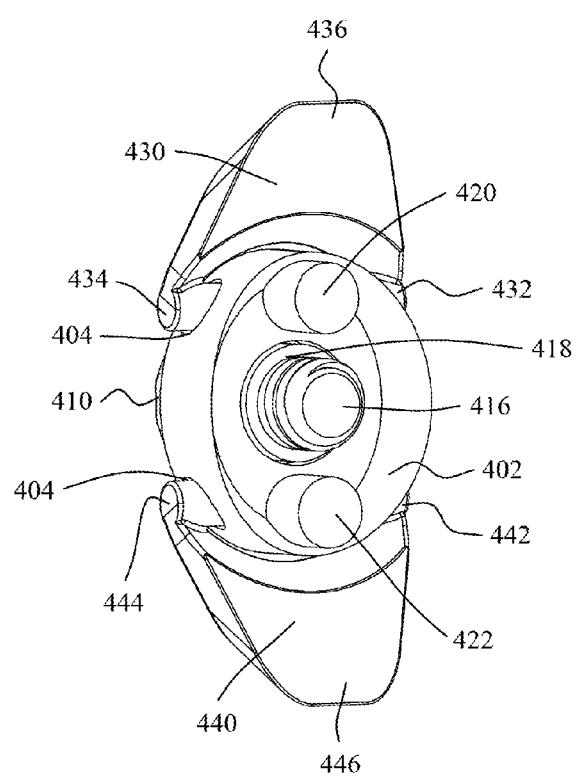
FIG. 45 is a perspective back view of the first locking member of FIG. 42, in accordance with an aspect of the present invention.
Figure 46:
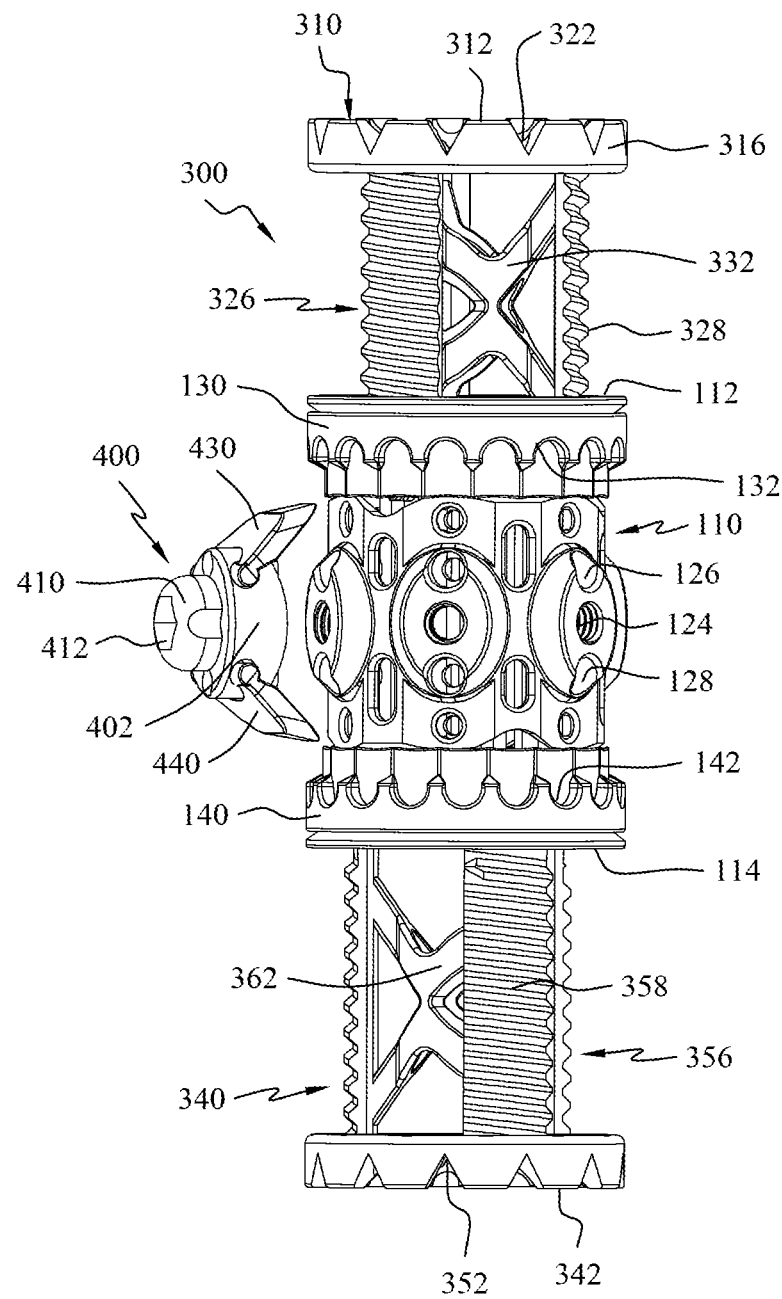
FIG. 46 is a partially exploded, perspective side view of a vertebral body device and the locking member of FIG. 42, in accordance with an aspect of the present invention.

As shown in FIGS. 39-41, the end cap 370 may include a top surface 372, a bottom surface 376, and an opening 378 extending through the end cap 370 from the top surface 372 to the bottom surface 376. The top surface 372 may have a textured surface 374, for example, grooves, teeth, ridges, or another coated, textured, or porous surface. The end cap 370 may also include an engagement portion 380 extending away from the bottom surface 376 and configured to engage at least one of the first and second extension members 310, 340. The engagement portion 380 may include teeth 382 positioned around the opening 378 and sized to fit into the grooves 322, 352 of the first and second extension members 310, 340. The engagement portion 380 may also include at least one engagement member 384 extending away from the bottom surface 376. The at least one engagement member 384 may be coupled to the bottom edge of the opening 378 at a first end. The at least one engagement member 384 may be, for example, five engagement members 384 as shown in FIGS. 35 and 40. Although alternative numbers of engagement members 384 are also contemplated. The engagement members 384 may be positioned, for example, circumferentially around the opening 378 and be sized to fit into the openings 320, 350 of the first and second extension members 310, 340. Each engagement member 384 may include a projection 386 at the second end extending away from the opening 378. The projections 386 may be sized and shaped to engage the top portion 316 of the first extension member 310 or the bottom portion 346 of the second extension member 340. The projections 386 may engage a bottom surface of the top portion 316 of the first extension member 310 and/or a top surface the bottom portion 346 of the second extension member 340 to secure the end cap 370 to at least one of the first extension member 310 and second extension member 340. Although the end cap 370 is shown with a relatively rectangular shape, the end cap 370 may have any shape desired to correspond to the shape of the vertebral body being contacted by the end cap 370.

The vertebral body replacement device 300 may be assembled as described in greater detail above with respect to vertebral body replacement device 100 and which will not be described again here for brevity's sake. Assembly of the device 300 may also include inserting the engagement members 384 of the end cap 370 into the opening 320, 350 of at least one of the first and second extension members 310, 340. The method of using the device 300 may be the same or similar to the method of using the device 100 and may include use of the insertion instrument 200, as described in greater detail above and which will not be described again here for brevity's sake.

The expandable vertebral body replacement devices 100, 300 may also include a locking member, for example, locking member 400 shown in FIGS. 42-49 or locking member 450 shown in FIGS. 50-56. As shown in FIGS. 42-45, the locking member 400 may include a base 402 with at least one opening 404 positioned on a side of the base and a first recess 406 and a second recess 408 positioned on the front of the base 402. The at least one opening 404 may be, for example, four openings 404 with two openings 404 positioned on opposite sides, near a top of the base 402 and two openings 404 positioned on opposite sides, near a bottom of the base 402. The base 402 may also include a hole 418 for receiving a coupling member 410. The first recess 406 may be positioned above the hole 418 and the second recess 408 may be positioned below the hole 418. The recesses 406, 408 may be sized to engage an instrument for inserting the locking member 400 into the patient to engage an expandable vertebral body replacement device 100, 300. The coupling member 410 may include a tool opening 412 positioned on the front, at least one cutout 414 on the side, and an engagement member 416 extending away from a back side. The engagement member 416 may be, for example, threaded to couple to the threads in the insertion tool opening 124 of the body 110 of the devices 100, 300. The tool opening 412 may be sized to receive a tool to rotate the coupling member 410 to insert the engagement member 416 into the opening 124 to secure the locking member 400 to the body 110. The base 402 may also include a first alignment projection 420 extending away from a back side of the base 402 and a second alignment projection 422 extending away from the back side of the base 402. The first alignment projection 420 may be positioned above the hole 418 and the second alignment projection 422 may be positioned below the hole 418. The first alignment projection 420 may be positioned to engage a first positioning hole 126 and the second alignment projection 422 may be positioned to engage a second positioning hole 128 or vice versa.

Figure 47:
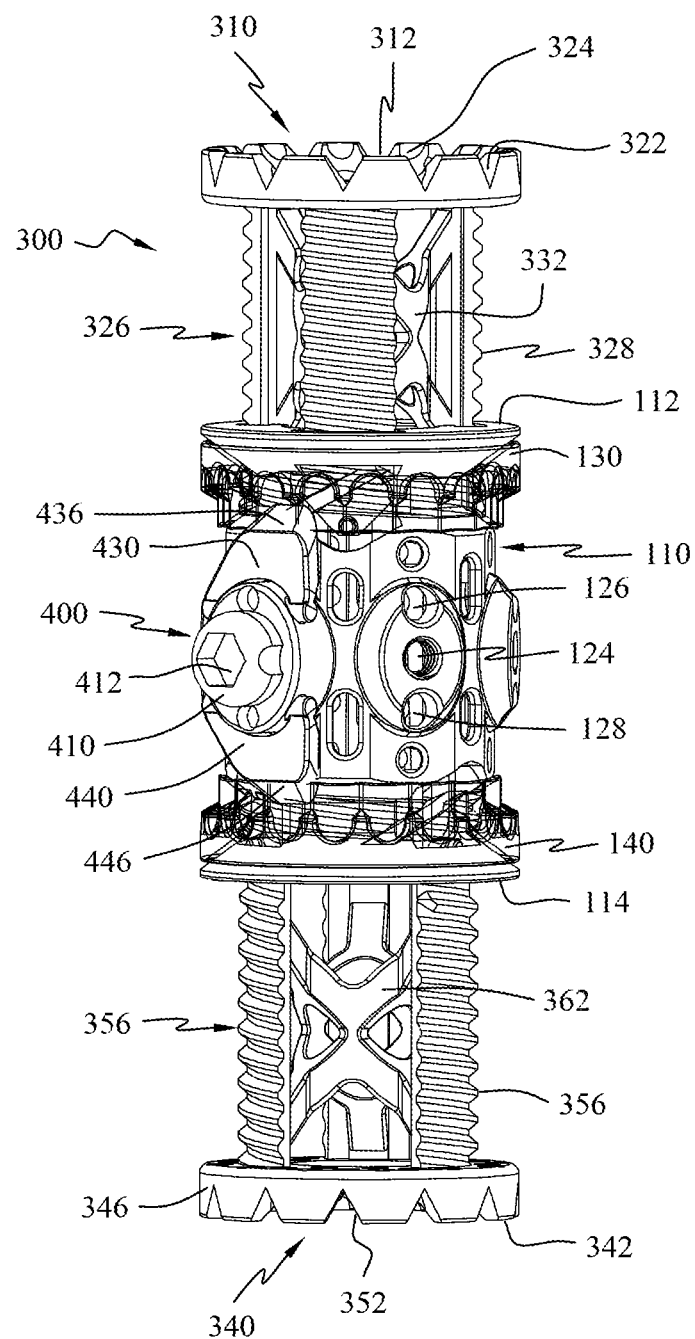
FIG. 47 is an assembled, perspective side view of the vertebral body device and locking member of FIG. 46 with transparent rotating members, in accordance with an aspect of the present invention.
Figure 48:
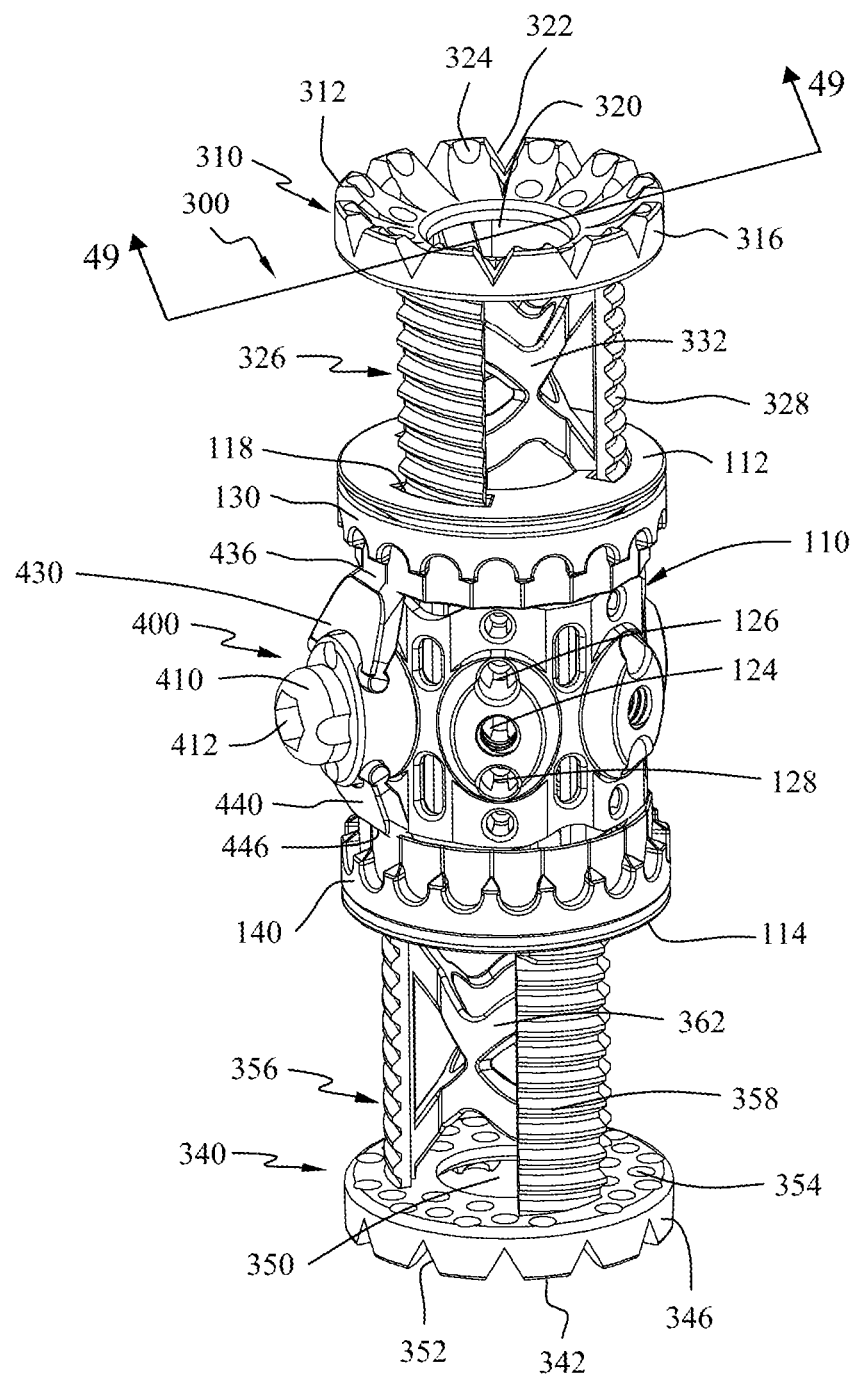
FIG. 48 is an assembled, perspective top view of the vertebral body device and locking member of FIG. 46, in accordance with an aspect of the present invention.
Figure 49:
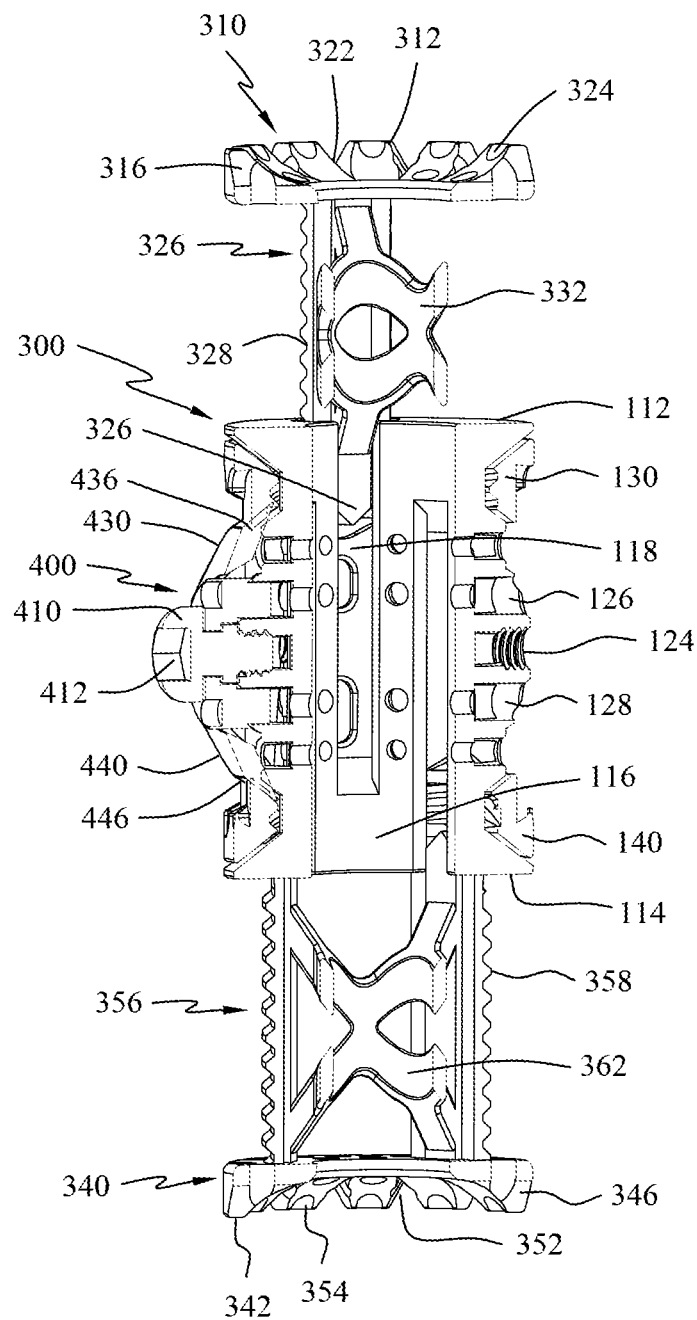
FIG. 49 is a cross-sectional view of the vertebral body device and locking member of FIG. 46 taken along line 49-49 in FIG. 48, in accordance with an aspect of the present invention.
Figure 50:
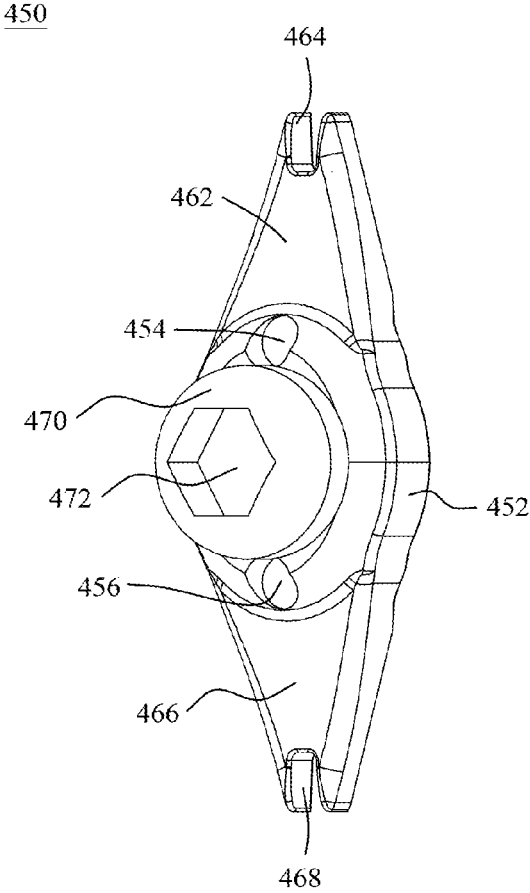
FIG. 50 is a perspective front view of a second locking member, in accordance with an aspect of the present invention.
Figure 51:
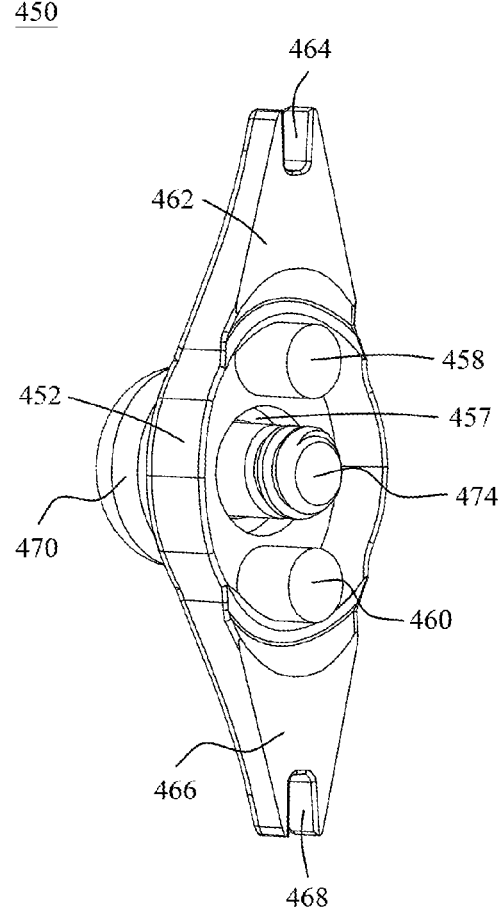
FIG. 51 is a perspective back view of the second locking member of FIG. 50, in accordance with an aspect of the present invention.
Figure 52:
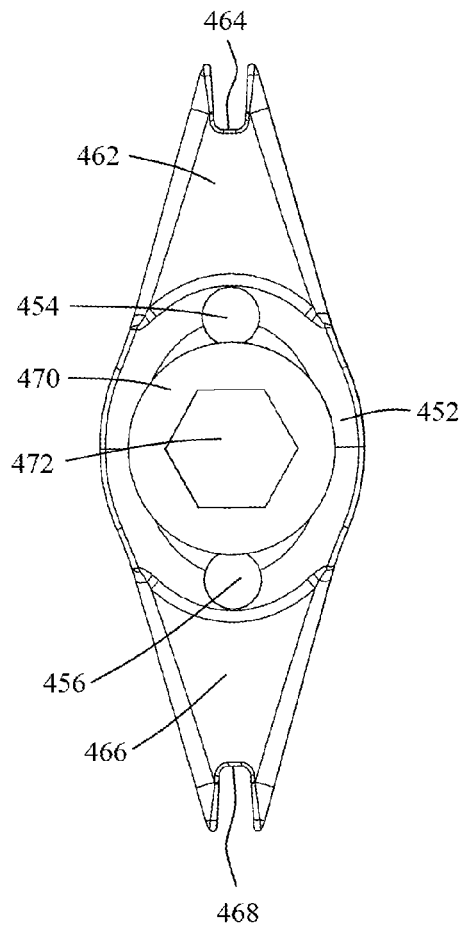
FIG. 52 is a front view of the second locking member of FIG. 50, in accordance with an aspect of the present invention.
Figure 53:
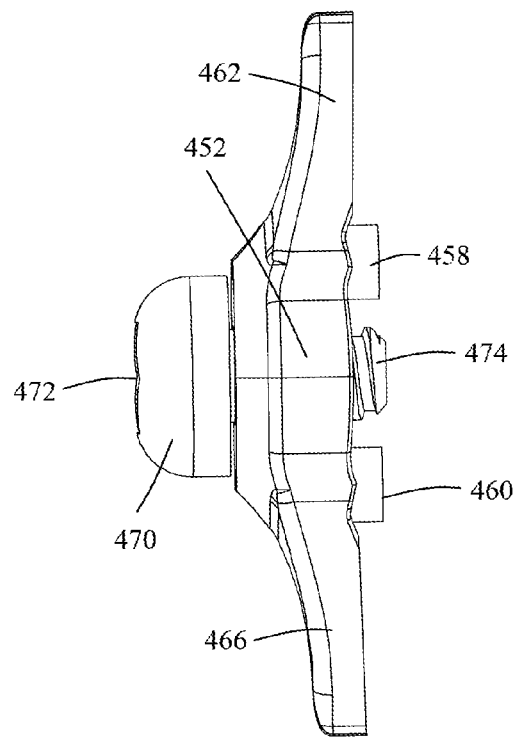
FIG. 53 is a side view of the second locking member of FIG. 50, in accordance with an aspect of the present invention.

The locking member 400 may also include a first wing member 430 rotatably coupled to a top of the base 402 and a second wing member 440 rotatably coupled to a bottom of the base 402. The first wing member 430 may include a first hinge 432 and a second hinge 434 on a first end of the first wing member 430. The first hinge 432 may be positioned on a first side of the wing member 430 and the second hinge 434 may be positioned on a second side of the wing member 430 opposite the first side. The first and second hinges 432, 434 may engage openings 404 positioned near the top of the base 402. The first wing member 430 may also include, for example, a tapered end 436 positioned on a second end of the first wing member 430 opposite the first end. The tapered end 436 may be sized to extend between the body 110 and one of the first rotating member 130 and second rotating member 140, as shown in FIGS. 47-49. The second wing member 440 may include a first hinge 442 and a second hinge 444 on a first end of the second wing member 440. The first hinge 442 may be positioned on a first side of the wing member 440 and the second hinge 444 may be positioned on a second side of the wing member 440 opposite the first side. The first and second hinges 442, 444 may engage openings 404 positioned near the bottom of the base 402. The second wing member 440 may also include, for example, a tapered end 446 positioned on a second end of the second wing member 440 opposite the first end. The tapered end 446 may be sized to extend between the body 110 and one of the first rotating member 130 and second rotating member 140, as shown in FIGS. 47-49.

With continued reference to FIGS. 47-49, once the device 300 is in the desired position, a locking member 400 may be inserted to secure the device 300 in the desired position. The locking member 400 may be inserted by coupling the locking member 400 to an insertion tool (not shown) with the wing members 430, 440 in an angled position. The first alignment projection 420 may be, for example, aligned with alignment opening 126 and the second alignment projection 422 may be, for example, aligned with alignment opening 128. The projections 420, 422 of the locking member 400 may then be inserted into the openings 126, 128 of the body 110, as shown in FIG. 47. Then, a driver (not shown) may be inserted into the tool opening 412 and the coupling member 410 may be rotated to secure the locking member 400 to the body 110. As the coupling member 410 is rotated the wing members 430, 440 engage the side of the body 110, the first wing member 430 may, for example, slide between the body 110 and the first rotating member 130 and the second wing member 440 may slide between the body 110 and the second rotating member 140. The tapered ends 436, 446 of the wing members 430, 440 may, for example, act as wedges to secure the rotating members 130, 140 and prevent them from rotating in order to secure the extension members 310, 340 in the desired position.

As shown in FIGS. 50-56, the locking member 450 may include a body 452 with a first recess 454, a second recess 456, and a hole 457. The first and second recess 454, 456 may be positioned on the front of the body 452. The hole 457 may be sized to receive a coupling member 470. The first recess 454 may be positioned above the hole 457 and the second recess 456 may be positioned below the hole 457. The recesses 454, 456 may be sized to engage an instrument for inserting the locking member 450 into the patient to engage an expandable vertebral body replacement device 100, 300. The body 452 may also include a first alignment projection 458 extending away from a back side of the body 452 and a second alignment projection 460 extending away from the back side of the body 452. The first alignment projection 458 may be positioned above the hole 457 and the second alignment projection 460 may be positioned below the hole 457. The first alignment projection 458 may be positioned to engage a first positioning hole 126 and the second alignment projection 460 may be positioned to engage a second positioning hole 128 or vice versa.

The body 452 may also include a first extension member 462 extending away from a top of the body 452 and a second extension member 466 extending away from a bottom of the body 452. The first extension member 462 may include a first channel 464 for engaging at least one groove 132, 142 of a rotating member 130, 140 to secure the device 100, 300 in the desired position. The second extension member 466 may include a second channel 468 for engaging at least one groove 132, 142 of a rotating member 130, 140 to secure the device 100, 300 in the desired position. The extension members 462, 466 may have, for example, a generally triangular shape, although other shapes are also contemplated.

The coupling member 470 may include a tool opening 472 positioned on the front and an engagement member 474 extending away from a back side. The engagement member 474 may be, for example, threaded to couple to the threads in the insertion tool opening 124 of the body 110 of the devices 100, 300. The tool opening 472 may be sized to receive a tool to rotate the coupling member 470. As the coupling member 470 is rotated the engagement member 474 is inserted into the opening 124 and the locking member 450 is secured to the body 110.

Figure 54:
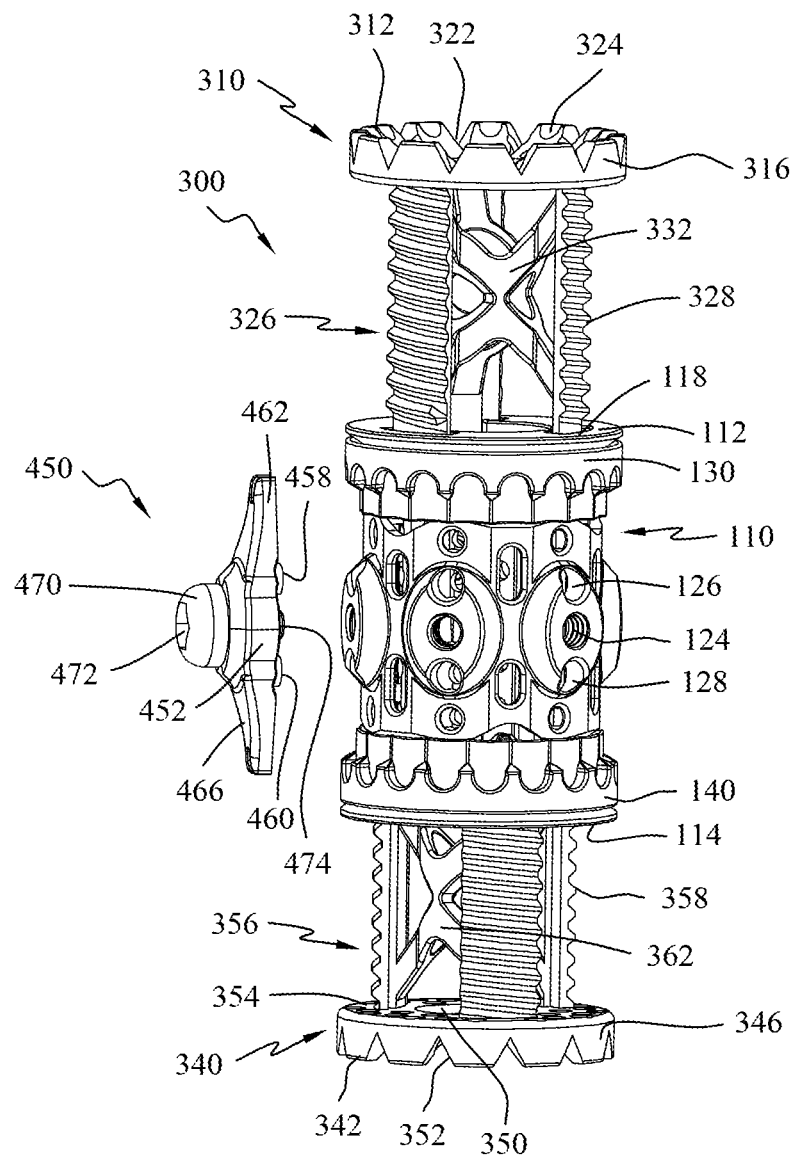
FIG. 54 is a partially exploded, perspective side view of a vertebral body device and the locking member of FIG. 50, in accordance with an aspect of the present invention.
Figure 55:
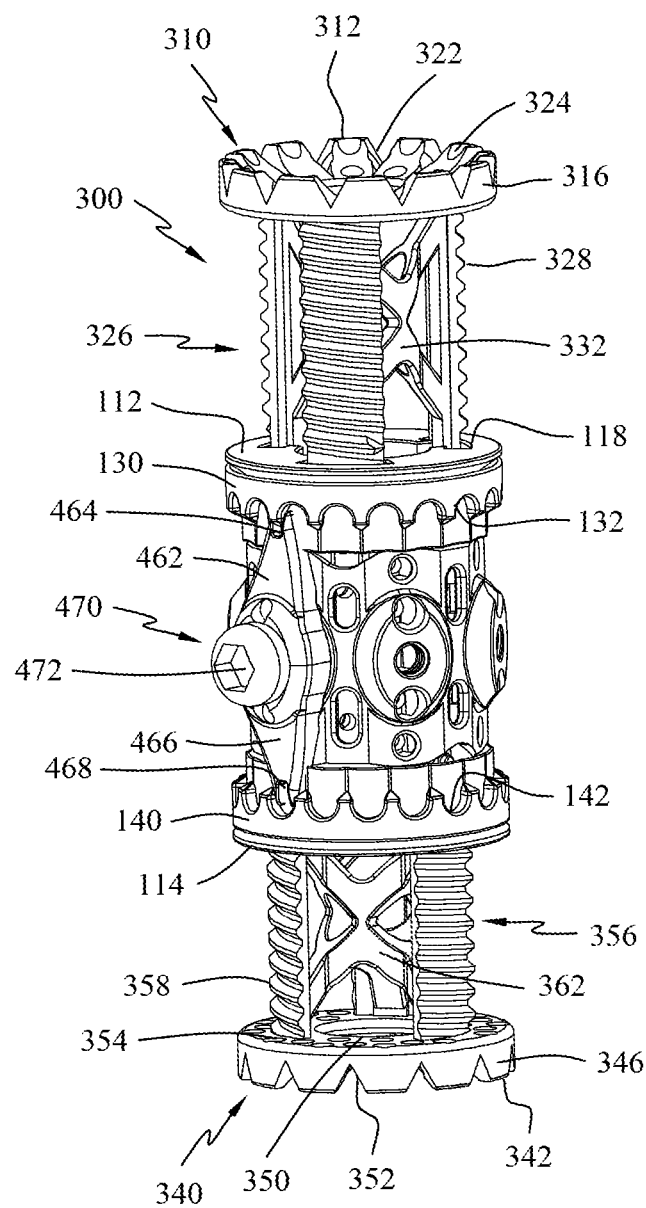
FIG. 55 is an assembled, perspective side view of the vertebral body device and locking member of FIG. 54, in accordance with an aspect of the present invention.
Figure 56:
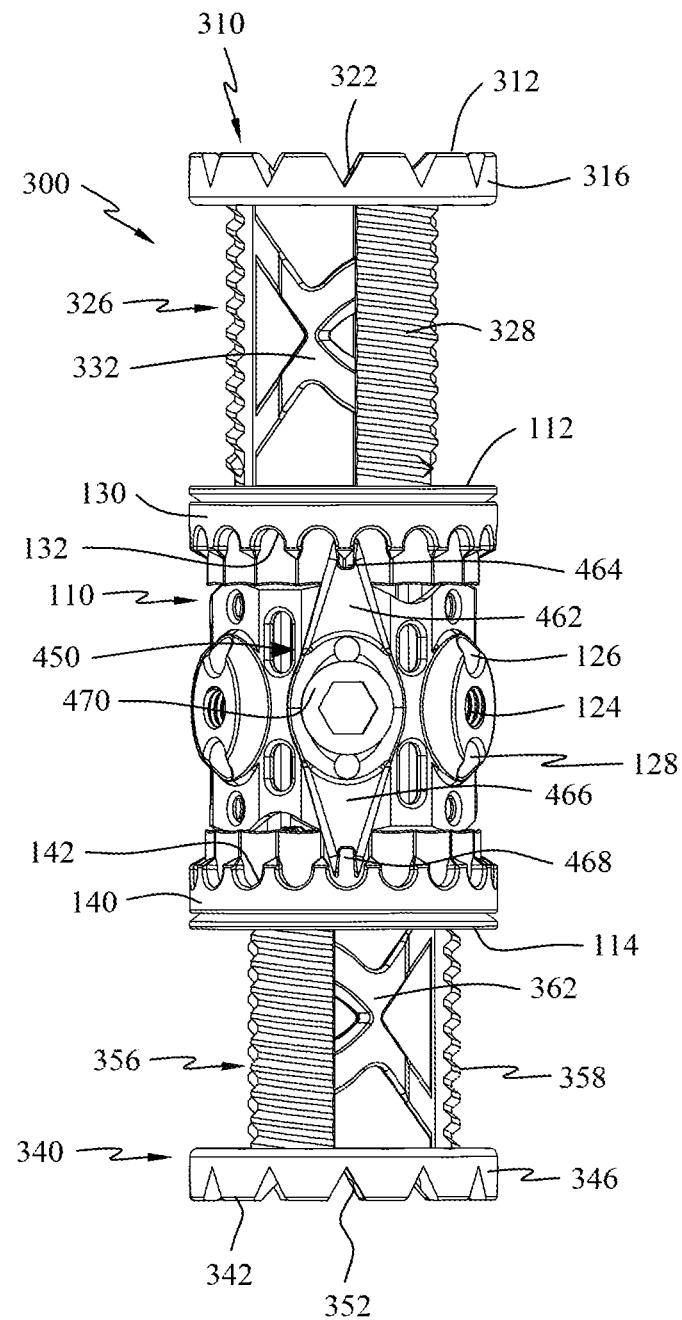
FIG. 56 is a front view of the vertebral body device and locking member of FIG. 54, in accordance with an aspect of the present invention.
Figure 57:
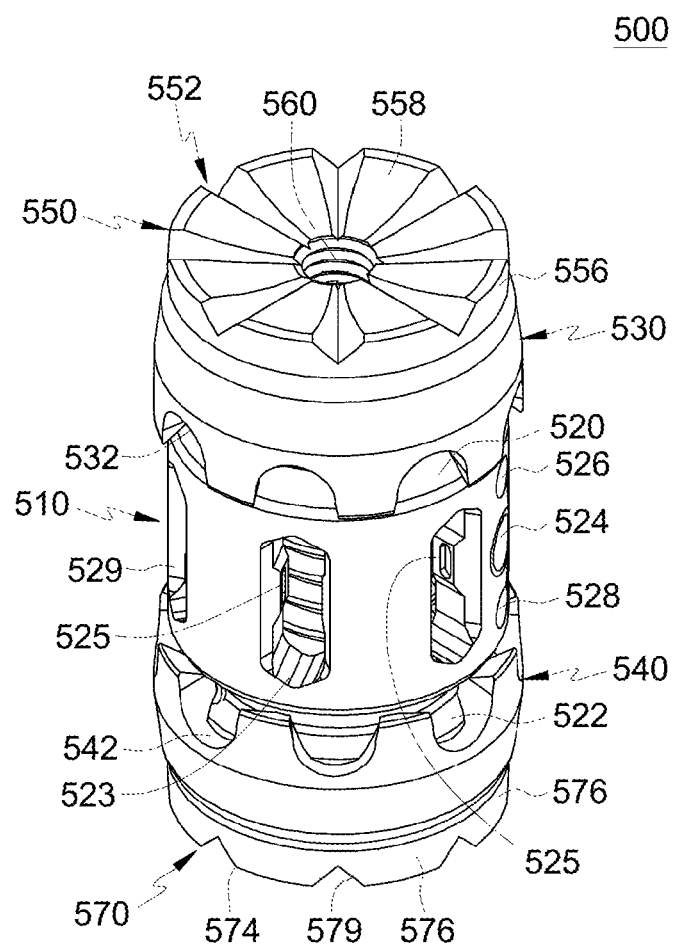
FIG. 57 is a top perspective view of an embodiment of a vertebral body implant, in accordance with an aspect of the present invention.
Figures 58, 59:
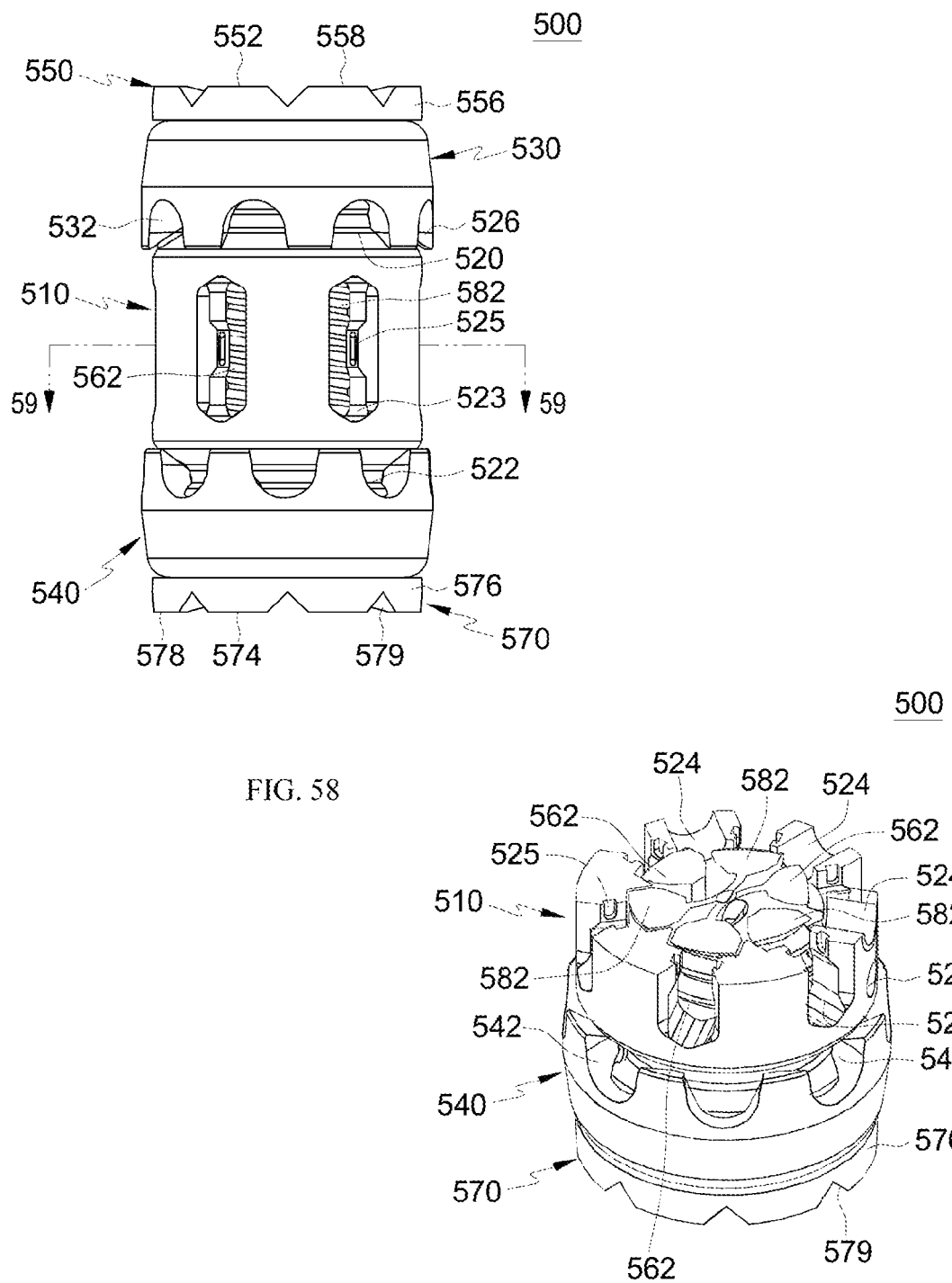
FIG. 58 is a side view of the implant of FIG. 57, in accordance with an aspect of the present invention.
FIG. 59 is a cross-sectional view of the implant of FIG. 57 taken along line 59-59 in FIG. 58, in accordance with an aspect of the present invention.

As shown in FIGS. 54-56, once the device 300 is in the desired position, a locking member 450 may be inserted to secure the device 300 in the desired position. The locking member 450 may be inserted by coupling the locking member 450 to an insertion tool (not shown). The first alignment projection 458 may be, for example, aligned with alignment opening 126 and the second alignment projection 460 may be, for example, aligned with alignment opening 128. The projections 458, 460 of the locking member 450 may then be inserted into the openings 126, 128 of the body 110, as shown in FIG. 55. Next, a driver (not shown) may be inserted into the tool opening 472 and the coupling member 470 may be rotated to secure the locking member 450 to the body 110. As the coupling member 470 is rotated the channels 464, 468 engage the gears 132, 142 of the first and second rotating members 130, 140. A tooth of the gears 132, 142 may be, for example, positioned within the channels 464, 468 of the locking member 450 or the end of the locking member 450 with the channels 464, 468 may be positioned in the groove of the gears 132, 142 to secure the rotating members 130, 140 and lock the device 300 in the desired position.

Referring now to FIGS. 57-61, there is illustrated another embodiment of a vertebral body replacement implant 500. The vertebral body implant 500 may include a body 510, a first rotating member 530 rotatably coupled to the first end 512 of the body 510, a second rotating member 540 rotatably coupled to the second end 514 of the body 510, a first extension member 550 moveably coupled to a first end 512 of the body 510, and a second extension member 570 moveably coupled to a second end 514 of the body 510.

As shown in FIGS. 60-67, the body 510 may include an opening 516 extending from the first end 512 to the second end 514, for example, along the longitudinal axis of the body 510. The opening 516 may include at least two channels 517, 518, 519 extending into the body 510 from the opening 516. At least one first channel 517 may extend from the first end 512 toward the second end 514 and at least one second channel 518 may extend from the second end 514 toward the first end 512. At least one third channel 519 may extend from the first end 512 to the second end 514. In the depicted embodiment, the at least one first channel 517 may be one first channel 517, the at least one second channel 518 may be one second channel 518, and the at least one third channel 519 may be, for example, four channels 519. The channels 517, 518, 519 may be, for example, evenly spaced around the opening 516. As shown, the body 510 may include, for example, one first channel 517 open on the first end 512, one second channel 518 open on the second end 514, and four third channels 519 open on both the first and second ends 512, 514. Alternative numbers of channels 517, 518, 519 are also contemplated, for example, the body 510 may include more or less channels 517, 518, 519.

Figure 60:
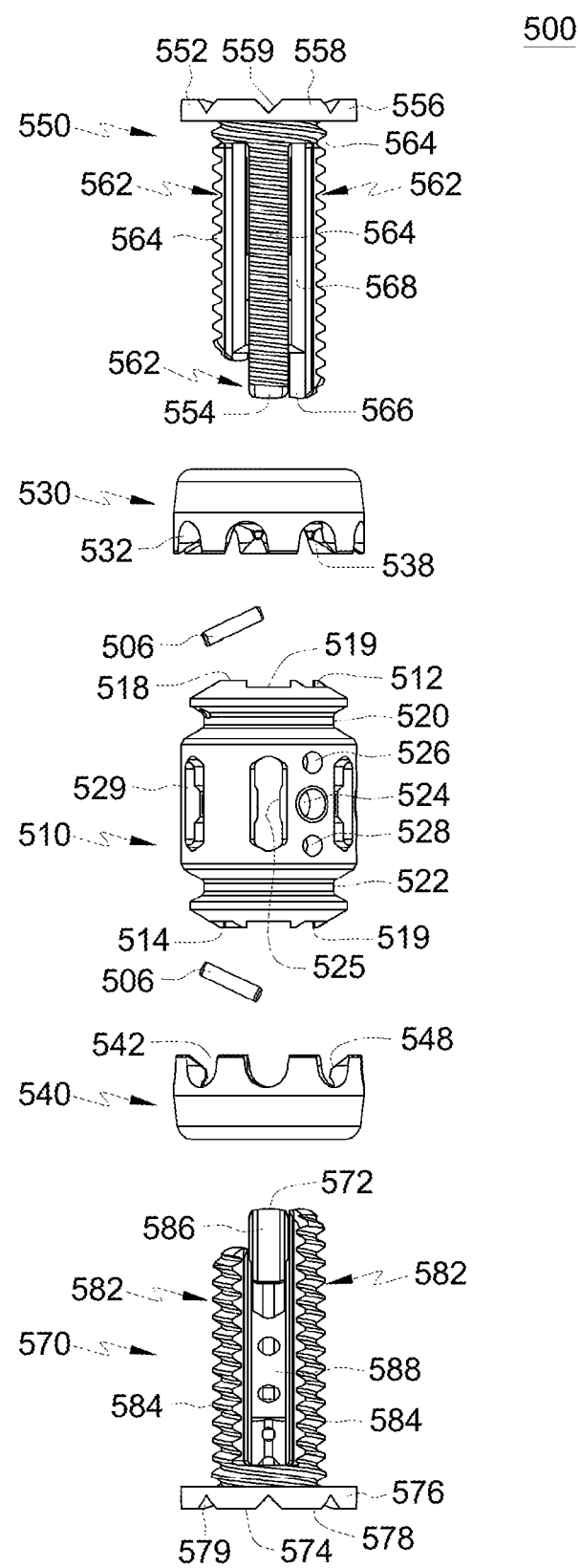
FIG. 60 is an exploded side view of the implant of FIG. 57, in accordance with an aspect of the present invention.
Figure 61:
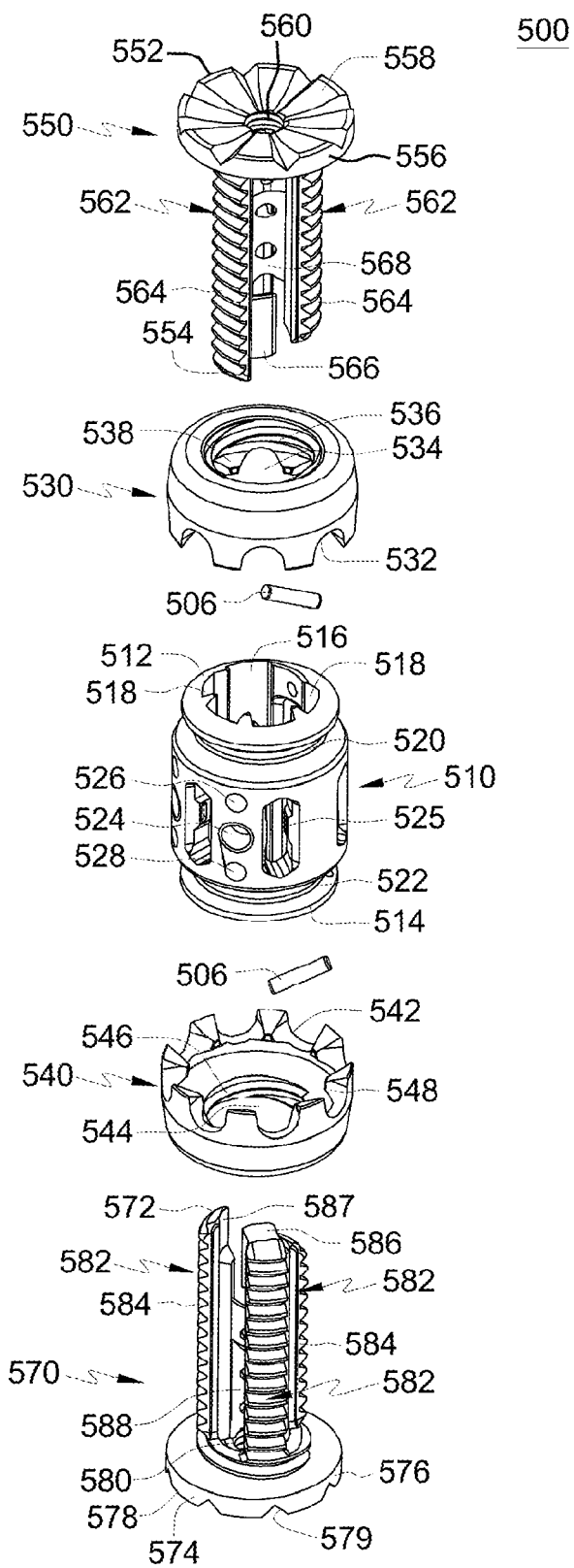
FIG. 61 is an exploded perspective view of the implant of FIG. 57, in accordance with an aspect of the present invention.
Figure 62:
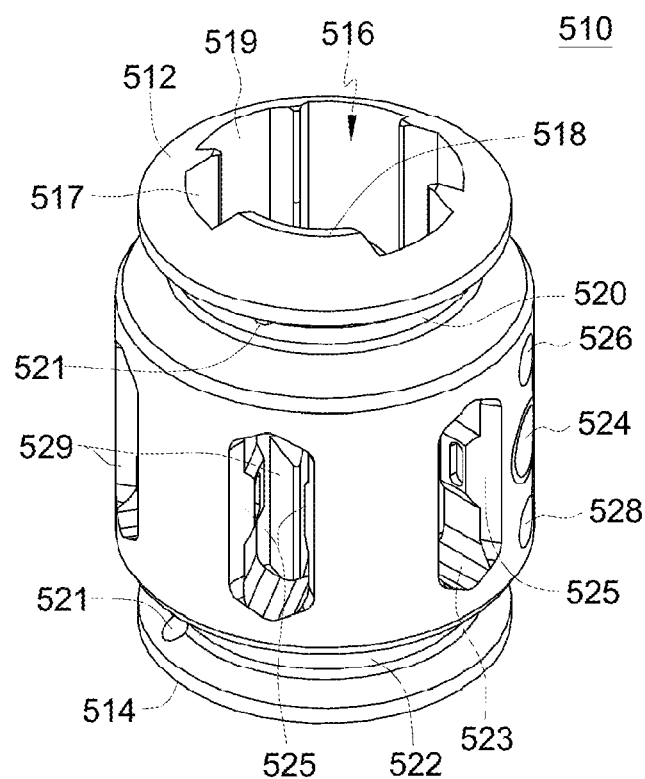
FIG. 62 is a top perspective view of a body of the vertebral body implant of FIG. 57, in accordance with an aspect of the present invention.
Figure 63:
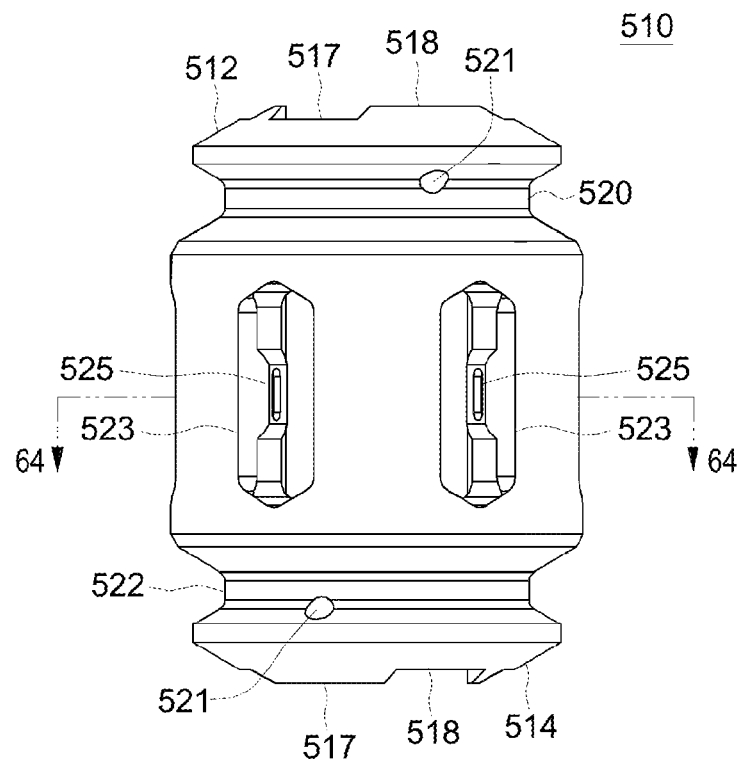
FIG. 63 is a side view of the body of FIG. 62, in accordance with an aspect of the present invention.
Figure 64:
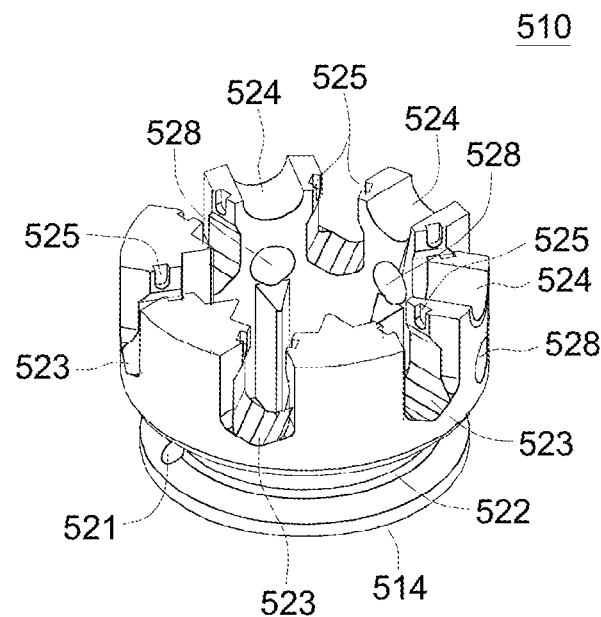
FIG. 64 is a perspective cross-sectional view of the body of FIG. 62 taken along line 64-64 in FIG. 63, in accordance with an aspect of the present invention.
Figure 65:
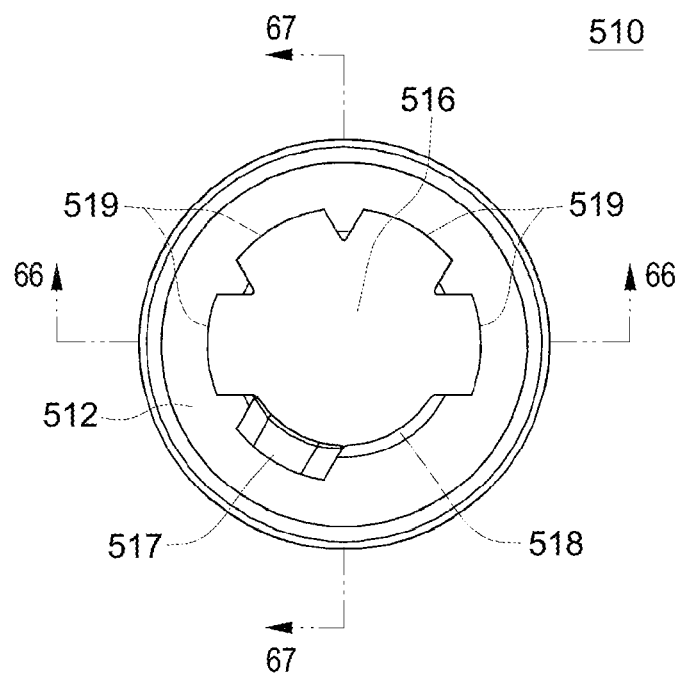
FIG. 65 is a top view of the body of FIG. 62, in accordance with an aspect of the present invention.
Figure 66:
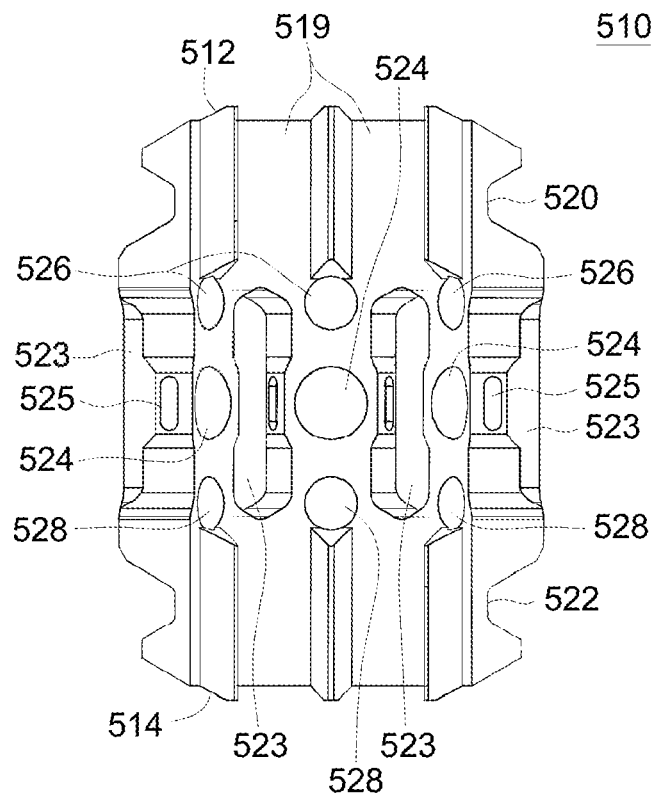
FIG. 66 is a cross-sectional view of the body of FIG. 62 taken along line 66-66 in FIG. 65, in accordance with an aspect of the present invention.
Figure 67:
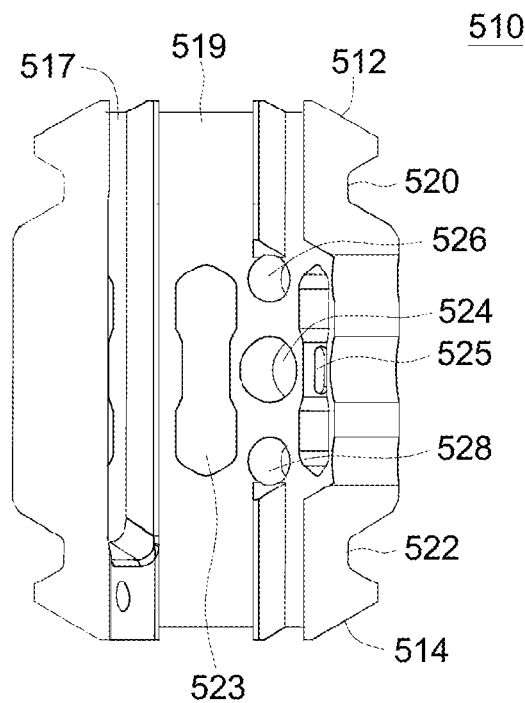
FIG. 67 is a cross-sectional view of the body of FIG. 62 taken along line 67-67 in FIG. 65, in accordance with an aspect of the present invention.
Figure 84:
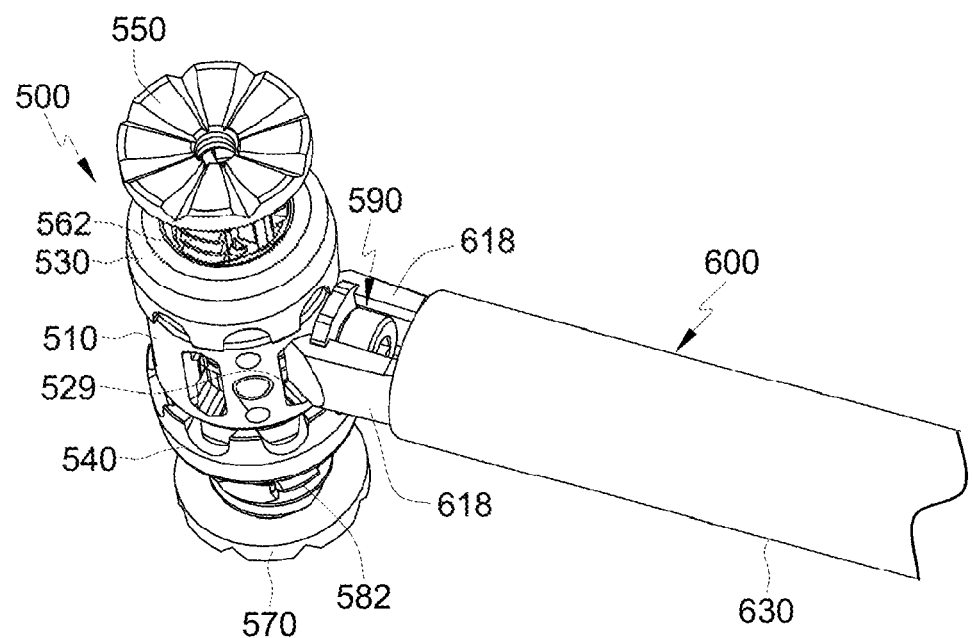
FIG. 84 is a top perspective view of the vertebral body implant of FIG. 57 in a second position and including a locking mechanism engaging the vertebral body implant of FIG. 57 and a portion of the insertion tool of FIG. 77, in accordance with an aspect of the present invention.
Figure 85:
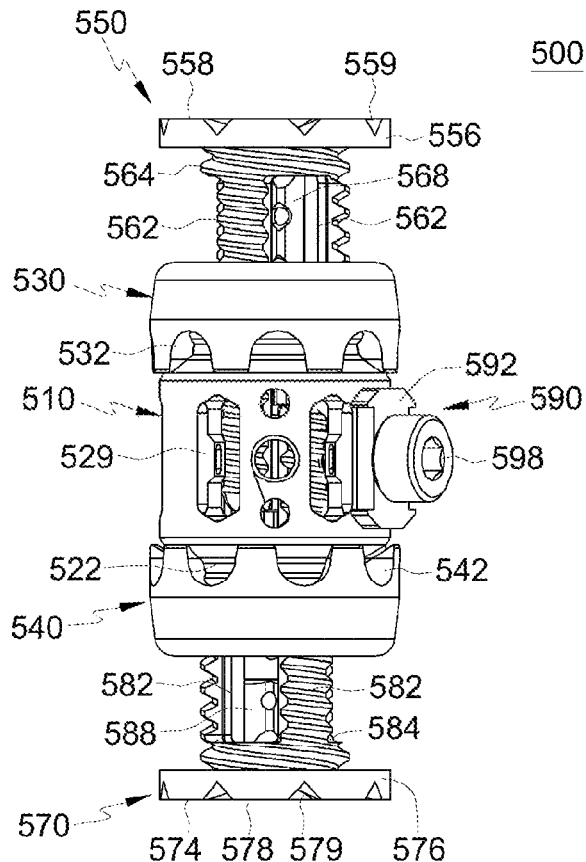
FIG. 85 is a side view of the vertebral body implant of FIG. 57 in an expanded position with the locking mechanism engaging at least a portion of the implant, in accordance with an aspect of the present invention.
Figure 86:
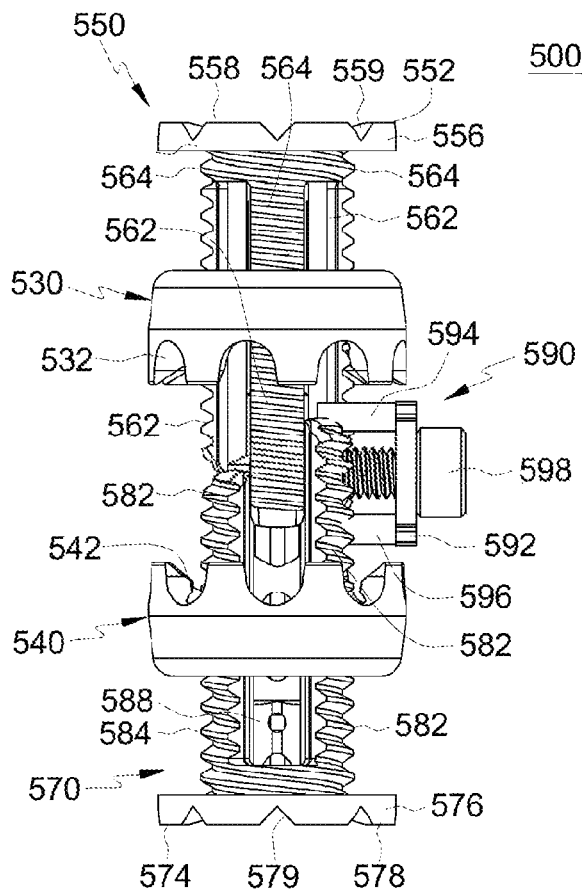
FIG. 86 is a side view of the vertebral body implant of FIG. 85 with the body of FIG. 62 removed, in accordance with an aspect of the present invention.
Figure 87:
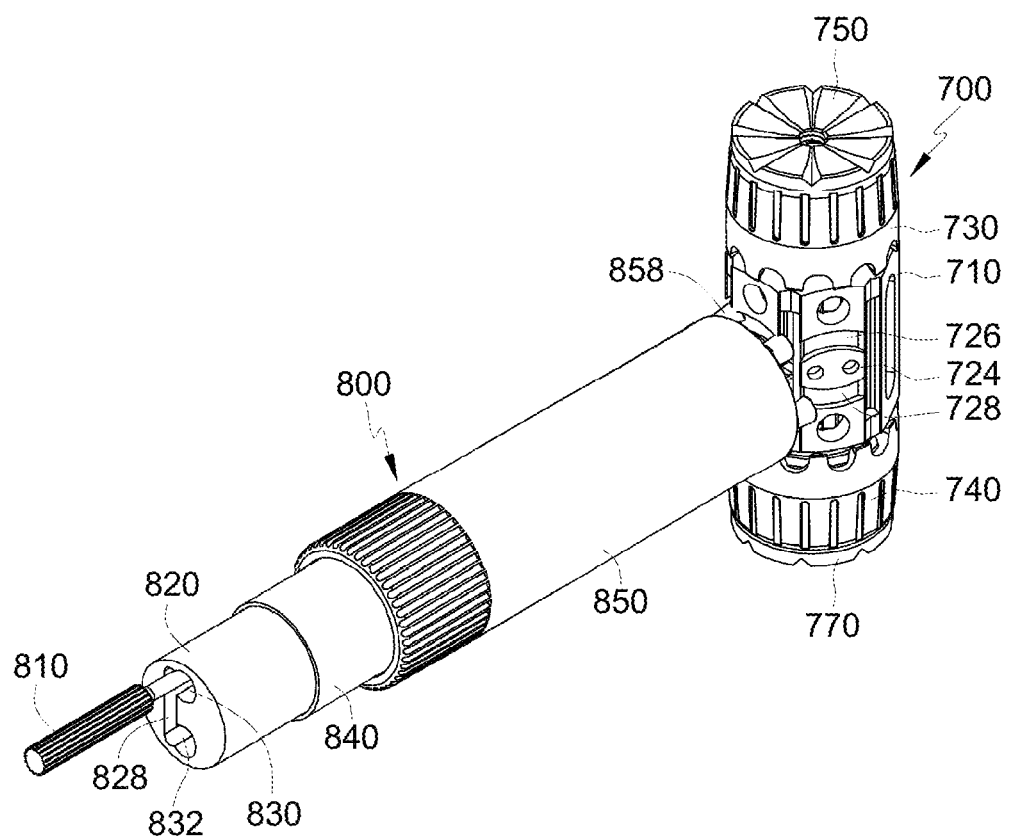
FIG. 87 is another embodiment of a vertebral body device system including a vertebral body implant and insertion tool, in accordance with an aspect of the present invention.

The exterior surface of the body 510 may further include a first groove 520 near the first end 512 and a second groove 522 near the second end 514, as shown in FIGS. 60-63. The first and second grooves 520, 522 may extend around the circumference of the body 510 and be sized to receive the first and second rotating members 530, 540, respectively. Each groove 520, 522 may include an opening 521 for receiving a pin 506. As shown in FIGS. 60-62, the body 510 may also include at least one aperture 524 positioned around the circumference of the exterior surface. The at least one aperture 524 may be positioned, for example, at a midpoint between the first end 512 and second end 514 of the body 510. The at least one aperture 524 may be, for example, a threaded opening. The body 510 may also include at least one first locking hole 526 superior to the aperture 524 and at least one second locking hole 528 inferior to the aperture 524. The aperture 524, first locking hole 526, and second locking hole 528 may be sized and shaped to receive a locking insert 590, as shown in FIGS. 84-86. In the depicted embodiment, the body 510 may include, for example, three apertures 524, three first locking holes 526, and three second locking holes 528. The three sets of openings 524, 526, 528 may be positioned adjacent to each other. The body 510 may further include openings 523 positioned around the circumference of the body 510. The openings 523 may each include at least one gripping surface or region 525 on each side of the opening 523 to couple to an insertion tool, such as, tool 600 described in greater detail below. As depicted, the three sets of openings 524, 526, 528 may be positioned between the openings 523 and adjacent to each other, such that, there are three solid portions of the body 510 positioned between the openings 523.

Figure 68:
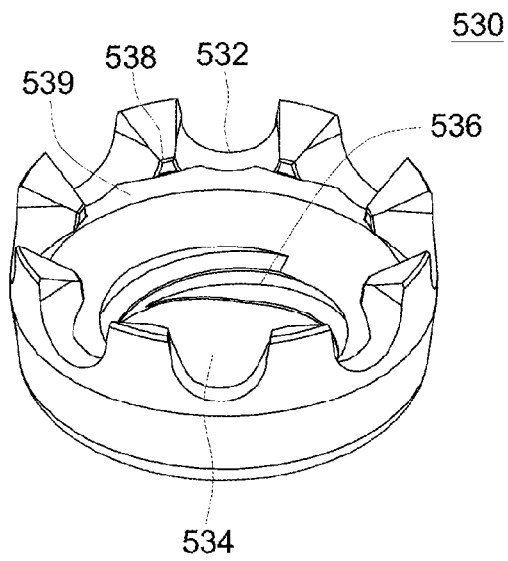
FIG. 68 is a perspective view of a rotating member of the vertebral body implant of FIG. 57, in accordance with an aspect of the present invention.
Figure 69:
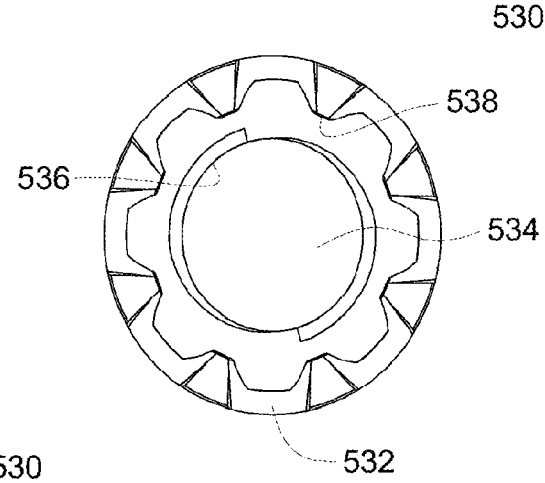
FIG. 69 is a first end view of the rotating member of FIG. 68, in accordance with an aspect of the present invention.
Figure 70:
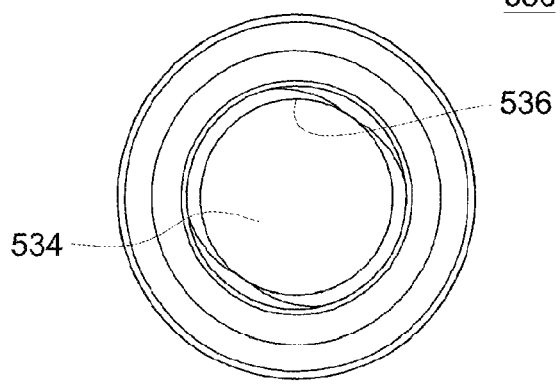
FIG. 70 is a second end view of the rotating member of FIG. 68, in accordance with an aspect of the present invention.

A rotating members 530, 540 are shown in FIGS. 60 and 61 and the rotating member 530 is shown in greater detail in FIGS. 68-70. The first rotating member 530 may include a center opening 534 extending through the first rotating member 530. The exterior surface of the first rotating member 530 may include a plurality of grooves, notches, gear teeth, teeth, or scallops 532, as best seen in FIGS. 68 and 69. The plurality of notches 532 may be, for example, sized to receive an insertion tool, such as tool 600 described in greater detail below. The first rotating member 530 may also include threads 536 on the interior surface of the member 530, as shown in FIGS. 61 and 68. In addition, the first rotating member 530 may include at least one protrusion 538 positioned between each notch 532 to engage the groove 520 in the body 510.

The second rotating member 540, as shown in FIGS. 60 and 61, may include a plurality of notches 542, a center opening 544, threads 546, and at least one protrusion 548. The plurality of notches 542, center opening 544, threads 546, and at least one protrusion 548 may be of the type described above with reference to the plurality of grooves 532, center opening 534, threads 536, and at least one protrusion 538 of first rotating member 530, which will not be described again here for brevity's sake.

Figure 71:
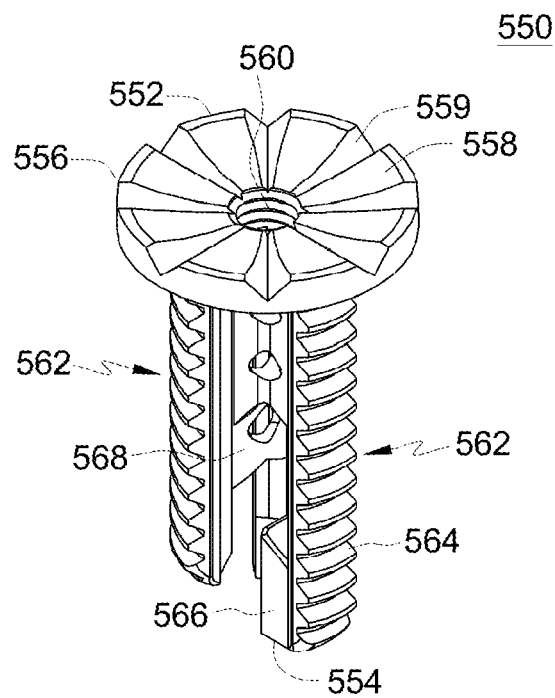
FIG. 71 is a first end perspective view of an extension member of the vertebral body implant of FIG. 57, in accordance with an aspect of the present invention.

Referring now to FIGS. 60 and 61, the extension members 550, 570 are shown. FIGS. 71-74 show the first extension member 550. The first extension member 550 may include a first end 552 and a second end 554. The first extension member 550 may also include a top portion or first end cap 556 at the first end 552 and at least one leg member 562 extending away from the top portion 556 and toward the second end 554. The top portion 556 may include a curved top surface 558, for example, a hemispherical or cylindrical shaped cup, and a center opening 560, as shown in FIGS. 61 and 71. The top surface 558 may also include grooves 559.

The curved top surface 558, grooves 559, and center opening 560 may be configured to receive autologous bone graft or allograft material which will contact and allow for fusion with the adjacent vertebral bodies and additional graft material positioned between the at least one leg member 562. The curved surface 558 may be, for example, sized to allow the graft material to be positioned within the first extension member 550 to minimize the height. In addition, the hemispherical shaped cup may be selected, for example, to minimize the amount of graft material necessary to fill the curved surface 558. The top surface 558 may be, for example, coated, textured, porous, or of a trabecular metal nature to allow for bone growth into the first extension member 550 after implantation. In an alternative embodiment, it is also contemplated that the curved top surface 558 may be, for example, a mesh or open slotted top surface to allow for the bone graft material positioned in the top portion 556 to make contact with bone graft material positioned between the at least one leg member 562. The top portion 556 may also be configured to receive, for example, end caps (not shown) with lordosis or a larger footprint to contact larger adjacent vertebral bodies at the outer ring of their end plates.

Figure 72:
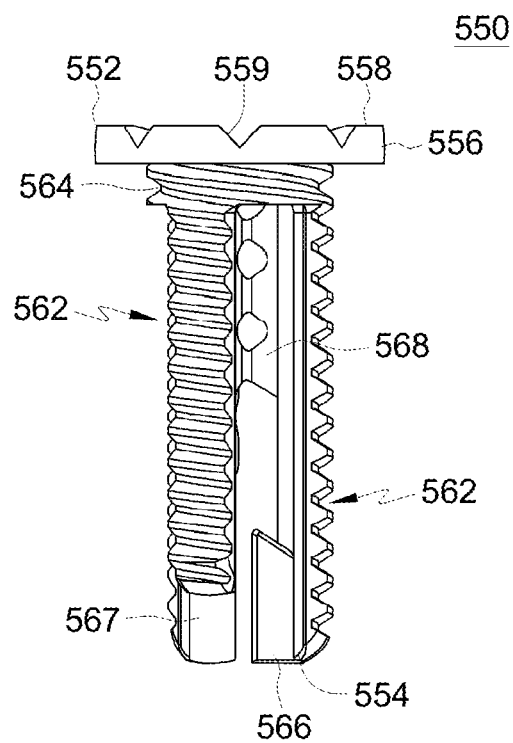
FIG. 72 is a side view of the extension member of FIG. 71, in accordance with an aspect of the present invention.
Figure 73:
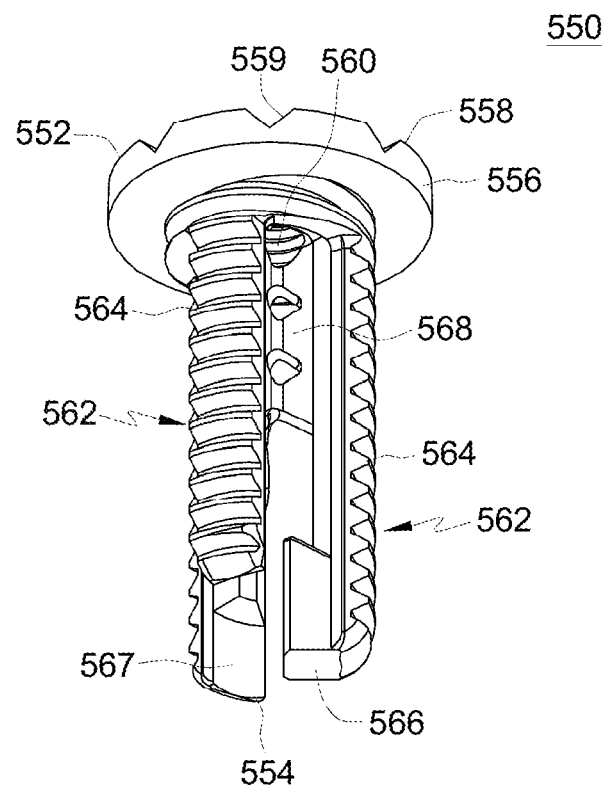
FIG. 73 is a second end perspective view of the extension member of FIG. 71, in accordance with an aspect of the present invention.
Figure 74:
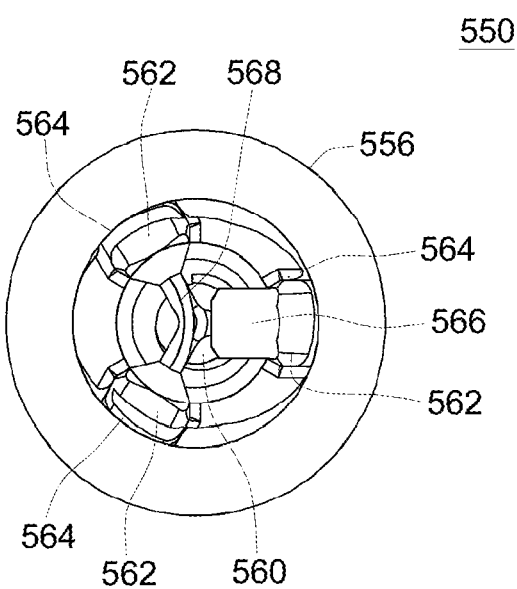
FIG. 74 is an end view of the extension member of FIG. 71, in accordance with an aspect of the present invention.

The at least one leg member 562 may be, for example, three leg members 562, as shown in FIGS. 71-74. The leg members 562 may include threads 564 on an exterior surface. The second end 554 of the leg members 562 may be, for example, tapered or angled. The leg members 562 may include a short leg member 562 and two longer leg members 562. The short leg member 562 may be received within the channel 517. A first longer leg member 562 may include a protrusion or hook 566 for engaging a channel 519 in the body 510. The protrusion 566 may include an angled end, as shown in FIG. 72, to engage at least one retention pin 506 during use. A second longer leg member 562 may include, for example, a recessed region 567. The threads 564 on the legs 562 engage the threads 536 on an interior surface of the first rotating member 530 to translate the leg member 562 with respect to the body 510. The threads 564 may extend from the second end 554 to a bottom surface of the first end cap 556. The leg members 562 may be curved to enable the leg members 562 to rotate with respect to the first rotating member 530. The first extension member 550 may also include support members 568 positioned between and connected to the leg members 562. The support members 568 may be, for example, cross-hatching braces positioned in rings. As depicted in FIGS. 71-74, the support members 568 may, for example, extend out from the back side of the leg members 562 and be connected between the leg members 562 in "Y" or "T" shaped arrangements. The support member 568 may also form an inner cylinder aligned with the opening 560 to form an inner channel through the implant 500. The arrangement of the leg members 562 may be, for example, curved between the leg members 562 to form a ring-like shape.

The second extension member 570, as shown in FIGS. 60 and 61, may include a first end 572 and a second end 574. The second extension member 570 may also include a bottom portion or second end cap 576 at the first end 572 and at least one leg member 582 extending away from the bottom portion 576 and to the second end 574. The bottom portion 576 may include a curved bottom surface 578 and an opening 580. The curved bottom surface 578 may be of the type described above with respect to the curved top surface 558, which will not be described again here for brevity's sake. The curved bottom surface 578 and center opening 580 may also be configured to receive autologous bone graft or allograft material as described in greater detail above with respect to the first extension member 550.

The at least one leg member 582 may be, for example, three leg members 582 and may include threads 584, protrusion or hook 586, and support members 588. The threads 584, protrusions 586, and support members 588 may be of the type described above with reference to threads 564, protrusion or hook 566, and support members 568, which will not be described again here for brevity's sake. The first end 572 of the leg members 582 may be, for example, tapered or angled. The leg members 582 may include a short leg member 582 and two longer leg members 582. The short leg member 582 may be received within the channel 518. A first longer leg member 582 may include a protrusion or hook 586 for engaging a channel 519 in the body 510. The protrusion 586 may include an angled end, as shown in FIG. 61, to engage at least one retention pin 506 during use. A second longer leg member 582 may include, for example, a recessed region 587. The threads 584 on the legs 582 engage the threads 546 on an interior surface of the second rotating member 540 to translate the leg member 582 with respect to the body 510. The threads 584 may extend from the first end 572 to a bottom surface of the second end cap 576. The leg members 582 may be curved to enable the leg members 582 to rotate with respect to the second rotating member 540. The first extension member 550 may also include support members 588 positioned between and connected to the leg members 582. The support members 588 may be, for example, cross-hatching braces positioned in rings. As depicted in FIGS. 71-74, the support members 588 may, for example, extend out from the back side of the leg members 582 and be connected between the leg members 582 in "Y" or "T" shaped arrangements. The support member 588 may also form an inner cylinder aligned with the opening 580 to form an inner channel through the implant 500. The arrangement of the leg members 582 may be, for example, curved between the leg members 582 to form a ring-like shape.

The implant 500 may also include a locking mechanism 590, as shown in FIGS. 84-86. The locking mechanism 590 may include a plate 592 with a first locking pin or post 594, a second locking pin or post 596 and an opening (not shown), for example, a threaded opening. The first locking post 594 is coupled to and extending away from the back surface of the plate 592. The second locking post 596 coupled to and extending away from the back surface of the plate 592. The locking posts 594, 596 are sized and shaped to engage the legs 562, 582 of the extension members 550, 570. The threaded opening (not shown) may be centered in the middle of the plate 592 and sized and shaped to receive a fastener 598 to lock the implant 500 in a desired position.

The vertebral body replacement device 500 may be assembled by obtaining a body 510 with a first rotating member 530 positioned in the first groove 520 and a second rotating member 540 positioned in the second groove 522. Next, the first and second extension members 550, 570 may be inserted into the channels 517, 518, 519 in the opening 516 of the body 510. The first extension member 550 may be inserted into the channels 517, 519 from the first end 512. During insertion into the channels 517, 519, the protrusion 566 of the first extension member 550 may be aligned with at least one channel 519 on the interior surface of the body 510. The first extension member 550 may be translated until the threads 564 of the leg members 562 engage the interior threads 536 of the first rotating member 530. The first rotating member 530 may be rotated until the first extension member 550 engages the first end 512 of the body 510. Once the first extension member 550 is positioned in the body 510, then, the second extension member 570 may be inserted into the opening 516. The second extension member 570 may be inserted into the channels 518, 519 from the second end 514. During insertion into the channels 518, 519, the protrusion 586 of the second extension member 570 may be aligned with at least one channel 519 on the interior surface of the body 510. The second rotating member 540 may be rotated until the second extension member 570 engages the second end 514 of the body 510. The locking plate may be coupled to the implant 500 using the aperture 524 and locking holes 526, 528. The fastener 598 may be partially screwed into place, so that the locking plate is coupled to the implant 500.

Figure 75:
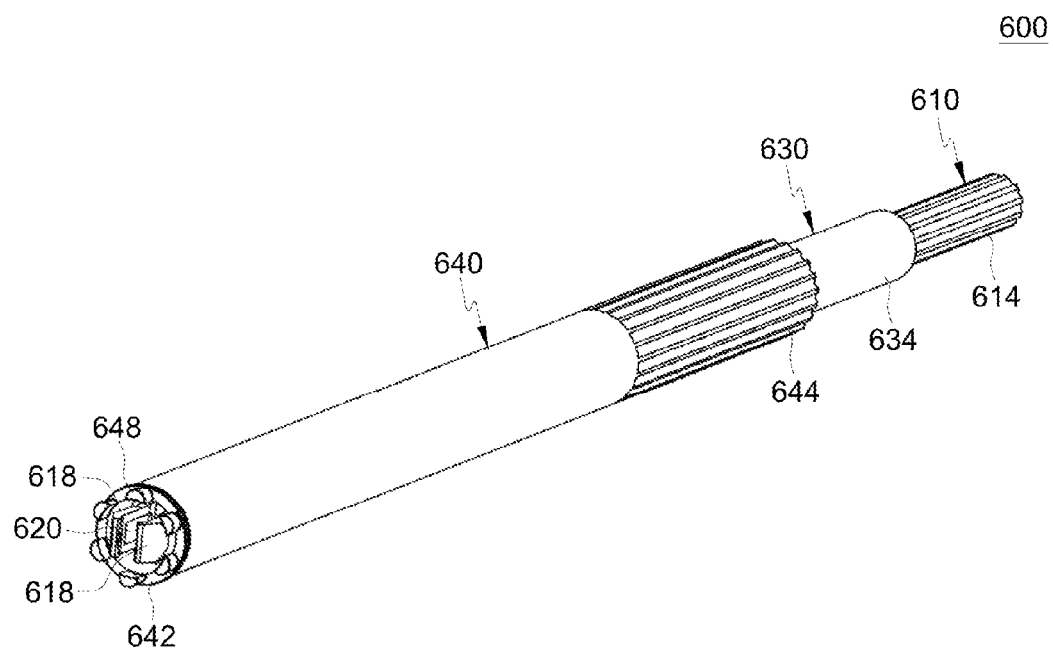
FIG. 75 is a perspective view of one embodiment of an insertion tool for the vertebral body implant of FIG. 57, in accordance with an aspect of the present invention.
Figure 76:
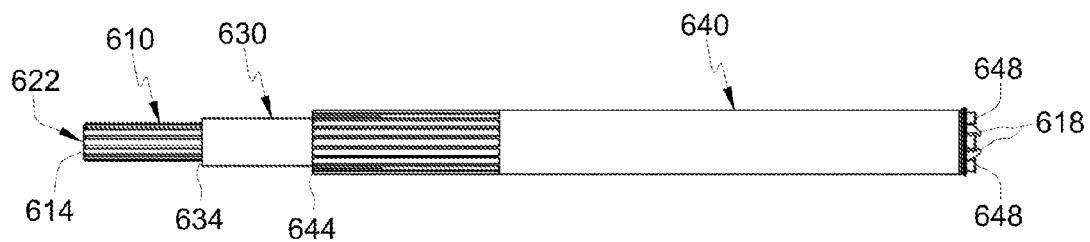
FIG. 76 is a side view of the insertion tool of FIG. 75, in accordance with an aspect of the present invention.
Figure 77:
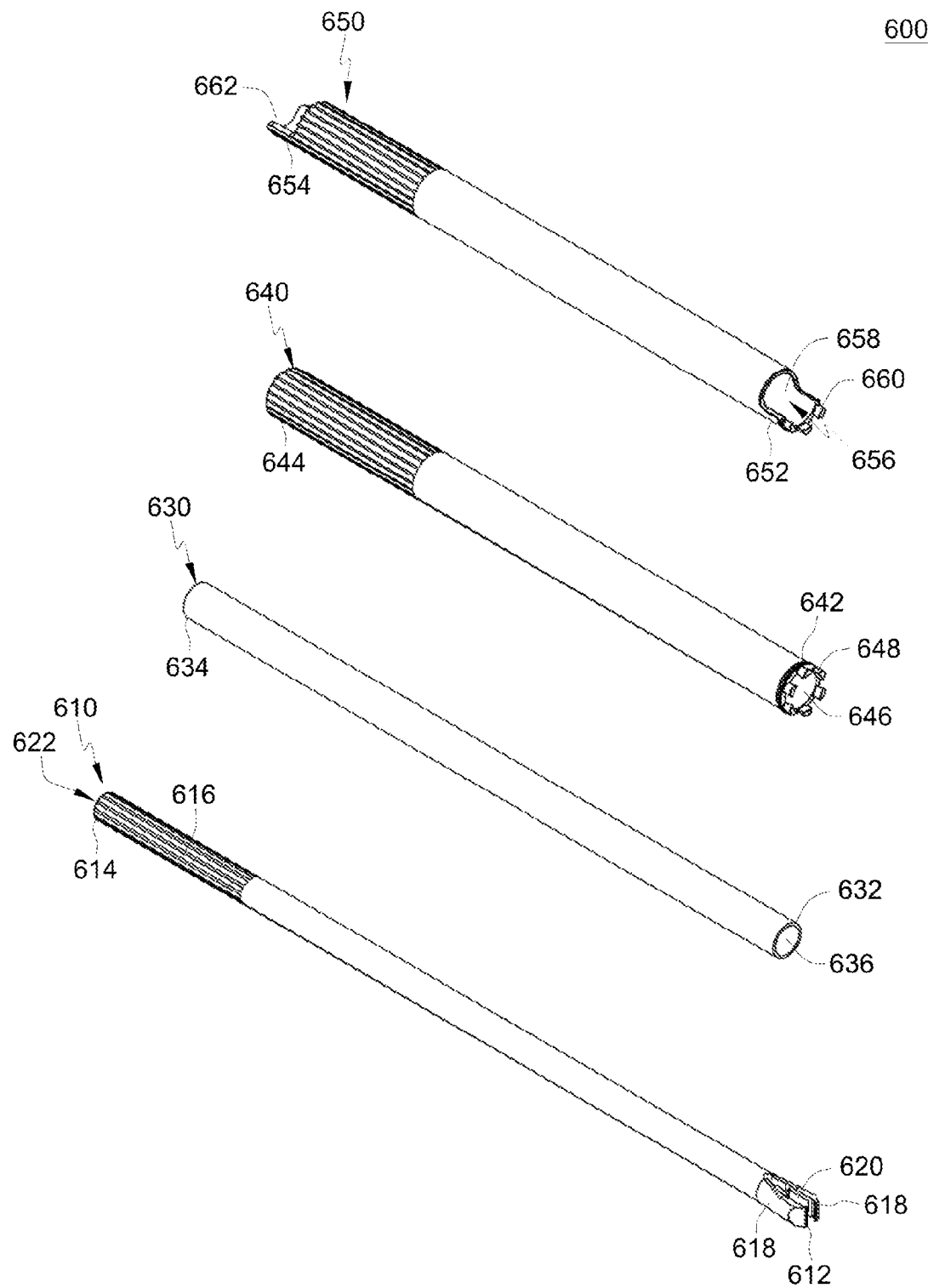
FIG. 77 is an exploded view of two embodiments of an insertion tool for the vertebral body implant of FIG. 57, in accordance with an aspect of the present invention.
Figure 78:
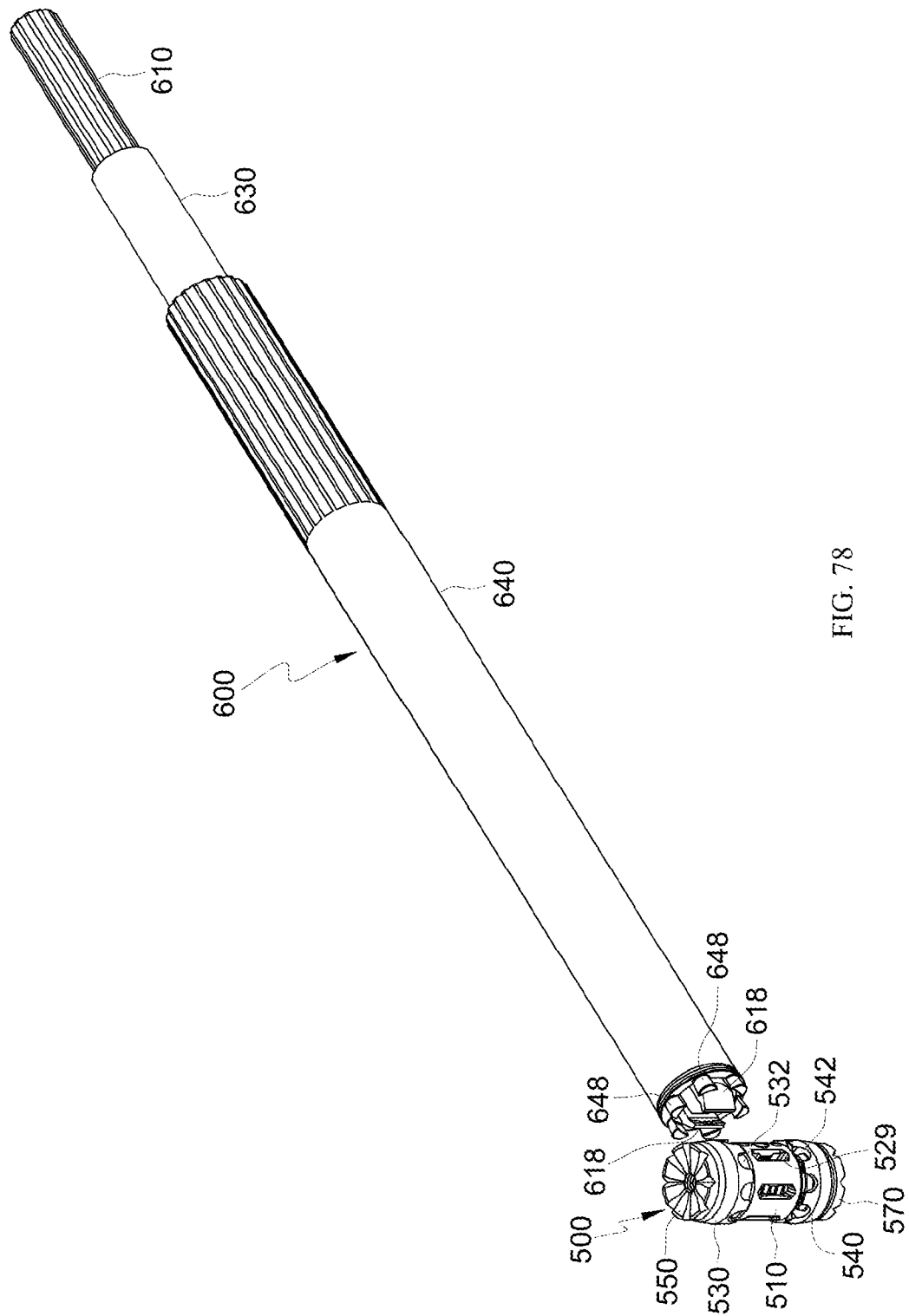
FIG. 78 is a perspective view of a vertebral body implant system including the implant of FIG. 57 and a first insertion tool of FIG. 75, in accordance with an aspect of the present invention.

An embodiment of an insertion tool 600 is shown in FIGS. 75-77. The insertion tool 600 may include a gripping member or tong member 610, a compression sleeve 630, a first deployment handle 640 and a second deployment handle 650. The gripping member 610 has a first end 612 and a second end 614 opposite the first end 612. The second end 614 may include a handle portion 616. The first end 612 may include two gripping arms 618 and each gripping arm 618 may include a channel 620 on an interior surface of the gripping arms 618. The gripping arms 618 sized and shaped to engage the gripping surfaces 525 on the body 510. The gripping arms 618 are also sized and shaped to grasp gripping surfaces 525 on body 510 while a locking member 590 is attached to or assembled to the body 510. The gripping arms 618 may be used to remove and reposition the locking member 590. The gripping member 610 may also include an opening extending along the longitudinal axis of the member 610 from the first end 612 to the second end 614. The compression sleeve 630 including a first end 632 and a second end 634 opposite the first end 632. The compression sleeve 630 also including an opening 636 extending from the first end 632 to the second end 634 and sized to receive the gripping member 610 and clamp the gripping arms 618 together to secure the implant 500 to the insertion tool 600.

As shown in FIGS. 75-81, the first deployment handle 640 includes a first end 642 and a second end 644 opposite the first end 642. The first deployment handle 640 also includes an opening 646 extending from the first end 642 to the second end 644. The first end 642 may also include a plurality of projections 648 sized and shaped to rotate the two rings 530 and 540 simultaneously to translate both extension members 550, 570 simultaneously. The plurality of projections 648 may be, for example, cone shaped or angled toward the point of attachment with the first end 642 of the handle 640 to allow for the projections 648 to engage the grooves or teeth 532, 542 of the rotating members 530, 540. The teeth 532, 542 may have, for example, an undercut or angled shape to lock the plurality of projections 648 into the teeth 532, 542 and prevent jumping of the projections 648 with respect to the teeth 532, 542 as the handle 610 is rotated.

Figure 82:
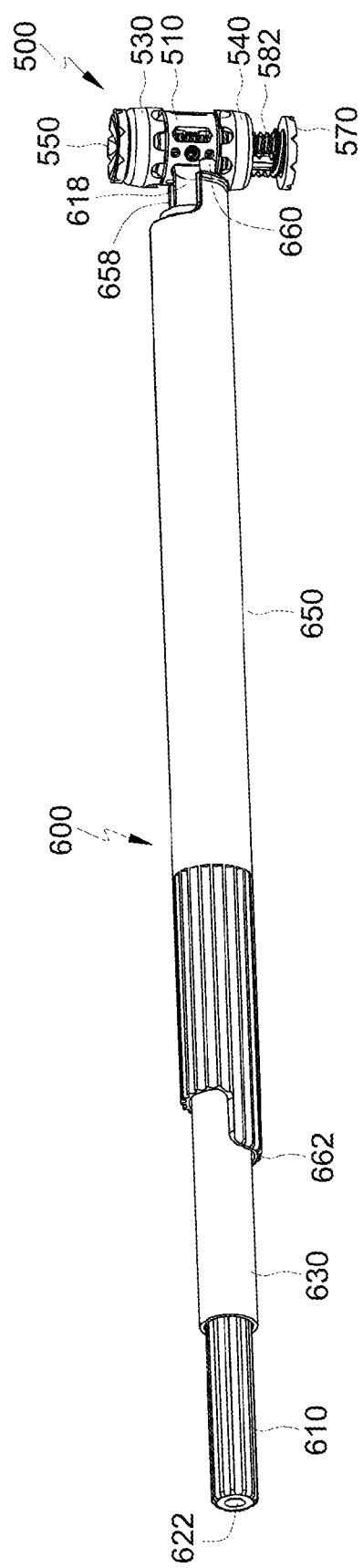
FIG. 82 is a perspective view of another embodiment vertebral body implant system including the implant of FIG. 57 and a second insertion tool in a first position, in accordance with an aspect of the present invention.
Figure 83:
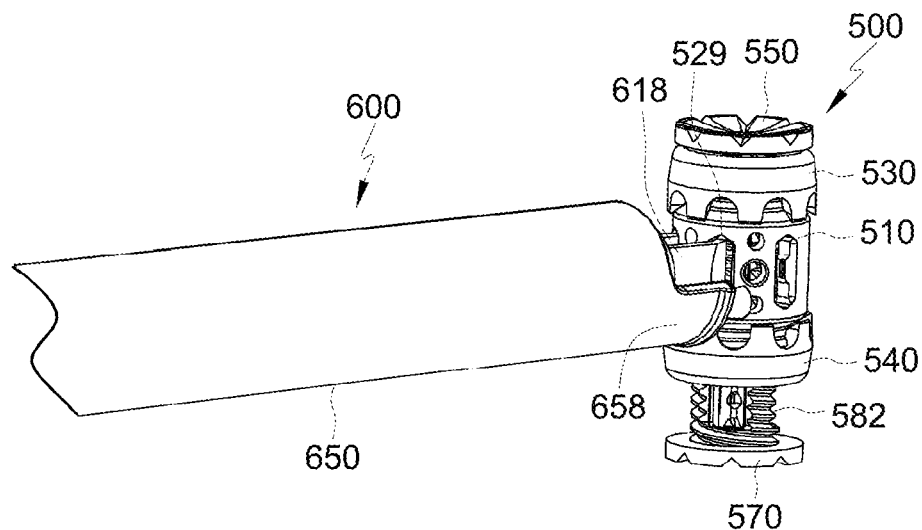
FIG. 83 is an enlarged perspective view of a portion of the system of FIG. 82, in accordance with an aspect of the present invention.

Referring now to FIGS. 77, 82, and 83, the second deployment handle 650 includes a first end 652 and a second end 654 opposite the first end 652. The second deployment handle 650 also including an opening 656 extending between the first end 652 and the second end 654. The first end 652 may also include a semi-circular protrusion 658 and the end of the protrusion 658 may include a plurality of projections 660. The plurality of projections 660 may be, for example, cone shaped or angled toward the point of attachment with the semi-circular protrusion 658 at the first end 652 of the handle 650 to allow for the projections 660 to engage the grooves or teeth 532, 542 of the rotating members 530, 540. The teeth 532, 542 may have, for example, an undercut or angled shape to lock the plurality of projections 660 into the teeth 532, 542 and prevent jumping of the projections 660 with respect to the teeth 532, 542 as the handle 650 is rotated. The second end 654 may also include a semi-circular protrusion 662 aligned with the semi-circular protrusion 658 on the first end 652.

Figure 79:
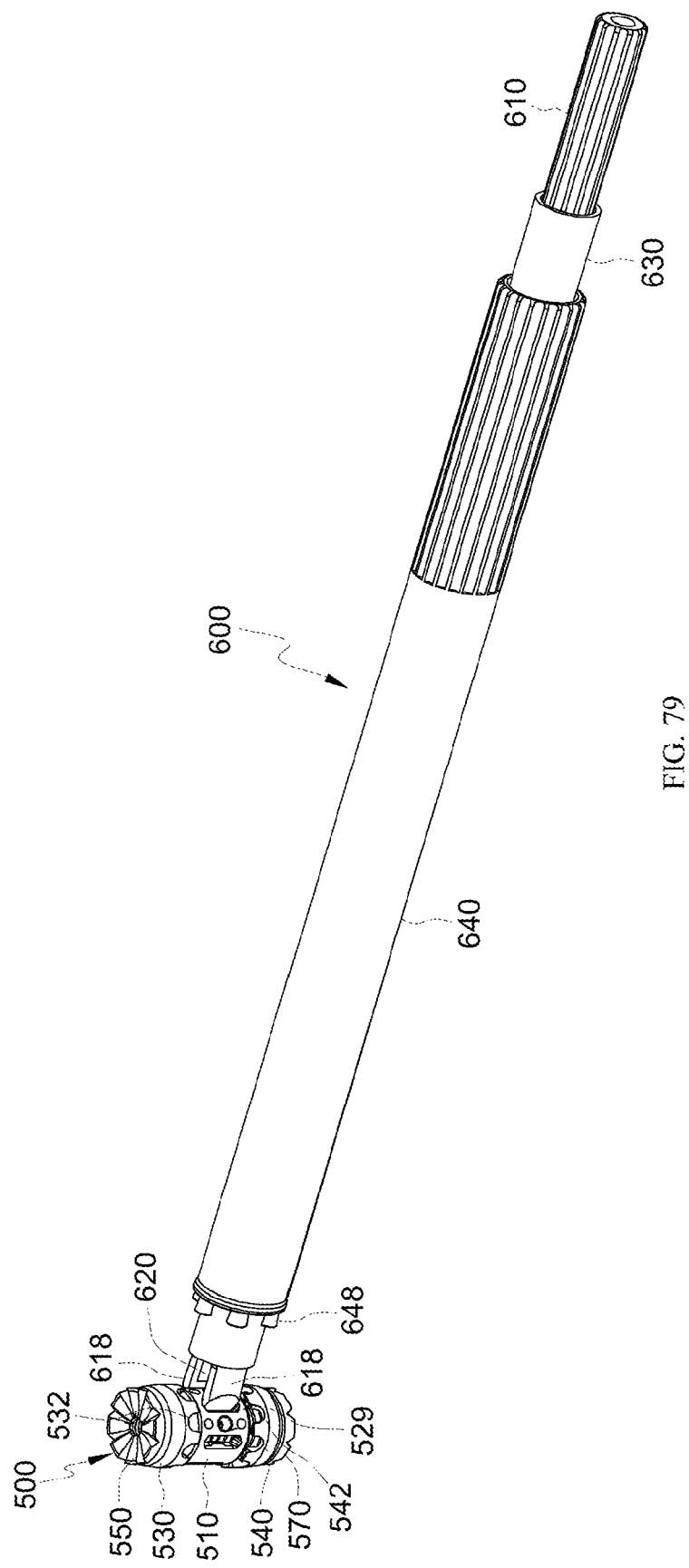
FIG. 79 is a perspective view of the vertebral body implant system of FIG. 78 with a tong member of the insertion tool engaging the vertebral body implant of FIG. 57, in accordance with an aspect of the present invention.
Figure 80:
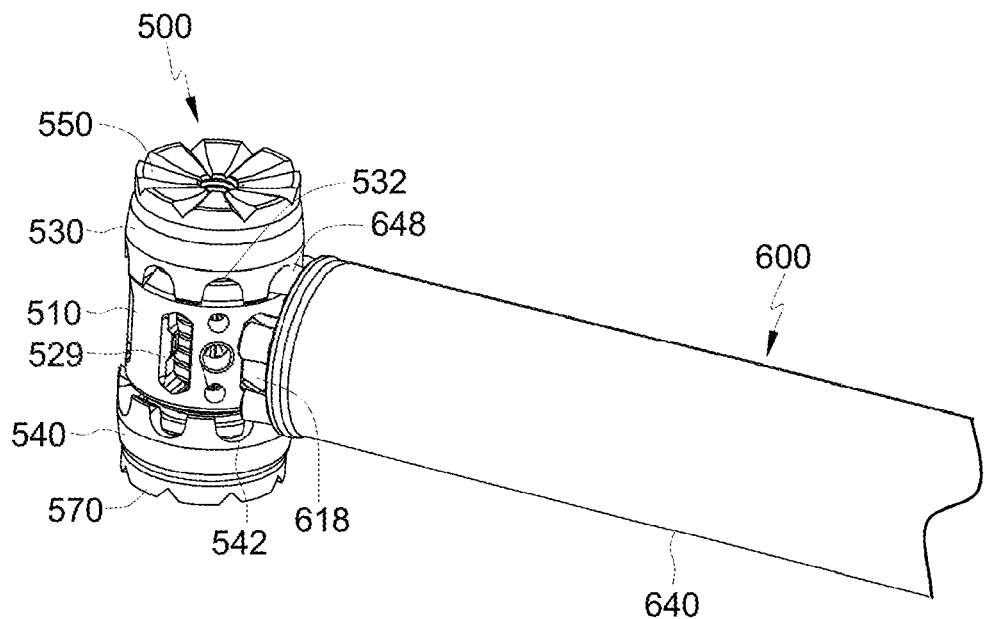
FIG. 80 is a perspective view of a portion of the system of FIG. 78 with the tool engaging the vertebral body implant in a first position, in accordance with an aspect of the present invention.
Figure 81:
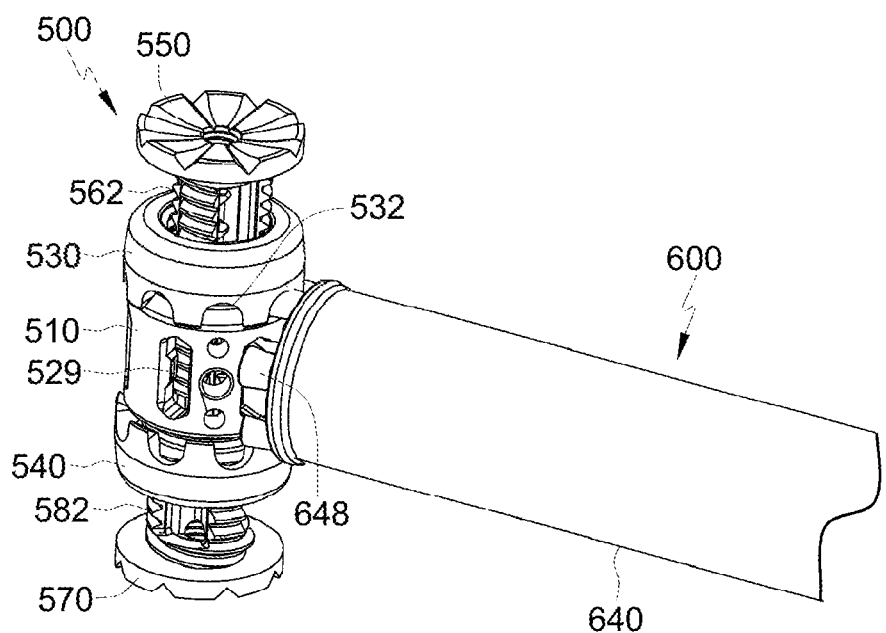
FIG. 81 is a perspective view of a portion of the system of FIG. 78 with the tool engaging the vertebral body implant in a second position, in accordance with an aspect of the present invention.

Referring now to FIGS. 78-86, methods of using the vertebral body implant 500 and insertion instruments 600 are shown. The method includes obtaining a vertebral body implant 500 and an insertion instrument 600. The vertebral body implant 500 and insertion instrument 600 may be assembled as described in greater detail above, which will not be described again here for brevity's sake. The instrument 600 may then be coupled to the vertebral body device 500 by inserting the gripping arms 618 of the gripping member 610 into the openings 523 to engage the gripping surfaces 525, as shown in FIG. 79. The gripping member 610 may be pre-loaded with a locking member 590 positioned between the gripping arms 618. The locking mechanism 590 may engage the aperture 524 and locking holes 526, 528 of the body 510.

Once the gripping member 610 is coupled to the implant 500, the compression sleeve 630 may be inserted over the gripping member 610. The compression sleeve 630 may engage the gripping member 610 to secure the gripping arms 618 to the implant 500 for insertion into the patient. Next, a deployment handle 640, 650 may be selected. If the surgeon wants to simultaneously extend both the expansion members 550, 570, then the first deployment handle 640 may be selected. Alternatively, if the surgeon wants to extend only one expansion member 550, 570 at a time, then the second deployment handle 650 may be selected.

After the deployment handle 640, 650 is selected it may be slid over the coupled gripping member 610 and compression sleeve 630. The plurality of projections 648, 660 of the selected deployment handle 640, 650 may be aligned with at least one set of the plurality of notches 532, 542 in at least one of the rotating members 530, 540. Once aligned the selected deployment handle 640, 650 may be rotated to turn at least one of the rotating members 530, 540. As at least one of the rotating members 530, 540 turns, at least one of the expansion members 550, 570 translates in a superior-inferior direction to expand the size of the implant 500. The first extension member 550 will translate in a superior direction increasing the height of the vertebral body implant 500. The second extension member 570 will translate in an inferior direction increasing the height of the vertebral body implant 500. The amount of superior-inferior translation is limited by the length of the leg members 562, 582. Alternatively, if the deployment handle 640, 650 is rotated in the reverse direction, at least one of the rotating members 530, 540 may be rotated in the reverse direction and at least one of the extension members 550, 570 will translate in the superior-inferior direction to decrease the height of the vertebral body implant 500. Once the desired configuration and height of the vertebral body implant 500 is achieved, the locking mechanism 590 may be tightened to lock the vertebral body implant 500 by inserting a driver through the insertion instrument 600. The locking mechanism 590 may be tightened with, for example, a hex wrench inserted through the center opening 524 of the instrument 600 to tighten the fastener 598 and secure the locking plate 592 in place on the implant 500. The locking mechanism 590 may engage the aperture 524 and locking holes 526, 528 of the body 510. Alternatively, the locking mechanism 590 may be inserted through the opening 622 in the gripping member 610 once the desired expansion is achieved. After the implant 500 is secured in the desired expanded position, the insertion tool 600 may be removed from the vertebral body implant 500.

Another embodiment vertebral body replacement device 700 and insertion instrument 800 are shown in FIGS. 87-90. The vertebral body device 700 may include a body 710, a first rotating member 730 rotatably coupled to the first end 712 of the body 710, a second rotating member 740 rotatably coupled to the second end 714 of the body 710, a first extension member 750 moveably coupled to the first end 712 of the body 710, and a second extension member 770 moveably coupled to a second end 714 of the body 710.

Figure 88:
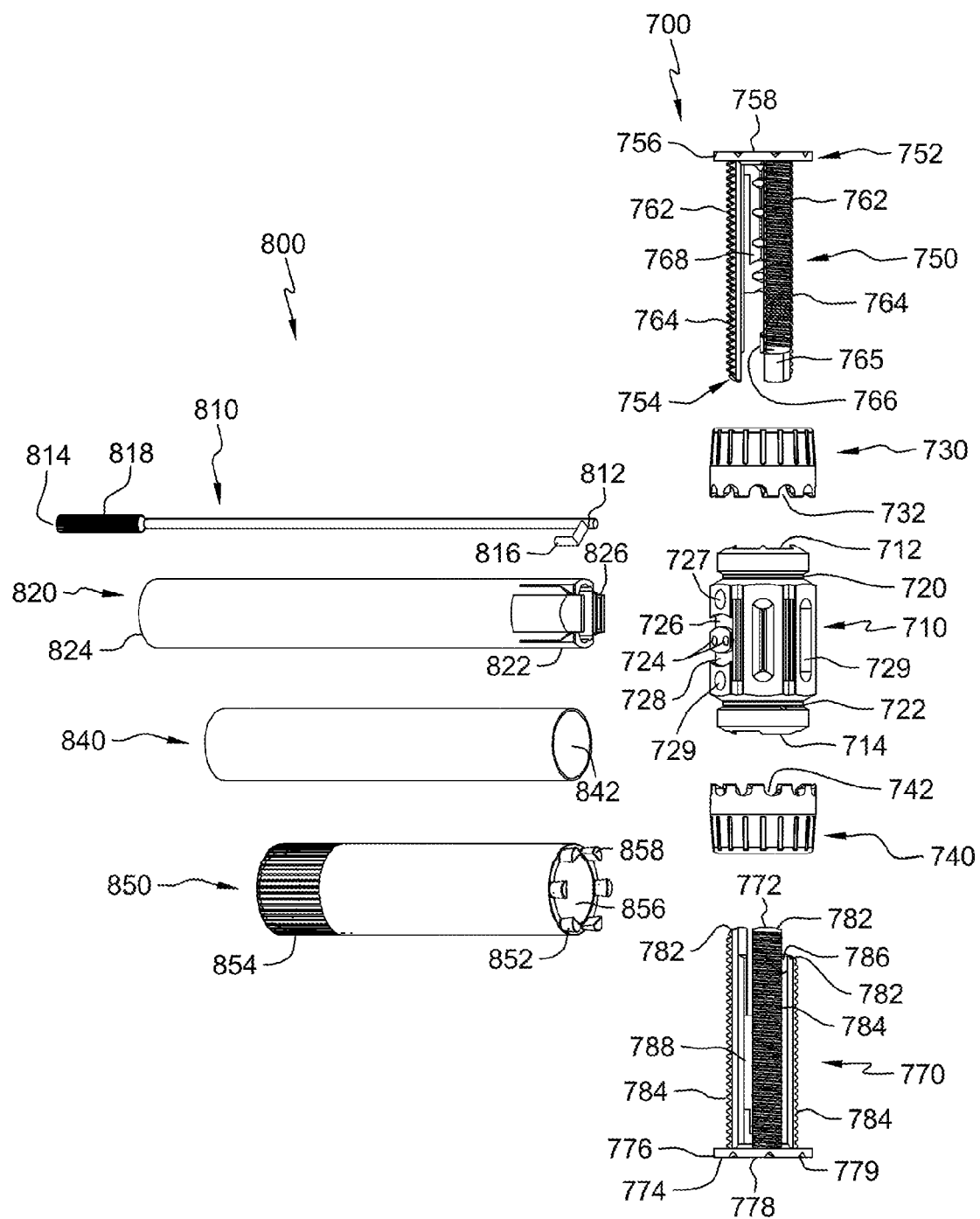
FIG. 88 is an exploded perspective view of the system of FIG. 87, in accordance with an aspect of the present invention.
Figure 90:
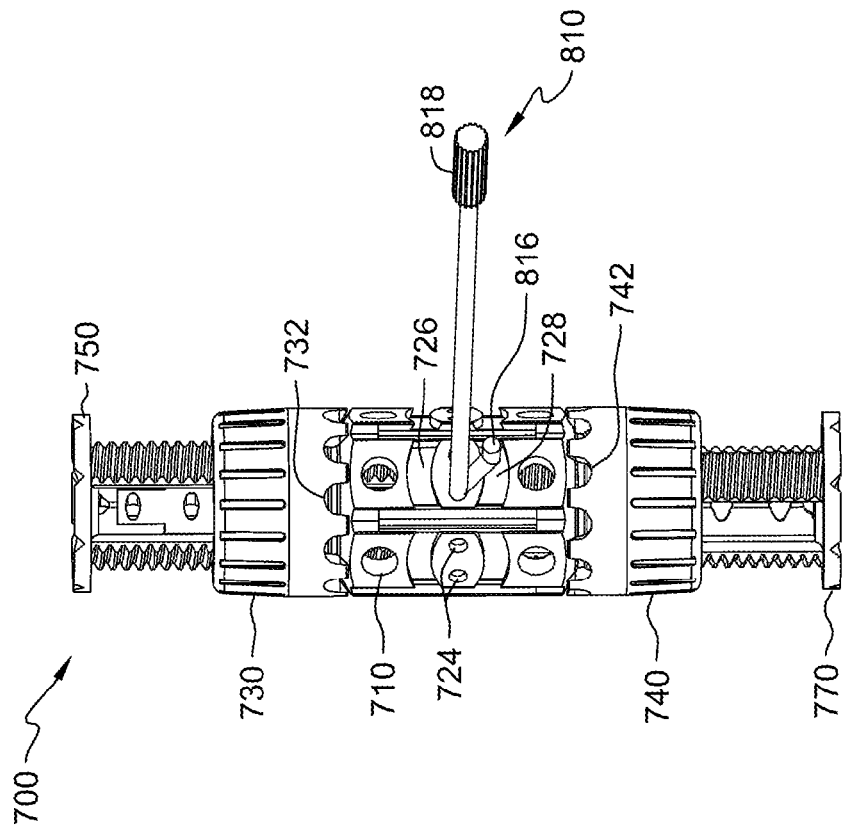
FIG. 90 is a side view of the system of FIG. 87 showing only a portion of the insertion tool, in accordance with an aspect of the present invention.

As shown in FIG. 88, the body 710 may include an opening (not shown) extending from the first end 712 to the second end 714, for example, along the longitudinal axis of the body 710. The opening (not shown) may include at least two channels (not shown) extending into the body 710 from the opening. The opening and channels may be of the type described above with reference to opening 516 and channels 517, 518, 519, which will not be described again here for brevity's sake. The exterior surface of the body 710 may further include a first groove 720 near the first end 712 and a second groove 722 near the second end 714, as shown in FIG. 88. The first and second grooves 720, 722 may extend around the circumference of the body 710 and be sized to receive the first and second rotating members 730, 740, respectively. As shown in FIGS. 88 and 90, the body 710 may also include at least one driver slot 726, 728 positioned on at least one section of the exterior surface. In one embodiment the driver slots 726, 728 may be located on three faces of the body 710 each spaced 60° apart from each other. The body 710 may also include at least one driver hole 724 positioned between the driver slots 726, 728. Further, the locking faces may include openings 727, 729 for receiving set screws (not shown) to secure the implant 700 in the desired expansion. The openings 727, 729 may be threaded. A first opening 727 may be positioned superior to the driver slots 726, 728 and the second opening 729 may be positioned inferior to the driver slots 726, 728. The body 710 may also include at least one opening 729 positioned on the non-locking faces. The at least one opening 729 may be sized and shaped to optimize bone grafting.

Figure 89:
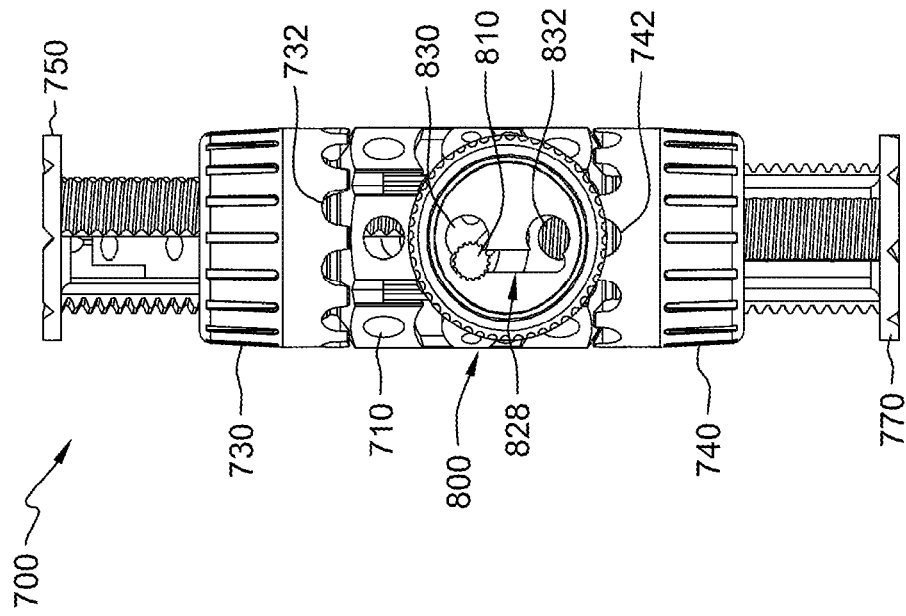
FIG. 89 is a side view of the implant of FIG. 87 and an end view of the insertion tool of FIG. 87, in accordance with an aspect of the present invention.

Rotating members 730, 740 are shown in FIG. 88 and the first rotating member 730 may include a center opening (not shown) extending through the first rotating member 730. The exterior surface of the first rotating member 730 may include a plurality of grooves, notches, gear teeth, teeth, or scallops 732, as best seen in FIGS. 88-90. The plurality of notches 732 may be, for example, sized to receive an insertion tool, such as tool 800 described in greater detail below. The first rotating member 730 may also include threads (not shown) on the interior surface of the member 730.

The second rotating member 740, as shown in FIG. 88, may include a plurality of notches 742, a center opening (not shown), and threads (not shown). The plurality of notches 542, center opening (not shown), and threads (not shown) may be of the type described above with reference to the plurality of grooves 732, center opening (not shown), and threads (not shown) of first rotating member 730, which will not be described again here for brevity's sake.

Referring now to FIG. 88, the extension members 750, 770 are shown. The first extension member 750 may include a first end 752 and a second end 754. The first extension member 750 may also include a top portion or first end cap 756 at the first end 752 and at least one leg member 762 extending away from the top portion 756 and toward the second end 754. The top portion 756 may include a top surface 758 and a center opening 760. The top surface 758 may also include grooves 759. The top surface 758, grooves 759, and center opening 760 may be configured to receive autologous bone graft or allograft material which will contact and allow for fusion with the adjacent vertebral bodies and additional graft material positioned between the at least one leg member 562. The surface 758 may be, for example, sized to allow the graft material to be positioned within the first extension member 750 to minimize the height. In addition, the top surface 758 may be shaped, for example, to receive graft material to allow for bone ingrowth to achieve the desired fusion. The top surface 758 may be, for example, coated, textured, porous, or of a trabecular metal nature to allow for bone growth into the first extension member 750 after implantation. In an alternative embodiment, it is also contemplated that the curved top surface 758 may be, for example, a mesh or open slotted top surface to allow for the bone graft material positioned in the top portion 756 to make contact with bone graft material positioned between the at least one leg member 762. The top portion 756 may also be configured to receive, for example, end caps (not shown) with lordosis or a larger footprint to contact larger adjacent vertebral bodies at the outer ring of their end plates.

The at least one leg member 762 may be, for example, three leg members 762, as shown in FIGS. 88-90. The leg members 762 may include threads 764 on an exterior surface. The leg members 762 may include a short leg member 762 and two longer leg members 762. The short leg member 762 may be received within a channel which does not extend the entire length of the body 710. In one embodiment, as shown in FIG. 88, the shorter leg member 762 may include a protrusion or hook 766 positioned on the distal portion of the leg member 762. The protrusion or hook 766 may be sized and shaped to engage a retention pin, for example, the protrusion 766 may include a proximal portion that is angled toward the leg member 762 creating a recess for receiving the retention pin. The longer leg members 762 may each be received within a channel which extends through the entire length of the body 710. The longer leg members 762 may each include, for example, a recessed region 765. In an alternative embodiment, for example, one of the longer leg members 762 may include the protrusion or hook 766 and the shorter leg member 762 and the second longer leg member 762 may each include a recessed region 765. The threads 764 on the legs 762 engage the threads 736 on an interior surface of the first rotating member 730 to translate the leg member 762 with respect to the body 710. The threads 764 may extend from the second end 754 to a bottom surface of the first end cap 756. The leg members 762 may be curved to enable the leg members 762 to rotate with respect to the first rotating member 730. The first extension member 750 may also include support members 768 positioned between and connected to the leg members 762. The support members 768 may be, for example, cross-hatching braces positioned in rings. As depicted in FIG. 88, the support members 768 may, for example, extend out from the back side of the leg members 762 and be connected between the leg members 762 in "Y" or "T" shaped arrangements. The support member 768 may alternatively form an inner cylinder aligned with the opening 760 to form an inner channel through the implant 700. The arrangement of the leg members 762 may be, for example, curved between the leg members 762 to form a ring-like shape.

The second extension member 770, as shown in FIG. 88, may include a first end 772 and a second end 774. The second extension member 770 may also include a bottom portion or second end cap 776 at the first end 772 and at least one leg member 782 extending away from the bottom portion 776 and to the second end 774. The bottom portion 776 may include a curved bottom surface 778 and an opening 780. The curved bottom surface 778 may be of the type described above with respect to the curved top surface 758, which will not be described again here for brevity's sake. The curved bottom surface 778 and center opening 780 may also be configured to receive autologous bone graft or allograft material as described in greater detail above with respect to the first extension member 750.

The at least one leg member 782 may be, for example, three leg members 782 and may include threads 784, protrusion or hook 786, and support members 788. The threads 784, protrusions 786, and support members 788 may be of the type described above with reference to threads 764, protrusion or hook 766, and support members 768, which will not be described again here for brevity's sake. The leg members 782 may include a short leg member 782 and two longer leg members 782. The short leg member 782 may be received within a channel which extends along a portion of the length of the body 710. A first longer leg member 782 may include a protrusion or hook 786 for engaging a channel 719 in the body 710. A second longer leg member 782 may include, for example, a recessed region 787. The threads 784 on the legs 782 engage the threads 746 on an interior surface of the second rotating member 740 to translate the leg member 782 with respect to the body 710. The threads 784 may extend from the first end 772 to a bottom surface of the second end cap 776. The leg members 782 may be curved to enable the leg members 782 to rotate with respect to the second rotating member 740. The first extension member 750 may also include support members 788 positioned between and connected to the leg members 782. The support members 788 may be, for example, cross-hatching braces positioned in rings. As depicted in FIG. 88, the support members 788 may, for example, extend out from the back side of the leg members 782 and be connected between the leg members 782 in "Y" or "T" shaped arrangements. The support member 788 may alternatively form an inner cylinder aligned with the opening 780 to form an inner channel through the implant 700. The arrangement of the leg members 782 may be, for example, curved between the leg members 782 to form a ring-like shape.

As shown in FIGS. 88-89, the insertion instrument 800 may include shifter 810, a gripper member 820, a locking sleeve 840, and a driver sleeve 850. The shifter 810 includes a first end 812, a second end 814, an extension member 816 and a handle 818. The gripper member 820 includes a first end 822, a second end 824 and an opening 828, 830, 832 extending between the first end 822 and the second end 824. The gripper member 820 may also include at least two gripper arms 826 sized and shaped to engage the body 710 of the implant 700. The opening 828, 830, 832 may include a slot 828 extending in a superior-inferior direction, a first opening 830 positioned at the superior end of the slot 828 and a second opening 832 positioned at the inferior end of the slot 828. The opening 828, 830, 832 may be shaped to receive the shifter 810.

With continued reference to FIG. 88, the locking sleeve 840 may include an opening 842 extending from a first end to a second end of the locking sleeve 840. The opening 842 may be sized and shaped to receive the gripper member 820 to secure the gripping arms 826 to the implant 700. The drive sleeve 850 may include a first end 852 and a second end 854. The driver sleeve 850 may also include an opening 856 extending from the first end 852 to the second end 854 and a plurality of projections, protrusions, teeth, or gear members 858 for engaging the rotating members 730, 740. The plurality of projections 858 may be, for example, cone shaped or angled toward the point of attachment with the first end of the drive sleeve 850 to allow for the projections 858 to engage the grooves or teeth 732, 742 of the rotating members 730, 740. The teeth 732, 742 may have, for example, an undercut or angled shape to lock the plurality of projections 858 into the teeth 732, 742 and prevent jumping of the projections 858 with respect to the teeth 732, 742 as the drive sleeve 850 is rotated.

Referring now to FIGS. 89-90, the extension member 816 of the shifter 810 engages the slots 726, 728 to move the driver sleeve 850 from engagement with the first rotating member 730 to the second rotating member 740 and vice versa. The shifter 810 may be positioned in the first opening 830 to engage the second rotating member 740, as shown in FIG. 89, and in the second opening 832 to engage the first rotating member 730. Once an extension member 750, 770 is positioned at the desired extension a set screw may be inserted into the respective opening 727, 729 to secure the extended extension member 750, 770. After one extension member 750, 770 is expanded and secured, the second extension member 750, 770 may be extended and secured.

Figure 92:
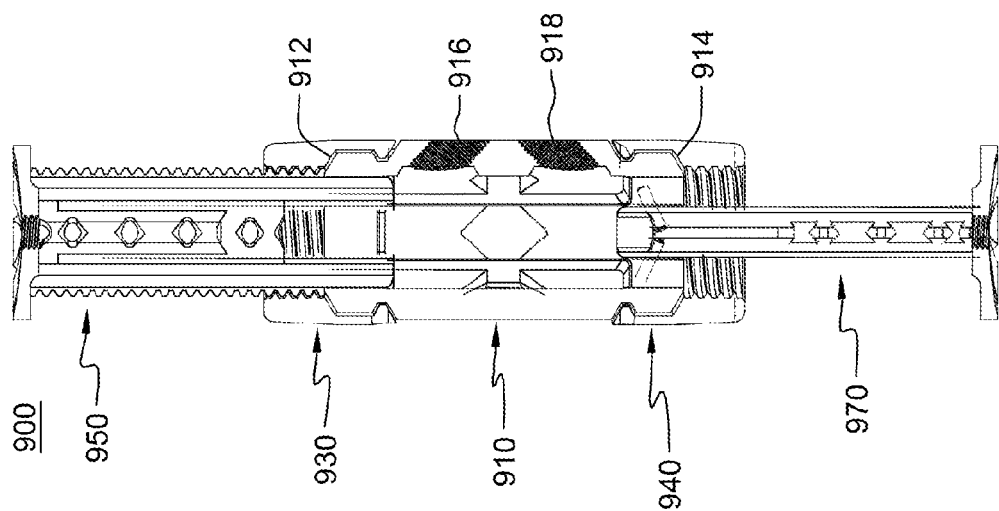
FIG. 92 is a cross-sectional view of the vertebral body implant of FIG. 91 showing the angled set screw openings, in accordance with an aspect of the present invention.
Figure 91:
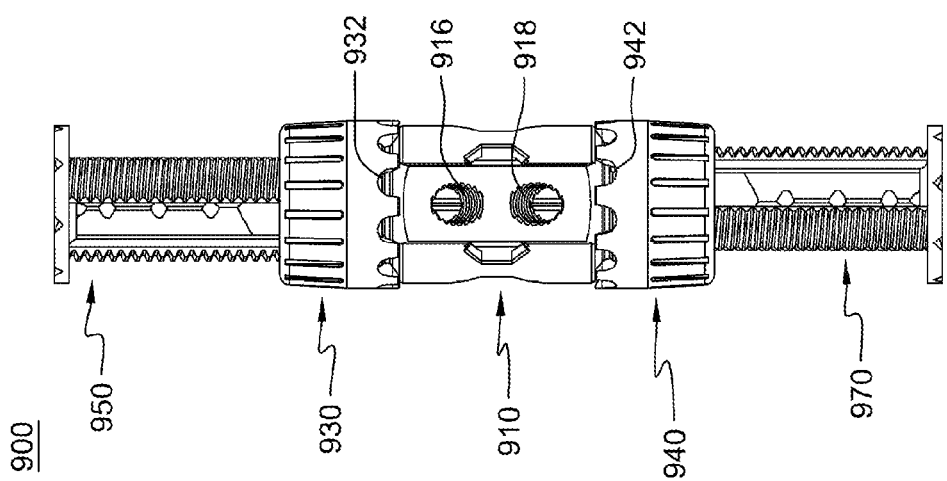
FIG. 91 is a side view of another embodiment of a vertebral body implant, in accordance with an aspect of the present invention.

FIGS. 91-92 show another embodiment of a vertebral body replacement implant 900. The implant 900 may include a body 910, a first rotating member 930 rotatably coupled to the first end 912 of the body 910, a second rotating member 940 rotatably coupled to the second end 914 of the body 910, a first extension member 950 moveably coupled to the first end 912 of the body 910, and a second extension member 970 moveably coupled to a second end 914 of the body 910. The body may include a first end 912 and a second end 914. As shown in FIG. 92, the body 910 may include a first angled opening 916 and a second angled opening 918. The angled openings 916, 918 may be, for example, threaded openings. The first angled opening 916 may extend in a superior direction and the second angled opening 918 may extend in an inferior direction. The first rotating member 930 and the second rotating member 940 may be of the type described above with reference to rotating members 730, 740 and which will not be described again here for brevity's sake. The first extension member 950 and second extension member 970 may be of the type described above with reference to extension members 750, 770 and which will not be described again here for brevity's sake.

Figure 93:
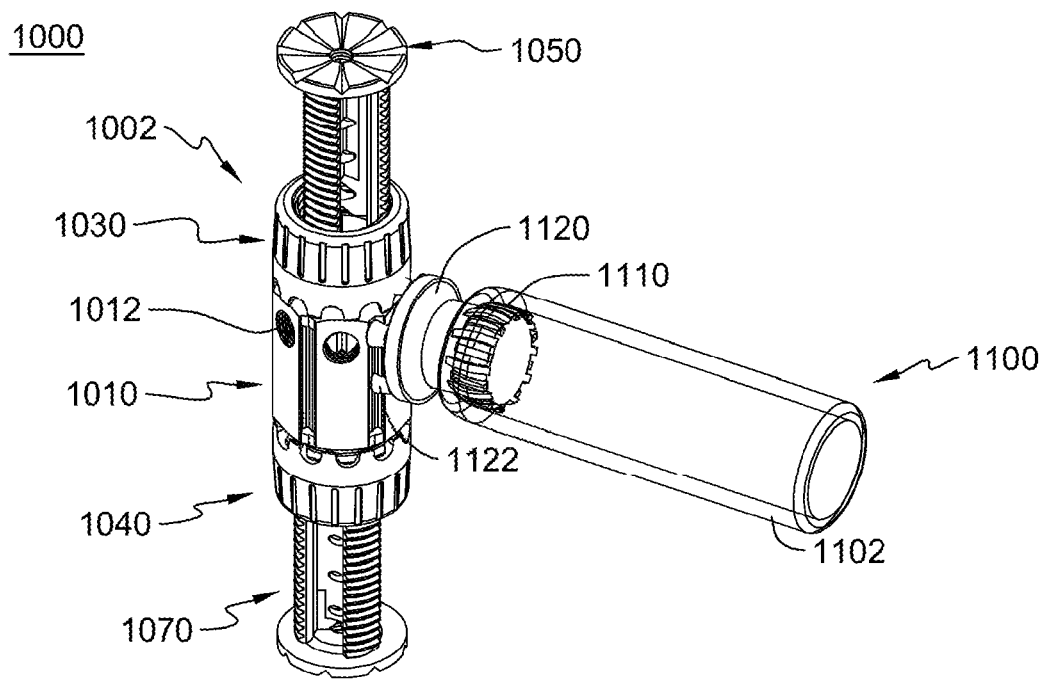
FIG. 93 is another embodiment of a vertebral body system including an implant and insertion instrument, in accordance with an aspect of the present invention.
Figure 94:
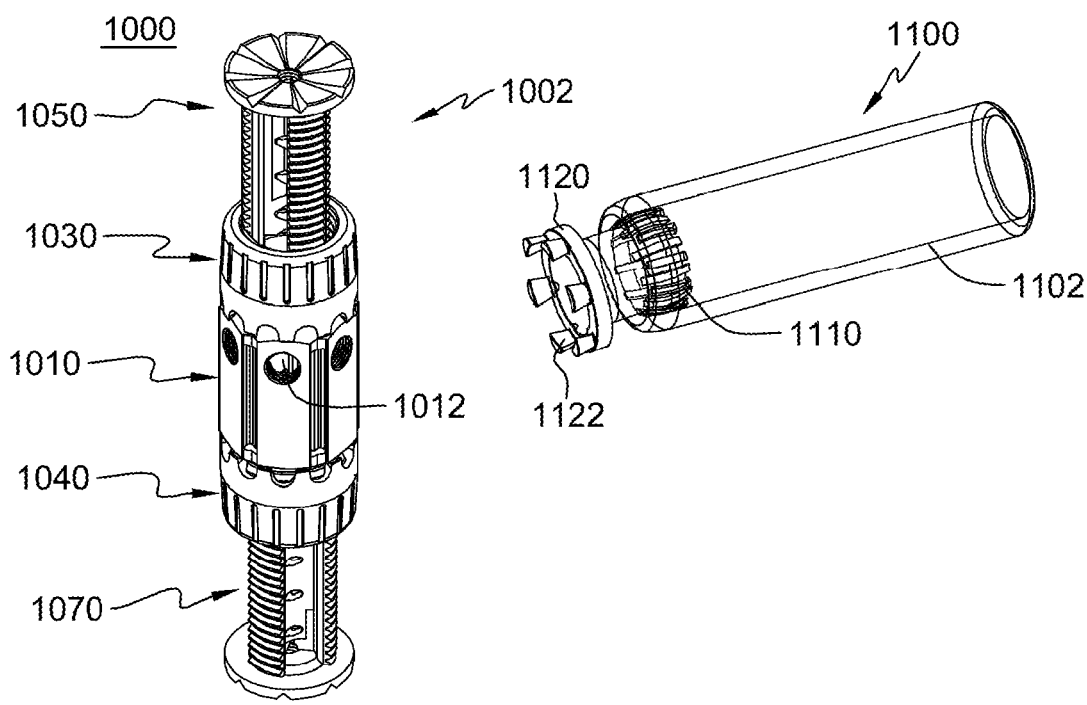
FIG. 94 is a partially exploded view of the vertebral body system of FIG. 93, in accordance with an aspect of the present invention.

Another embodiment vertebral body replacement system 1000 is shown in FIGS. 93-94. The system 1000 includes an implant 1002 and a driver sleeve 1100. The implant 1002 may include a body 1010, a first rotating member 1030 rotatably coupled to the first end 1012 of the body 1010, a second rotating member 1040 rotatably coupled to the second end 1014 of the body 1010, a first extension member 1050 moveably coupled to the first end 1012 of the body 1010, and a second extension member 1070 moveably coupled to a second end 1014 of the body 1010. The body may include a first end 1012 and a second end 1014. As shown in FIGS. 93-94, the body 1010 may include at least one opening 1012. The openings 1012 may be, for example, threaded openings. The first rotating member 1030 and the second rotating member 1040 may be of the type described above with reference to rotating members 730, 740, 930, 940 and which will not be described again here for brevity's sake. The first extension member 1050 and second extension member 1070 may be of the type described above with reference to extension members 750, 770, 950, 970 and which will not be described again here for brevity's sake.

The driver sleeve 1100 may include a body 1102 and a driver head 1120 at a first end of the body 1102. The driver head 1120 may include a pivoting member 1110 coupled to the body 1102 and a plurality of projections, protrusions, teeth, gear members 1122 for engaging the rotating members 1030, 1040. The plurality of projections 1122 may be, for example, cone shaped or angled toward the point of attachment with the first end of the driver head 1120 to allow for the projections 1122 to engage the grooves or teeth 1032, 1042 of the rotating members 1030, 1040. The teeth 1032, 1042 may have, for example, an undercut or angled shape to lock the plurality of projections 1122 into the teeth 1032, 1042 and prevent jumping of the projections 1122 with respect to the teeth 1032, 1042 as the driver head 1120 and body 1102 are rotated. The pivoting member 1110 may be, for example, a splined end that allows for the driver 1100 to pivot at an angle while being rotated to turn the rotating members 1030, 1040.

Figure 95:
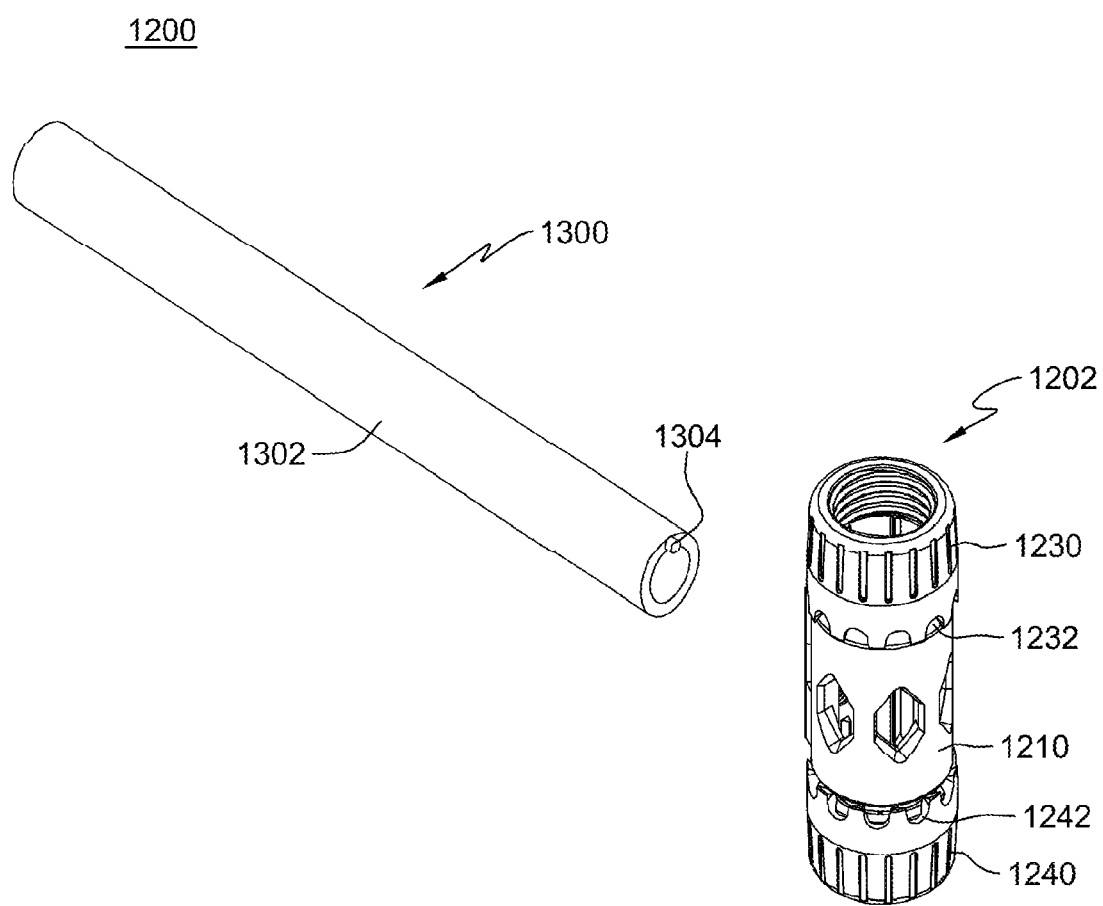
FIG. 95 is a perspective partially exploded view of another embodiment vertebral body system including an implant and an insertion instrument, in accordance with an aspect of the present invention.
Figure 96:
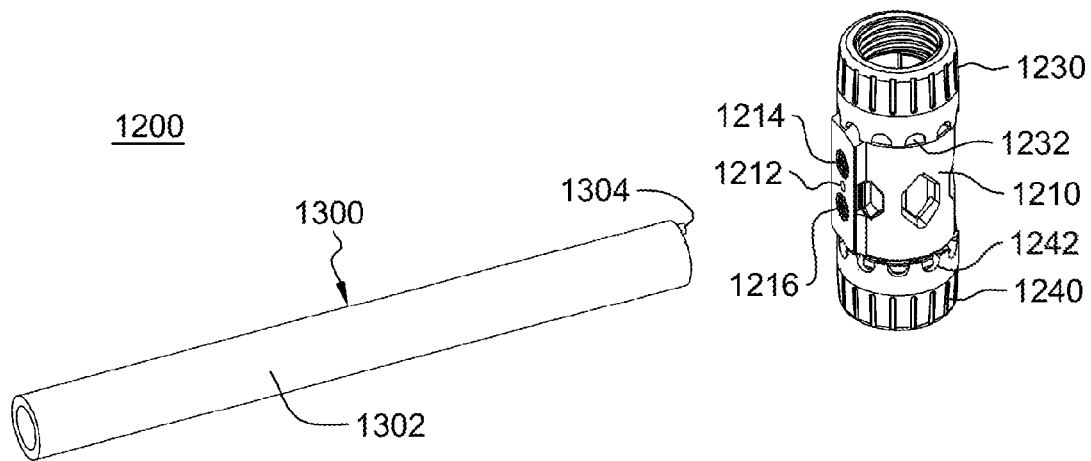
FIG. 96 is another perspective partially exploded view of the vertebral body system of FIG. 95, in accordance with an aspect of the present invention.
Figure 97:
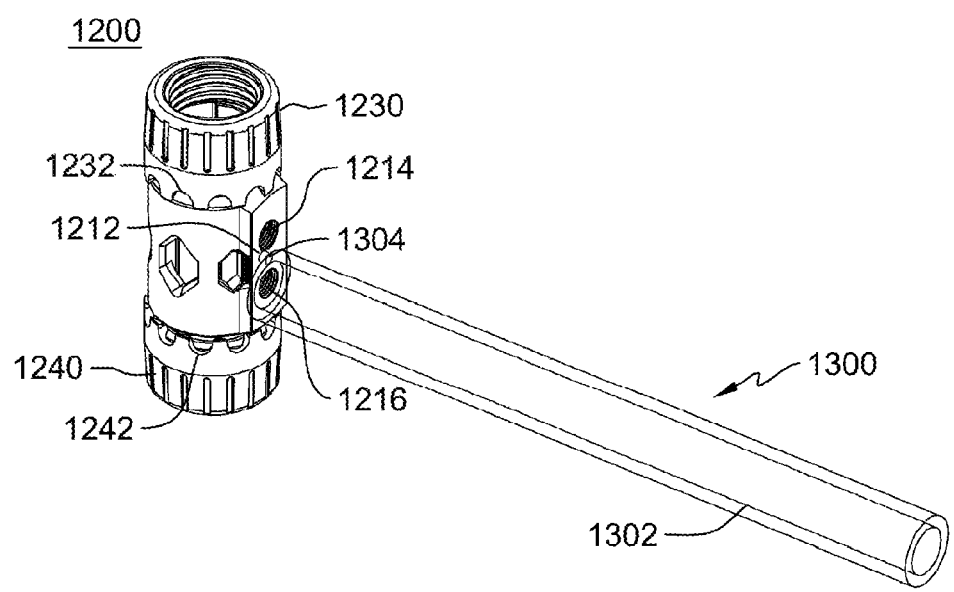
FIG. 97 is perspective view of the system of FIG. 95 with a transparent insertion instrument, in accordance with an aspect of the present invention.

FIGS. 95-97 illustrate another embodiment of a vertebral body replacement system 1200. The system 1200 includes an implant 1202 and a drive mechanism 1300. The implant 1202 may include a body 1210, a first rotating member 1230 rotatably coupled to the first end 1212 of the body 1210, a second rotating member 1240 rotatably coupled to the second end 1214 of the body 1210, a first extension member (not shown) moveably coupled to the first end 1212 of the body 1210, and a second extension member (not shown) moveably coupled to a second end 1214 of the body 1210. The body 1210 include at least one opening 1212. The opening 1212 may be sized to engage the drive sleeve 1300. The first rotating member 1230 and the second rotating member 1240 may be of the type described above with reference to rotating members 730, 740, 930, 940 and which will not be described again here for brevity's sake. The first extension member 1250 and second extension member 1270 may be of the type described above with reference to extension members 750, 770, 950, 970 and which will not be described again here for brevity's sake.

The drive sleeve 1300 may include a body 1302 and a coupling protrusion 1304. The coupling protrusion engages the opening 1212 in the body 1210. The drive sleeve 1300 is then positioned for engagement with one of the rotating members 1230, 1240 to expand the implant 1202. Although not shown, a deployment handle, such as deployment handles 640, 650 as described in greater detail above, may be slid over the body 1302 to engage one of the rotating members 1230, 1240 to expand the implant 1202. Once a first rotating member 1230, 1240 is expanded, then the deployment handle (not shown) may be disengaged from the teeth 1232, 1242. Next, the drive sleeve 1300 may be rotated to a second position and the deployment handle (not shown) positioned to engage the second rotating member 1230, 1240 to expand the implant 1200.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An expandable cage system, comprising:
   a vertebral body device, comprising:
   a body with a first end and a second end, the body comprising:
   at least one aperture positioned on the body along a midpoint between the first end and the second end;
   at least one first locking hole positioned superior to the at least one aperture; and
   at least one second locking hole positioned inferior to the at least one aperture;
   a first rotating member coupled to the first end;
   a second rotating member coupled to the second end;
   a first extension member moveably coupled to the first end; and
   a second extension member moveably coupled to the second end; and
   an insertion instrument, wherein the insertion instrument is sized to be placed around the at least one aperture, the at least one first locking hole, and the at least one second locking hole and wherein the insertion instrument comprises:
   a gripping member;
   a compression sleeve sized to engage the gripping member; and
   at least one rotating member sized to receive the compression sleeve and the gripping member, wherein the at least one rotating member comprises:
   a first end having a plurality of projections positioned around the circumference of the first end.

2. The expandable cage system of claim 1, wherein the body further comprises:
   at least one opening positioned on each side of the at least one aperture, wherein the gripping member is inserted into the at least one opening on each side of the aperture and wherein the gripping member engages a side of each of the at least one openings.

3. An expandable cage system, comprising:
   a vertebral body device, comprising:
   a body with a first end and a second end, the body comprising:
   at least one aperture positioned on the body along a midpoint between the first end and the second end;
   at least one first locking hole positioned superior to the at least one aperture; and at least one second locking hole positioned inferior to the at least one aperture;
a first rotating member coupled to the first end;
a second rotating member coupled to the second end;
a first extension member moveably coupled to the first end; and
a second extension member moveably coupled to the second end; and
wherein at least one rotating member comprises:
a first end having a first semi-circular protrusion and a plurality of projections positioned around the first protrusion on the first end; and
an insertion instrument, wherein the insertion instrument is sized to be placed around the at least one aperture, the at least one first locking hole, and the at least one second locking hole and wherein the insertion instrument comprises:
a gripping member;
a compression sleeve sized to engage the gripping member; and
at least one rotating member sized to receive the compression sleeve and gripping member.

4. The expandable cage system of claim 3, wherein the at least one rotating member comprises:
a second end having a second semi-circular protrusion extending away from the second end and aligned with the first semi-circular protrusion around the circumference of the rotating member.

5. The expandable cage system of claim 3, wherein the body further comprises:
at least one opening positioned on each side of the at least one aperture, wherein the gripping member is inserted into the at least one opening on each side of the aperture and wherein the gripping member engages a side of each of the at least one openings.

6. A method of using an expandable cage system, comprising:
obtaining a vertebral body implant, the vertebral body implant comprising:
a body with a first end and a second end;
a first rotating member rotatably coupled to the first end;
a second rotating member rotatably coupled to the second end;
a first extension member moveably coupled to the first end; and
a second extension member moveably coupled to the second end;
obtaining an insertion instrument, wherein the insertion instrument comprises:
a gripping member;
a compression sleeve sized to engage the gripping member; and
at least one rotating member sized to receive the compression sleeve and gripping member, and wherein the at least one rotating member comprises:
a first end having a semi-circular protrusion and a plurality of projections positioned around the protrusion on the first end, wherein the semi-circular protrusion engages one of the first rotating member and the second rotating member to expand one of the first extension member and the second extension member;
coupling the vertebral body implant to the insertion instrument;
inserting the vertebral body implant into a patient between two vertebral bodies;
expanding the vertebral body implant; and
removing the insertion instrument.

7. The method of claim 6, wherein the method further comprises:
inserting a locking member into the body of the vertebral body implant.

8. The method of claim 6, wherein expanding the vertebral body implant comprises:
rotating the at least one rotating member of the insertion instrument in a first direction to engage and rotate the first rotating member of the vertebral body implant, wherein rotating the first rotating member translates the coupled first extension member to increase a height of the vertebral body device.

9. The method of claim 6, wherein expanding the vertebral body implant comprises:
expanding only one of the first extension member and the second extension member.

10. The method of claim 6, wherein inserting a locking member into the body of the vertebral body implant comprises:
obtaining a locking plate with a first post, a second post and a bore located between the first post and the second post;
inserting a threaded fastener through the bore in the locking plate and a threaded opening in the body of the vertebral body implant; and
tightening the threaded fastener to insert the first post into an opening superior to the bore and to insert the second post into an opening inferior to the bore, wherein the first post engages the first extension member and the second post engages the second extension member to secure the vertebral body implant in an expanded position.

* * * * *